US008668929B2

(12) United States Patent
Han et al.

(10) Patent No.: US 8,668,929 B2
(45) Date of Patent: Mar. 11, 2014

(54) GASTRIC RETENTIVE EXTENDED-RELEASE DOSAGE FORMS COMPRISING COMBINATIONS OF A NON-OPIOID ANALGESIC AND AN OPIOID ANALGESIC

(75) Inventors: Chien-Hsuan Han, Sunnyvale, CA (US); Sui Yuen Eddie Hou, Foster City, CA (US); Monica L. Reid, San Mateo, CA (US)

(73) Assignee: Depomed, Inc., Newark, CA (US)

( * ) Notice: Subject to any disclaimer, the term of this patent is extended or adjusted under 35 U.S.C. 154(b) by 0 days.

(21) Appl. No.: 13/529,960

(22) Filed: Jun. 21, 2012

(65) Prior Publication Data

US 2012/0321713 A1     Dec. 20, 2012

Related U.S. Application Data

(63) Continuation of application No. 12/644,444, filed on Dec. 22, 2009, now Pat. No. 8,372,432, which is a continuation-in-part of application No. 12/402,477, filed on Mar. 11, 2009, now Pat. No. 8,377,453.

(60) Provisional application No. 61/035,696, filed on Mar. 11, 2008.

(51) Int. Cl.
A61K 9/26         (2006.01)

(52) U.S. Cl.
USPC ........................................................ 424/469

(58) Field of Classification Search
USPC ........................................................ 424/469
See application file for complete search history.

(56) References Cited

U.S. PATENT DOCUMENTS

| | | | |
|---|---|---|---|
| 4,713,243 A | 12/1987 | Schiraldi et al. |
| 4,851,226 A | 7/1989 | Julian et al. |
| 4,894,236 A | 1/1990 | Jang et al. |
| 4,996,058 A | 2/1991 | Sinnreich |
| 5,075,114 A | 12/1991 | Roche |
| 5,266,331 A | 11/1993 | Oshlack et al. |
| 5,336,691 A | 8/1994 | Raffa et al. |
| 5,478,577 A | 12/1995 | Sackler et al. |
| 5,508,042 A | 4/1996 | Oshlack et al. |
| 5,549,912 A | 8/1996 | Oshlack et al. |
| 5,582,837 A | 12/1996 | Shell |
| 5,626,874 A | 5/1997 | Conte et al. |
| 5,656,295 A | 8/1997 | Oshlack et al. |
| 5,672,360 A | 9/1997 | Sackler et al. |
| 5,783,212 A | 7/1998 | Fassihi et al. |
| 5,866,161 A | 2/1999 | Childers et al. |
| 5,876,759 A | 3/1999 | Gowan, Jr. |
| 5,891,471 A | 4/1999 | Miller et al. |
| 5,945,123 A | 8/1999 | Hermelin |
| 5,945,125 A | 8/1999 | Kim |
| 5,958,459 A | 9/1999 | Chasin et al. |
| 5,965,161 A | 10/1999 | Oshlack et al. |
| 5,965,163 A | 10/1999 | Miller et al. |
| 5,965,167 A | 10/1999 | Sanghvi et al. |
| 5,968,551 A | 10/1999 | Oshlack et al. |
| 5,972,389 A | 10/1999 | Shell et al. |
| 5,980,882 A | 11/1999 | Eichman |
| 6,024,982 A | 2/2000 | Oshlack et al. |
| 6,068,855 A | 5/2000 | Leslie et al. |
| 6,071,208 A | 6/2000 | Koivunen |
| 6,103,219 A | 8/2000 | Sherwood et al. |
| 6,103,261 A | 8/2000 | Chasin et al. |
| 6,126,969 A | 10/2000 | Shah et al. |
| 6,143,322 A | 11/2000 | Sackler et al. |
| 6,210,714 B1 | 4/2001 | Oshlack et al. |
| 6,245,357 B1 | 6/2001 | Edgren et al. |
| 6,254,887 B1 | 7/2001 | Miller et al. |
| 6,340,475 B2 | 1/2002 | Shell et al. |
| 6,348,216 B1 | 2/2002 | Kushla et al. |
| 6,372,254 B1 | 4/2002 | Ting et al. |
| 6,375,957 B1 | 4/2002 | Kaiko et al. |
| 6,387,404 B2 | 5/2002 | Oshlack et al. |
| 6,488,962 B1 | 12/2002 | Berner et al. |
| 6,488,963 B1 | 12/2002 | McGinity et al. |
| 6,491,945 B1 | 12/2002 | Childers et al. |
| 6,500,459 B1 | 12/2002 | Chhabra et al. |
| 6,599,529 B1 | 7/2003 | Skinhøj et al. |
| 6,635,280 B2 | 10/2003 | Shell et al. |
| 6,667,060 B1 | 12/2003 | Vandecruys et al. |
| 6,682,759 B2 | 1/2004 | Lim et al. |
| 6,696,066 B2 | 2/2004 | Kaiko et al. |

(Continued)

FOREIGN PATENT DOCUMENTS

| | | |
|---|---|---|
| EP | 0159852 A2 | 10/1985 |
| EP | 0305051 A1 | 3/1989 |

(Continued)

OTHER PUBLICATIONS

Gafourian (Journal of Pharmaceutical Sciences, vol. 96, No. 12, Dec. 2007).*
Sirkia (STP Pharma Sciences, 3 (6) 453-458).*
Kim (Drug Development and Industrial Pharmacy, 24(7), 645-651 (1998).*
Jagdale (AAPS PharmSciTech, vol. 10, No. 3, Sep. 2009).*
Childs, FDA panel urges cuts in acetaminophen doSage, ABC News, Jun. 30, 2009, Retrieved from the internet <URL: http://abcnews.go.com/Health/PainManagement/story?id=7965902&page=1>, 3 pages.
Divoll e al., "Effect of food on acetaminophen absorption in young and elderly subject", J. Clin. Pharmacol., vol. 22, No. 11-12, pp. 571-576 (1982).
International Search Report from PCT Patent Application No. PCT/US2010/047369 mailed May 30, 2011, application now published as PCT Publication No. WO 2011/026125 on Mar. 3, 2011.

(Continued)

Primary Examiner — David J Blanchard
Assistant Examiner — Devang Thakor
(74) Attorney, Agent, or Firm — McDermott Will & Emery LLP

(57) ABSTRACT

Compositions and methods for the treatment of pain in a mammal are described. More specifically, a dosage form designed for release of acetaminophen and an opioid is described, wherein the dosage form provides delivery of the drugs to the upper gastrointestinal tract ("GI") of a mammal for an extended period of time.

42 Claims, 15 Drawing Sheets

(56) References Cited

U.S. PATENT DOCUMENTS

| | | |
|---|---|---|
| 6,706,281 B2 | 3/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,797,283 B1 | 9/2004 | Edgren et al. |
| 6,852,336 B2 | 2/2005 | Hunter et al. |
| 6,902,742 B2 | 6/2005 | Devane et al. |
| 7,074,430 B2 | 7/2006 | Miller et al. |
| 7,201,920 B2 | 4/2007 | Kumar et al. |
| 7,374,781 B2 | 5/2008 | Zhang et al. |
| 7,405,238 B2 | 7/2008 | Markey et al. |
| 7,413,751 B2 | 8/2008 | Devane et al. |
| 7,438,927 B2 | 10/2008 | Berner et al. |
| 7,514,100 B2 | 4/2009 | Oshlack et al. |
| 7,674,799 B2 | 3/2010 | Chapman et al. |
| 7,683,072 B2 | 3/2010 | Chapman et al. |
| 7,691,873 B2 | 4/2010 | Duncalf et al. |
| 7,776,314 B2 | 8/2010 | Bartholomäus et al. |
| 7,846,476 B2 | 12/2010 | Oshlack et al. |
| 7,897,172 B2 | 3/2011 | Qasem et al. |
| 7,939,543 B2 | 5/2011 | Kupper |
| 7,943,170 B2 | 5/2011 | Chan et al. |
| 7,976,870 B2 | 7/2011 | Berner et al. |
| 8,075,872 B2 | 12/2011 | Arkenao-Maric et al. |
| 2001/0008639 A1 | 7/2001 | Oshlack et al. |
| 2002/0018810 A1 | 2/2002 | Oshlack et al. |
| 2002/0058050 A1 | 5/2002 | Sackler et al. |
| 2002/0192277 A1 | 12/2002 | Oshlack et al. |
| 2003/0035837 A1 | 2/2003 | Sackler et al. |
| 2003/0044466 A1* | 3/2003 | Markey et al. ............... 424/469 |
| 2003/0091635 A1 | 5/2003 | Baichwal et al. |
| 2003/0092724 A1* | 5/2003 | Kao et al. ...................... 514/282 |
| 2003/0099704 A1 | 5/2003 | Oshlack et al. |
| 2003/0104062 A1 | 6/2003 | Berner et al. |
| 2003/0180361 A1 | 9/2003 | Oshlack et al. |
| 2003/0235616 A1 | 12/2003 | Sowden et al. |
| 2004/0096500 A1 | 5/2004 | Oshlack et al. |
| 2004/0105887 A1 | 6/2004 | Oshlack et al. |
| 2004/0131671 A1 | 7/2004 | Zhang et al. |
| 2004/0156899 A1 | 8/2004 | Louie-Helm et al. |
| 2004/0202716 A1 | 10/2004 | Chan et al. |
| 2004/0224020 A1 | 11/2004 | Schoenhard |
| 2005/0013863 A1 | 1/2005 | Lim et al. |
| 2005/0020613 A1 | 1/2005 | Boehm et al. |
| 2005/0031546 A1 | 2/2005 | Bartholomäus et al. |
| 2005/0089570 A1 | 4/2005 | Cruz et al. |
| 2005/0106249 A1 | 5/2005 | Hwang et al. |
| 2005/0112195 A1 | 5/2005 | Cruz et al. |
| 2005/0158382 A1 | 7/2005 | Cruz et al. |
| 2005/0165038 A1 | 7/2005 | Gordon |
| 2005/0214251 A1 | 9/2005 | Pohl et al. |
| 2005/0232987 A1 | 10/2005 | Srinivasan et al. |
| 2005/0266032 A1 | 12/2005 | Srinivasan et al. |
| 2005/0267189 A1 | 12/2005 | Gao et al. |
| 2006/0002860 A1 | 1/2006 | Bartholomäus et al. |
| 2006/0057210 A1 | 3/2006 | Oshlack et al. |
| 2006/0099255 A1 | 5/2006 | Oshlack et al. |
| 2006/0165791 A1 | 7/2006 | Oshlack et al. |
| 2006/0193782 A1 | 8/2006 | Bartholomäus et al. |
| 2006/0205752 A1 | 9/2006 | Whitehead |
| 2006/0240105 A1 | 10/2006 | Devane et al. |
| 2006/0251721 A1 | 11/2006 | Cruz et al. |
| 2006/0263436 A1 | 11/2006 | Baert et al. |
| 2006/0269604 A1 | 11/2006 | Sackler et al. |
| 2006/0292214 A1 | 12/2006 | Jenkins et al. |
| 2007/0020335 A1 | 1/2007 | Chen et al. |
| 2007/0048228 A1 | 3/2007 | Arkenau-Maric et al. |
| 2007/0059359 A1 | 3/2007 | Backensfeld et al. |
| 2007/0128279 A1 | 6/2007 | Edgren et al. |
| 2007/0183980 A1 | 8/2007 | Arkenau-Maric et al. |
| 2007/0184112 A1 | 8/2007 | Wong et al. |
| 2007/0190142 A1 | 8/2007 | Breitenbach et al. |
| 2007/0207200 A1 | 9/2007 | Plachetka et al. |
| 2007/0237816 A1 | 10/2007 | Finkelstein |
| 2007/0237833 A1 | 10/2007 | Sackler et al. |
| 2007/0259033 A1 | 11/2007 | Cruz |
| 2007/0259045 A1 | 11/2007 | Mannion et al. |
| 2007/0275065 A1 | 11/2007 | Oshlack et al. |
| 2007/0281018 A1 | 12/2007 | Qiu et al. |
| 2008/0020039 A1 | 1/2008 | Parikh et al. |
| 2008/0031901 A1 | 2/2008 | Qiu et al. |
| 2008/0031963 A1 | 2/2008 | Sackler et al. |
| 2008/0044482 A1 | 2/2008 | Oshlack et al. |
| 2008/0057122 A1 | 3/2008 | Toney-Parker et al. |
| 2008/0113025 A1 | 5/2008 | Devane et al. |
| 2008/0132532 A1 | 6/2008 | Wright et al. |
| 2008/0138422 A1 | 6/2008 | Staniforth |
| 2008/0220062 A1 | 9/2008 | Ashton |
| 2009/0022798 A1 | 1/2009 | Rosenberg et al. |
| 2009/0028941 A1 | 1/2009 | Cowles et al. |
| 2009/0068269 A1 | 3/2009 | Oshlack et al. |
| 2009/0081290 A1 | 3/2009 | McKenna et al. |
| 2009/0149479 A1 | 6/2009 | Jenkins et al. |
| 2009/0155357 A1 | 6/2009 | Muhuri |
| 2009/0175937 A1 | 7/2009 | Rahmouni et al. |
| 2009/0202629 A1 | 8/2009 | Oshlack et al. |
| 2009/0304793 A1 | 12/2009 | Boehm |
| 2009/0306119 A1 | 12/2009 | Keane |
| 2009/0311320 A1 | 12/2009 | Ourey et al. |
| 2009/0317355 A1 | 12/2009 | Roth et al. |
| 2009/0324714 A1 | 12/2009 | Liu et al. |
| 2010/0010030 A1 | 1/2010 | Jain et al. |
| 2010/0015222 A1 | 1/2010 | Han et al. |
| 2010/0034876 A1 | 2/2010 | Oshlack et al. |
| 2010/0040681 A1 | 2/2010 | Park et al. |
| 2010/0092570 A1 | 4/2010 | Oshlack et al. |
| 2010/0168148 A1 | 7/2010 | Wright et al. |
| 2010/0172974 A1 | 7/2010 | Oshlack et al. |
| 2010/0172989 A1 | 7/2010 | Roth et al. |
| 2010/0196425 A1 | 8/2010 | Cruz et al. |
| 2010/0196471 A1 | 8/2010 | Jain et al. |
| 2010/0196474 A1 | 8/2010 | Han et al. |
| 2010/0216829 A2 | 8/2010 | Kumar et al. |
| 2010/0221293 A1 | 9/2010 | Cruz et al. |
| 2010/0239662 A1 | 9/2010 | Rahmouni et al. |
| 2010/0260833 A1 | 10/2010 | Bartholomäus et al. |
| 2011/0020451 A1 | 1/2011 | Bartholomäus et al. |
| 2011/0038927 A1 | 2/2011 | Oshlack et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0117196 A1 | 5/2011 | Gordon |
| 2011/0118189 A1 | 5/2011 | Farr et al. |
| 2011/0129507 A1 | 6/2011 | Cruz |
| 2011/0150969 A1 | 6/2011 | Shah et al. |
| 2011/0150970 A1 | 6/2011 | Shah et al. |
| 2011/0150971 A1 | 6/2011 | Shah et al. |
| 2011/0150989 A1 | 6/2011 | Park et al. |
| 2011/0150990 A1 | 6/2011 | Shah et al. |
| 2011/0150991 A1 | 6/2011 | Shah et al. |
| 2011/0159046 A1 | 6/2011 | Cruz |
| 2011/0166171 A1 | 7/2011 | Qiu et al. |
| 2011/0177168 A1 | 7/2011 | Chan et al. |
| 2011/0195116 A1 | 8/2011 | Hobbs et al. |
| 2011/0195989 A1 | 8/2011 | Rudnic et al. |
| 2011/0207762 A1 | 8/2011 | Chapman et al. |
| 2011/0212173 A1 | 9/2011 | Young et al. |
| 2011/0229526 A1 | 9/2011 | Rosenberg et al. |
| 2011/0229533 A1 | 9/2011 | Edgren et al. |
| 2011/0262532 A1 | 10/2011 | Oshlack et al. |
| 2011/0287095 A1 | 11/2011 | Park et al. |
| 2011/0301129 A1 | 12/2011 | Berner et al. |
| 2011/0318392 A1 | 12/2011 | Cruz et al. |
| 2012/0321713 A1 | 12/2012 | Han et al. |

FOREIGN PATENT DOCUMENTS

| | | |
|---|---|---|
| EP | 1140026 A1 | 6/2000 |
| WO | WO 97/18814 A1 | 5/1997 |
| WO | WO 98/55107 A1 | 12/1998 |
| WO | WO 03/024426 A1 | 3/2003 |
| WO | WO 2005/013863 A2 | 2/2005 |
| WO | WO 2006/022759 | 3/2006 |
| WO | WO 2006/071208 A1 | 7/2006 |

(56) References Cited

FOREIGN PATENT DOCUMENTS

| WO | WO 2005/030182 A1 | 4/2007 |
|----|----|----|
| WO | WO 2008/015221 A2 | 2/2008 |
| WO | WO 2009/049405 A1 | 4/2009 |
| WO | WO 2009/076764 A1 | 6/2009 |
| WO | WO 2009/114648 A1 | 9/2009 |
| WO | WO 2009/135846 A1 | 11/2009 |
| WO | WO 2010/032128 A1 | 3/2010 |
| WO | WO 2010/069050 A1 | 6/2010 |
| WO | WO 2010/078486 A2 | 7/2010 |
| WO | WO 2010/141505 A1 | 12/2010 |
| WO | WO 2011/009603 A1 | 1/2011 |
| WO | WO 2011/009604 A1 | 1/2011 |
| WO | WO 2011/068723 A1 | 6/2011 |
| WO | WO 2011/077451 A2 | 6/2011 |
| WO | WO 2011106416 A2 | 9/2011 |
| WO | WO 2012/007159 A2 | 1/2012 |

OTHER PUBLICATIONS

Knovel, Merck Index; Metformin, Acetominophen, and Vancomycin, Merck Sharp & Dohme Corp., copyright 2006, 2012, Download Aug. 9, 2012, Retrieved from the internet <URL: http://www.knovel.com/web/portal/basic_search/display?_EXT_KNOVEL_DISPLAY_bookid=1863>, 9 pages.

Rawlins et al., "Pharmacokinetics of paracetamol (acetaminophen) after intravenous and oral administration", Eur. J. Clin. Pharmacol., vol. 11, No. 4, pp. 283-286 (1977).

Foremost NF Fast Flo Lactose, "A spray-dried mixture of crystalline and amorphose lactose", Foremost Farms USA, 1 pg., Online Article downloaded from the site: http://www.foremostfarms.com/Commercials/pdfs/Specifications/TDS_NF_Lactose_316.pdf, Document created on Jan. 28, 2010.

Freedet et al., "pH control of nucleophilic/electrophilic oxidation", Int. J. Pharm., vol. 357, pp. 180-188 (2008).

Gammaitoni et al., "Randomized, Double-Blind, Placebo-Controled Comparison of the Analgesic Efficacy of Oxycodone 10 mg/Acetaminophen 325 mg versus Controlled-Release Oxycodone 20 mg in Postsurgical Pain," J. Clin. Pharmacol, vol. 43, pp. 296-304 (2003).

Hou et al., "Gastric retentive dosage forms: a review", Crit. Rev. Ther. Drug carr. Sys., vol. 20, No. 8, pp. 461-497 (2003).

International Search Report from related PCT Patent application No. PCT/US2009/036864 mailed Aug. 31, 2009, application now pubilshed as PCT Publication No. WO2009/114648 on Sep. 17, 2009.

International Searcn Report from PCT Patent Application No. PCT/US2010/061400 maiied Nov. 25, 2011, application now published as PCT Publication No. WO 2011/087765 on Jul. 21, 2011.

James et al., "Acetaminophen-Induced Hepatotoxicity", The American Society for Pharmacology and Experimental Therapeutics, (2003), vol. 31, No. 12, pp. 1499-1506.

Khosla, et al., "The effect of tablet size on the gastric emptying of non-disintegrating tablets", International Journal of Pharmaceutics, vol. 62, pp. R9-R11 (1990).

Khosla et al., "Gastrointestinal transit of non-disintegrating tablets in fed subjects". International Journal of Pharmaceutics, vol. 53, pp. 107-117 (1989).

Kim "Effects of drug solubility, drug loading and polymer molecular weight on drug release from polyox tablets", Drug. Dev. Ind. Pharm. vol. 24, No. 7, pp. 645-651 (1998).

Lab Basics Technical Library, Particle Size Conversion Table, Sigma-Aldrich, 3 pgs., Online Article downloaded from the site: http://www.sigmaaldrich.com/chemistry/stockroom-reagents/learning-center/technical-library/particle-size-conversion.printerview.html on Apr. 17, 2012.

Levy-Cooperman et al., "A novel extended-release formulation of oxycodone/acetaminophen with abuse deterrent properties", Painweek, 2 pgs., Online Article downloaded from the site: http://www.painweek.org/media/mediafile_attachments/06/26-pain20100131.pdf, Document created Aug. 28, 2010, Abstract Only.

Microchnitchenko et al., "Acetaminophen Toxicity", The American Society for Biochemistry and Molecular Biology, Inc., vol. 274, No. 15, pp. 10349-10355 (1999).

Mitchell et al., "Acetaminophen-induced hepatic necrosis. IV. Protective role of glutathione". j. Pharmacol. Exp. Ther., vol. 187, No. 187, No. 1, pp. 211-217 (1973).

Moes, "Gastroretentive dosage forms", Rev. Ther. Drug Carr. Sys., vol. 10, No. 2, pp. 143-195 (1995).

Moller et al., "Time to Onset of Analgesia and Analgesic Efficacy of Efferevescent Acetaminophen", J. Clin. Pharmacol., vol. 40, pp. 370-378 (2000).

Nelson and Bruschi, "Mechanisms of Acetominophen-Induced liver disease", *Drug Induced Liver Disease,* Kaplowitz et al., Ed., Marcel Dekkar, Inc. New York, NY, Chapter 13, pp. 287-325 (2003).

Nielson et al., "Analgesic efficacy of immediate and sustained release paracetamol and plasma concentration of paracetamol", Eur. J. Clin. Pharmacol, vol. 42, pp. 261-264 (1992).

Nimmo et al., "Inhibition of gastric emptying and drug absorption by narcotic analgesics", Br. J. Clin. Pharmac., vol. 2, pp. 509-513 (1975).

Oxycontin, "(Oxycodone HCI controlled-release) tablets", Description and Patient Information, Purdue Pharma, 32 pgs, Online Article downloaded from site: http://www.purduepharma.com/pi/prescription/oxycontin.pdf, Document created Aug. 17, 2010.

Percocet, "(Oxycodone and Acetaminophen Tablets, USP)", Package Insert, Endo Pharmaceuticals, 17 pgs., Online Article downloaded from the site: http://www.endo.com/File%20Library/Products/Prescribing%20Information/Percocet_pack_insert_2.pdf, Document created Jul. 11, 2011.

Polyox Water-Soluble Resins, Technical Data, "Degradation of water-soluble resins", Form 326-00027-1002AMS (2002).

Polyox Water-Soluble Resins, Technical Data, "Water-soluble resin storage stability", From 326-00044-0704MAB (2004).

Rinaldi et al., "Minireview Reactive Intermediates and the Dynamics of Glutathione Transferases", The American Society for Pharmacology and Experimental Therapeutics, vol. 30, No. 10, pp. 1053-1058 (2002).

Rumack et al., "Acetaminophen Hepatotoxicity: The First 35 Years", Clinical Toxicology, vol. 40, No. 1, pp. 3-20 (2002).

Skoglund et al., "Efficacy of paracetamol-esterified menthionine versus cysteine or methionine on paracetamol-induced hepatic GSH depletion and plasma AIAT level in mice", Biochem. Pharmacol., vol. 35, pp. 3071-3075, (1986).

Streuble et al., "Drug delivery to the upper small intensive window using gastroretentive technologies", Curr. Opin. Pharm., vol. 6, pp. 501-508 (2006).

Streuble et al., "Gastroretentive drug delivery systems", Expert Opin. Drug Del., vol. 3, No. 2, pp. 217-233 (2006).

Talukder and Fassihi, "Gastroretentive delivery systems: a mini review". Drug Development and Industrial Pharmacy, vol. 30, No. 10, pp. 1019-1028 (2004).

Tylenol *Acetominophen* "Tylenol Proffesional Product Information", McNeil Consumer Healthcare, 62 pgs., Online article downloaded from the site: http://www.tylenolprofessional.com/assets/TYL_PPI.pdf, Document created Mar. 24, 2010.

U.S. Department of Health & Human Services, FDA Drugs Safety Communication. Prescription Acetominophen Products to be Limited to 325mg per Dosage Unit, Boxed Warning Will Highlight Potential for Severe Liver Failure, 5 pgs., Online Article downloaded from the site: www.fda.gov/drugs/drugsafety/ucm239821.htm, Article Last Updated on Jan. 21, 2011.

Waterman et al., "Stabilization of pharmacueticals to oxidative degradation", Pharm. Dev. Tech., vol. 7, No. 1, pp. 1-32 (2002).

Zhang et al., "Effect of processing methods and heat treatment on the formation of wax matrix talets for sustained drug release", Pharm. Dev. Tech., vol. 6, No. 2, pp. 131-144 (2001).

Zhu et al., "Solid-state plasticization of an acrylic polymer with chlorpheniramine maleate and triethyl citrate", Int. J. Pharm., vol. 241, No. 2, pp. 301-310 (2002).

Doteuchi et al., "Pharmacological studies of oxycodone hydrochloride. 1. Antinociceptive effect and general pharmacology", Pharmacometrics, vol. 49, No. 3, pp. 257-273 (1995).

(56) References Cited

OTHER PUBLICATIONS

Meert et al., "A preclinical comparison between different opioids: antinociceptive versus adverse effects", Pharmacol. Biochem. Behavior, vol. 80, No. 2, pp. 309-326 (2005).
U.S. Appl. No. 13/360,595, filed Jan. 27, 2012, Han et al.
U.S. Appl. No. 13/473,563, filed May 16, 2012, Devarakonda et al.
U.S. Appl. No. 13/473,571, filed May 16, 2012, Devarakonda et al.
U.S. Appl. No. 13/473,578, filed May 16, 2012, Devarakonda et al.
U.S. Appl. No. 13/473,584, filed May 16, 2012, Devarakonda et al.
U.S. Appl. No. 13/473,586, filed May 16, 2012, Devarakonda et al.
Altaf et al., "Bead compacts. II: Evaluation of rapidly disintegrating nonsegregating compressed bead formulations", Drug Development and Industrial Pharmacy, vol. 25, No. 5, pp. 635-642 (1999).
Banfai et al., "Content uniformity and assay requirements in current regulations", J. Chromatogr. A., vol. 1156, No. 1-2, pp. 206-212 (2007).
Bardonnet et al., "Gastroretentive dosage forms: overview and special case of *Helicobacter pylori*", J. Controlled Rel., vol. 111, pp. 1-18 (2006).
Bartels et al., "Are recommended doses of acetaminophen hepatotoxic for recently abstinent alcoholics? A randomized trial", Clinical Toxicology, vol. 46, pp. 243-249 (2008).
Boelsterli, "Mechanisms unserlying the hepatoxicity of nonsteroidal anti-inflammatory drugs", *Drug Induced Liver Disease*, Kaplowitz et al., Ed., Marcel Dekkar, Inc. New York, NY, Chapter 15, pp. 345-375 (2003).
Bolesta et al., "Hepatotoxicity Associated with Chronic Acetaminophen Administration in Patients without Risk Factors", The Annals of Pharmacotherapy, vol. 36, pp. 331-333 (2002).
Brzeznicka et al., "Dynamics of Glutathione Levels in Liver and Indicatory Enzymes in Serum in Acetaminophen Intoxication in Mice", Polish Journal of Occupational Medicine, vol. 2, No. 1, pp. 15-22 (1989).
Corcoran et al., "Role of Glutathione in Prevention of Acetaminophen-Induced Hepatotoxicity by N-Acetyl-l-Cysteine in Vivo: Studies with N-Acetyl-D-Cysteine in Mice"; The Journal of Pharmacology and Experimental Therapeutics, vol. 238, No. 1, pp. 54-61 (1986).
Dart et al., "Acetaminophen Poisoning: an Evidence-Based Consensus Guideline for Out-of-Hospital Management", (2006), Clinical Toxicology; 44, pp. 1-18 (2006).
Davis et al., "Species Differences in Hepatic Glutathione Depletion, Covalent Binding and Hepatic Necrosis after Acetaminophen", Life Sciences, vol. 14, pp. 2099-2109 (1974).
Davis et al., "The gastrointestinal transit of a controlled release formulation of indomethacin", International Journal of Pharmaceutics, vol. 60, pp. 191-196 (1990).
Davis, "Formulation strategies for absorption windows", Drug Discovery Today, vol. 10, No. 4, pp. 249-257 (2005).
AT Ortho Pharmaceutical Corp., "P-K Liquid-Solids Blender Granulates Tablet Formulations in a Single Step, Pre-Blends, Disperses, Granulates", Industrial Engineering and Chemistry, Patterson and Kelley, Chemical and Process Equipment Division, vol. 53, No. 4, pp. 40A-41A (Apr. 1961).
Lieberman et al., editors, *Pharmaceutical Dosage Forms—Tablets.* $2^{nd}$ ed., rev. and expanded, Marcel Dekker, Inc., New York, USA, vols. 1-3, 17 pages (1989) Title pages and Tablets of Contents.
Ashford. "Gastrointestinal tract—physiology and drug absorption", *Aulton's pharmaceuticals: The design and manufacture of medicines, Third Edition,* Aulton, Ed., Churchhill Livingstone Elsevier, Elsevier Limited, Chapter 20, pp. 270-278 (2007).
Berner et al., "Case studies im swelling polymeric gastric retentive tablets", Expert Opin. Drug Deliv., vol. 3, No. 4, pp. 541-548 (2006).
Glumetza (metformin hydrochloride extended-release tablets), Highlights of Prescribing Information, 10 pages (2011).
Gralise (gabapentin), Highlights of Prescribing Information, 24 pages (2012).
Prinderre et al., "Advances in gastro retentive drug-delivery systems", Expert Opin. Drug. Deliv., vol. 8, No. 9, pp. 1189-1203 (2011).

* cited by examiner

GASTRIC RETENTIVE EXTENDED-RELEASE DOSAGE FORMS COMPRISING COMBINATIONS OF A NON-OPIOID ANALGESIC AND AN OPIOID ANALGESIC

This application is a continuation of U.S. application Ser. No. 12/644,444, now issued U.S. Pat. No. 8,372,432, filed Dec. 22, 2009 which is a continuation-in-part of U.S. application Ser. No. 12/402,477, now issued U.S. Pat. No. 8,377,453, filed Mar. 11, 2009, which claims the benefit of U.S. Provisional Application No. 61/035,696 filed Mar. 11, 2008, all of which are incorporated herein by reference in their entirety.

TECHNICAL FIELD

Compositions and methods are described for relief or treatment of existing or anticipated pain. In some embodiments, gastric retentive ("GR®") dosage forms comprise acetaminophen (APAP) in combination with an opioid analgesic and are administered to a person suffering from, diagnosed with or at risk of experiencing pain. The dosage forms when administered to a mammal, typically provide about 3 hours to about 12 hours of delivery of one or both of the drugs to the upper gastrointestinal ("GI") of the mammal. The present disclosure also relates to a method for treating pain by providing the gastric retentive dosage forms, and to methods of making the gastric retentive dosage forms.

BACKGROUND

It is often desirable to administer to a mammalian subject an opioid analgesic combined with a non-opioid analgesic agent, for example, acetaminophen (APAP). Such combination formulations provide the advantage of additive analgesic effects with a lower dose of opioid, and hence a resulting lower incidence of side effects and the ability to treat a broader spectrum of pain or pain states due to different mechanisms of actions.

Such is the case for combinations of acetaminophen or aspirin with opioids, such as oxycodone (Percocet® and Percodan®, respectively), or hydrocodone (Vicodin® and Lortab®, respectively) or acetaminophen with codeine (Tylenol® with codeine). However, these currently marketed drug products deliver the combination drugs as an immediate release product. Accordingly, the drug product has to be administered quite frequently and at least every 4 to 6. Currently, extended-release oral dosage forms for delivery of the above active ingredients are only available for delivery of a single active pharmaceutical ingredient. For example, Tylenol® Extended Release for Arthritis provides a dosage of 650 milligrams acetaminophen to be administered every 8 hours. OxyContin® is formulated to provide controlled release of oxycodone hydrochloride via twice-daily administration.

When treating a mammalian subject suffering from or diagnosed with a chronic or acute pain state, it is highly desirable to maintain and achieve analgesia continuously. Immediate release formulations of the appropriate therapeutic agents require frequent and/or continuous dosing throughout the day (or night) for continuous pain relief. This is often inconvenient and difficult to maintain regularly dosing and frequently leads to poor patient compliance, potentially resulting in a dose being taken after pain breaks through again, causing unnecessary pain and suffering.

Hence, it would be desirable and beneficial to provide extended release delivery of a drug product that comprises both an opioid and a non-opioid analgesic such as acetaminophen. Such a dosage form would reduce the frequency of administration to a subject while sustaining plasma drug levels and analgesic effects throughout the day (or night). Such an extended release dosage form would eliminate the need to dose frequently to maintain analgesia, which is often inconvenient and difficult to maintain regularly, with the result that the next dose is taken after the pain breaks through again, causing unnecessary pain and suffering. Additionally, such a dosage form would increase patient compliance while minimizing adverse effects or events.

Gastric retentive dosage forms have demonstrated success in providing extended delivery of active ingredients. Drugs that are delivered from a gastric retained dosage form continuously bathe the stomach, duodenum and upper part of the small intestine for many hours. Release of the drug from the dosage form upstream of absorption sites provides extended and controlled exposure of the absorption sites to the released drug, thus increasing bioavailability. Acetaminophen demonstrates reduced bioavailability when administered rectally (about 35-50%) as compared to oral administration (about 60-70%). The increasingly dry environment of the colon is unfavorable for absorption. Accordingly, a gastric retentive extended release dosage form would provide several significant advantages as it would obviate the bioavailability reduction seen in the colon with non-gastric retentive extended release dosage forms.

Although gastric retentive dosage forms containing a drug dispersed in a swellable polymer matrix have been previously described, new challenges arise when formulating dosage forms that can provide the therapeutically effective delivery of a combination of drugs, which include, for example, acetaminophen and an opioid. Firstly, these two active agents have very different solubilities. Acetaminophen is a sparingly soluble drug in water, having a solubility of about 1-5 milligrams/milliliter (mg/ml) in water at 22° C. In contrast, opioids, which are formulated as acid salts in drug products, are highly soluble in water. For example, oxycodone HCl (100 to 167 (mg/ml), hydrocodone bitartrate (62.5 mg/ml), and codeine phosphate (400 to 435 mg/ml). Such disparities in solubility should be taken into account when formulating a dosage form that releases the two active agents at rates proportional to each other. Secondly, opioids are known to inhibit gastric motility. Such inhibition can negatively impact the erosion rate of a gastric retentive dosage form as needed for the desired drug release profile. Finally, acetaminophen is known to be difficult for the production of solid oral dosage forms. It can be particularly difficult to produce a tablet having acetaminophen because acetaminophen powder does not compress easily to form a stable tablet. Moreover, preparation of tablets having necessary dosage levels requires a relatively high weight percent of the drug. As a result, production of a useful tablet size allows only low amounts of excipients. This contributes to the difficulties involved in producing a tablet that relies on the use of a swellable polymer for extended release.

The present disclosure meets these challenges and needs, among others.

SUMMARY

The present disclosure provides, among other aspects, gastric retentive dosage forms for oral administration to a subject, such as a human patient, for relief from a pain state. The dosage form in some embodiments is a gastric retentive dosage form that contains a first dose of at least one drug as an extended release ("ER") portion, and a second dose of at least one drug as an immediate release ("IR") component. The dosage forms typically contain a therapeutically effective amount of acetaminophen (APAP) and a therapeutically effective amount of an opioid or opioid-like analgesic.

In one aspect, the ER portion of the dosage form comprises an opioid and acetaminophen containing a first dose of the opioid and a first dose of acetaminophen. In another aspect, the ER portion of the dosage form comprises the first dose of opioid and the first dose of acetaminophen dispersed in a polymer matrix comprising at least one hydrophilic polymer. Upon administration, the polymer matrix is able to swell upon imbibition of fluid to a size sufficient such that the ER portion of the dosage form is retained in a stomach of a subject in a fed mode and the first dose of opioid and the first dose of acetaminophen are released over an extended period of time. The ER portion may alternatively be referred to herein as the gastric retentive or "GR" portion.

In another aspect, the dosage form releases the acetaminophen through erosion of the polymer matrix and the opioid is released at a rate proportional to the release of the acetaminophen. In another embodiment, the dosage form releases the acetaminophen through both erosion and diffusion. In additional embodiments, the rate of release of the opioid is about 2% to about 10%, or about 4% to about 8%, or about 5% or about 7% of the rate of release of the acetaminophen, over a period of release from between about 2 to about 10 hours, or about 4 to about 6 hours, or about 4 to about 8 hours.

In one embodiment, the opioid or opioid-like analgesic is tramadol, hydrocodone, oxycodone, hydromorphone or codeine.

In one embodiment, the ER portion of the dosage form comprises a first dose of acetaminophen of about 100 milligrams (mg) to about 600 mg and is delivered over an extended period of time. In another embodiment, the first dose of acetaminophen is about 200 mg to about 400 mg, or about 275 mg to about 325 mg. In yet another embodiment, the first dose of acetaminophen is about 270 mg, 275 mg, 280 mg, 285 mg, 290 mg, 295 mg, 300 mg, 304 mg, 305 mg, 310 mg, 315 mg, 320 mg, 325 mg or 330 mg. In another aspect, the ER portion of the dosage form comprises a first dose of acetaminophen that is approximately 25 weight percent (wt %), 30 wt %, 35 wt %, 38 wt %, 39 wt %, 40 wt %, 41 wt %, 42 wt %, 43 wt %, 44 wt %, 45 wt %, 47 wt %, 50 wt %, 55 wt %, 60 wt %, 65 wt % or 70 wt % of the total weight of the dosage form.

In one embodiment, the ER portion of the dosage form comprises a first dose of opioid of about 10 mg to about 100 mg. In another embodiment, the first dose of opioid is about 14 mg to about 25 mg. In another embodiment, the first dose of opioid is about 15 mg to about 50 mg. In an additional embodiment, the first dose of opioid is about 16 mg to about 30 mg. In another embodiment, the first dose of opioid is about 16.5 mg to about 20 mg. In yet another embodiment, the first dose of opioid is about 15.0 mg, 15.5 mg, 16.0 mg, 16.5 mg, 17.0 mg, 17.5 mg, 18.0 mg, 18.5 mg, 19.0 mg, 19.5 mg, or 20.0 mg. In yet another embodiment, the ER portion of the polymer matrix comprises a first dose of opioid that is approximately 1.0 wt %, 1.5 wt %, 2.0 wt %, 2.2 wt %, 2.5 wt %, 2.6 wt %, 2.7 wt %, 2.8 wt %, 3.0 wt %, 3.2 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 M %, 9.5 wt % or 10 wt % of the total weight of the ER portion of the dosage form.

In another embodiment, the weight percent of acetaminophen is typically between about 10 to 20 times, more typically between 14 to 17 times the weight percent of opioid in the ER portion of the dosage form.

In one embodiment, the at least one polymer is a polyalkylene oxide. In another aspect, the polyalkylene oxide is poly(ethylene) oxide. In a further embodiment, the poly(ethylene) oxide has an approximate molecular weight between 500,000 Daltons (Da) to about 10,000,000 Da or about 900,000 Da to about 7,000,000 Da. In yet a further embodiment, the poly(ethylene) oxide has a molecular weight of approximately 600,000 Da, 900,000 Da, 1,000,000 Da, 2,000,000 Da, 4,000,000 Da, 5,000,000 Da, 7,000,000 Da, 9,000,000 Da and 10,000,000 Da.

In another embodiment, the polymer is present in the ER portion of the dosage form from about 15 wt % to about 70 wt %, or about 20 wt % to about 60 wt %, or about 25 wt % to about 55 wt % of the total wt % of the dosage form of the ER portion. In another embodiment, the polymer is present in the ER portion of the dosage form in an amount ranging from about 30 wt % to about 50%, or about 35 wt % to about 45 wt %. In yet another embodiment, the polymer is present in the ER portion of the dosage form in an amount equal to approximately 30 wt %, 35 wt %, 40 wt %, 45 wt %, 50 wt %, 55 wt % or 60 wt % of the ER portion.

In one embodiment, the ER portion of the dosage form further comprises a binder. In another embodiment, the binder is selected from the group consisting of polyvinylpryolidone (povidone), a hydroxyalkylcellulose such as hydroxypropylcellulose, starches, pregelatinized starches, gelatin, cellulose, methylcellulose, sodium carboxymethylcellulose, ethylcellulose, polyacrylamides, polyvinyloxoazolidone, polyvinylalcohols, C12-C18 fatty acid alcohols, polyethylene glycol, polyols. In another embodiment, the ER portion of the dosage form comprises a binder that is present in an amount that is about 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt % or 8.0 wt % of the ER portion.

In one embodiment, the ER portion of the dosage form further comprises a filler. In another embodiment, the filler is selected from microcrystalline cellulose (MCC), dibasic calcium phosphate, tribasic calcium phosphate, magnesium carbonate, magnesium oxide, calcium silicate, polyvinylpirrolydone, dibasic calcium sulfate, tribasic calcium sulfate, starch, calcium carbonate, magnesium carbonate, carbohydrates, modified starches, lactose, sucrose, mannitol, sorbitol, and inorganic compounds. In another embodiment, the ER portion of the dosage form comprises a filler that is present in an amount that is about 1.0 wt %, 1.5 wt %, 2.0 wt %, 2.5 wt %, 3.0 wt %, 3.5 wt %, 4.0 wt %, 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt % or 10 wt % of the ER portion of the dosage form.

In one embodiment, the ER portion of the dosage form further comprises a lubricant. In another embodiment, the lubricant is magnesium stearate. In another embodiment, the ER portion of the dosage form comprises a lubricant that is present in an amount that is about 0.1 wt %, 0.5 wt %, 0.75 wt %, 1.0 wt %, 1.5 wt %, 1.75 wt %, 1.80 wt %, 1.85 wt %, 1.90 wt % or 2.0 wt % of the ER portion.

In one embodiment, the ER portion of the dosage form comprises an anti-oxidant which is ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, or propylgallate. In another embodiment, the antioxidant is present in the ER portion of the dosage form at a wt % ranging from about 0.10 wt % to about 0.20 wt %, or from about 0.05 wt % to about 0.30 wt %.

In yet another embodiment, the antioxidant is present in the ER portion of the dosage form at a wt % of about 0.01 wt %, 0.05 wt %, 0.10 wt %, 0.15 wt %, 0.20 wt %, 0.25 wt %, 0.35 wt %, 0.50 wt %, 0.75 wt %, 1.00 wt %, 2.00 wt %, 3.00 wt % or 4.00 wt % of the ER portion.

In one embodiment, the ER portion of the dosage form comprises a chelating agent. In another embodiment, the chelating agent is selected from ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclododecane-N,N',N'',N'''-tetraacetic acid, 1,4,7,10-tetraazacyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'', N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In a further embodiment, the chelating agent is the sodium salt of EDTA. In yet another embodiment, the ER portion of the dosage form comprises a chelating agent which is present in an amount that is about 0.01 wt % to about 0.10 wt % or about 0.02 to about 0.08 wt % of the ER portion. In yet another embodiment, the ER portion of the dosage form comprises a chelating agent which is present in an amount which is about 0.01 wt %, 0.02 wt %, 0.03 wt %, 0.04 wt %, 0.05 wt %, 0.06 wt %, 0.07 wt %, 0.08 wt %, 0.09 wt % or 0.10 wt %.

In one embodiment, the ER portion of the dosage form comprises a color agent. In another embodiment, the color agent is present in an amount that is about 2.0 wt % to about 5.0 wt % of the ER portion of the dosage form. In yet another embodiment, the color agent is present in an amount that is about 1.0 wt %, 1.5 wt %, 2.0 wt %, 2.5 wt %, 3.0 wt %, 3.5 wt %, 4.0 wt %, 4.5 wt %, or 5.0 wt % of the ER portion.

In another embodiment, the ER portion of the dosage form comprises particles of acetaminophen admixed with the opioid and the polymer.

In one embodiment, the ER portion of the dosage form comprises particles wherein the particles have an average particle size greater than about 20 microns and less than about 2000 microns, greater than about 50 microns and less than about 1500 microns, greater than about 100 microns and less than about 1000 microns, greater than about 150 microns and less than about 1000 microns, or greater than about 200 microns and less than about 2000 microns.

In one embodiment, the ER portion of the dosage form comprises particles wherein at least about 50% of the particles are greater than about 250 microns in size. In another embodiment, about 20% to about 30% of the particles are greater than about 150 microns and less than about 250 microns.

In another embodiment, after oral administration to a subject, the opioid is released from ER portion of the dosage form at a rate proportional to release of the acetaminophen for a period of at least about 4 hours (h). In another embodiment, the proportional rate of release occurs for a period of at least about 5 h, 6 h, 7 h, or 8 h. In yet another embodiment, the first dose of opioid is released from the ER portion of the dosage form at a rate proportional to release of the first dose of acetaminophen for a period of about 4 h to about 8 h. In another embodiment, the proportional rate of release occurs over a period of about 5 h to about 6 h. In another embodiment, the ER portion of the dosage form comprises particles of acetaminophen admixed with the opioid and the polymer.

In some embodiments, the ER portion of the dosage form swells upon administration to a size that is about 110% to about 160%, or about 120% to about 150%, or about 125% to about 145%, or about 130% to about 145% of the size of the dosage form within 30 minutes of administration. In other embodiments, the ER portion of the dosage form swells to a size that is approximately 130% of the size of the dosage form within 30 minutes of administration.

In another embodiment, upon administering of the dosage form to a subject, the dosage form provides at least about 4 hours to about 12 hours of drug delivery to the upper gastrointestinal tract, which includes the stomach and the small intestine. In another embodiment, the dosage form provides at least 6 hours of drug delivery to the upper gastrointestinal tract. In yet a further embodiment, the dosage form provides at least 8 hours of drug delivery to the upper gastrointestinal tract. In yet a further embodiment, the dosage form provides at least 9 hours, 10 hours, 11 hours or 12 hours of drug delivery to the upper gastrointestinal tract.

In some embodiments, the dosage form provides a dissolution profile wherein for each of the first dose of acetaminophen and the first dose of the opioid, between about 40% to about 50% of the first dose remains in the dosage form between about 1 and 2 hours after administration. In one embodiment, not more than 50% of the first dose of acetaminophen and first dose of opioid is released within about the first hour. In a further embodiment, not more than 45% or not more than 40% of the first dose of acetaminophen and first dose of opioid is released within about the first hour. In another embodiment, not more than 85% of the first dose of acetaminophen and first dose of opioid is released within about 4 hours. In another embodiment, not less than 50% is released after about 6 hours. In yet another embodiment, not less than 60% is released after about 6 hours.

In one embodiment, the dosage form further comprises an IR portion. The IR portion of the dosage form typically comprises a second dose of an opioid and a second dose of acetaminophen. In another embodiment, the opioid and the acetaminophen are dispersed in the IR portion of the dosage form. In yet another embodiment, a dosage form comprising an IR portion in contact with an ER portion is provided.

In one embodiment, the IR portion of the dosage form comprises about 50 mg to about 900 mg, about 75 mg to about 700 mg, about 100 mg to about 600 mg, or about 150 mg to about 250 mg of acetaminophen. In yet another embodiment, the IR portion of the dosage form comprises about 200 mg to about 400 mg of acetaminophen. In yet another embodiment, the IR portion of the dosage form comprises about 180 mg, 190 mg, 195 mg, 200 mg, 205 mg, 210 mg, 215 mg, 220 mg, 225 mg, 230 mg or 235 mg of acetaminophen.

In another embodiment, the IR portion of the dosage form comprises about 5 mg to about 60 mg, or about 10 mg to about 40 mg, or about 15 mg to about 20 mg of the opioid. In yet another embodiment, the IR portion of the dosage form comprises about 14.0 mg, 14.5 mg, 15.0 mg, 15.5 mg, 16.0 mg, 16.5 mg, or 17.0 mg of the opioid.

In another embodiment, the amount of acetaminophen in the IR portion is typically between about 10 to about 20, more typically between about 12 to about 16 times the amount of opioid in the IR portion. In another embodiment, the ratio of acetaminophen to opioid in the IR portion is about 10, 11, 12, 13, 14, 15, 16, 17, 18, 19 or 20.

In yet another embodiment, the IR portion of the dosage form further comprises a binder. In some embodiments, the binder is selected from the group consisting of polyvinylpryolidone (povidone), hydroxypropylmethylcellulose (HPMC), polyvinyl alcohol, hydroxyethylcellulose, hydroxypropylcellulose, methylcellulose, methacrylic acid copolymers, ethyacrylate-methylmethacrylate copolymers, guar gum, arabic gum, xanthan gum, gelatine, pectin and mixtures thereof. In another embodiment, the binder is present in the IR portion of the dosage form in an amount that is about 4.5 wt %, 5.0 wt %, 5.5 wt %, 6.0 wt %, 6.5 wt %, 7.0 wt %, 7.5 wt %, 8.0 wt %, 8.5 wt %, 9.0 wt %, 9.5 wt % or 10.0 wt % of the IR portion.

In one embodiment, the IR portion of the dosage form comprises an anti-oxidant which is ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, or propylgallate. In another embodiment, the antioxidant is present in the IR portion of the dosage form at a wt % ranging from about 0.10 wt % to about 0.40 wt %, or from about 0.05 wt % to about 0.35 wt %. In yet another embodiment, the antioxidant is present in the IR portion of the dosage form at a wt % of about 0.01 wt %, 0.05 wt %, 0.10 wt %, 0.15 wt %, 0.20 wt %, 0.25 wt %, 0.30 wt %, 0.35 wt %, 0.50 wt %, 0.75 wt %, 1.00 wt %, 2.00 wt %, 3.00 wt % or 4.00 wt % of the IR portion.

In one embodiment, the IR portion of the dosage form comprises a chelating agent. In another embodiment, the chelating agent is selected from ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. In yet another embodiment, the IR portion of the dosage form comprises a chelating agent which is present in an amount that is about 0.01 wt % to about 0.10 wt % or about 0.02 to about 0.08 wt % of the IR portion. In yet another embodiment, the IR portion of the dosage form comprises a chelating agent which is present in an amount which is about 0.01 wt %, 0.02 wt %, 0.03 wt %, 0.04 wt %, 0.05 wt %, 0.06 wt %, 0.07 wt %, 0.08 wt %, 0.09 wt % or 0.10 wt %.

In one embodiment, the IR portion of the dosage form comprises particles of acetaminophen granulated with the opioid and the binder.

In one embodiment, the IR portion of the dosage form comprises particles wherein the particles have an average particle size greater than about 20 microns and less than about 2000 microns, greater than about 50 microns and less than about 1500 microns, greater than about 100 microns and less than about 1000 microns, greater than about 150 microns and less than about 1000 microns, or greater than about 200 microns and less than about 2000 microns.

In one embodiment, the ER portion of the dosage form comprises particles wherein at least about 50% of the particles are greater than about 250 microns in size. In another embodiment, about 20% to about 30% of the particles are greater than about 150 microns and less than about 250 microns.

In one embodiment, the IR portion of the dosage form comprises particles, wherein at least 30% of the particles have a size greater than 250 microns (µ).

In one embodiment, the dosage form is a pharmaceutical tablet, such as a gastric retentive tablet for the extended release of the opioid and the acetaminophen. In another embodiment, the tablet is a monolithic tablet comprising an ER portion. In another embodiment, the tablet is a monolithic tablet comprising an ER portion and an IR portion. In another embodiment, the tablet is a bilayer tablet, comprising an ER portion and an IR portion. The bilayer tablet is typically a monolithic tablet. In another embodiment, the dosage form is a capsule comprising an ER portion. In another embodiment, the dosage form is a capsule comprising ER portion and an IR portion.

In one embodiment, the bilayer tablet has a friability of no greater than about 0.1%, 0.2% 0.3%, 0.4%, 0.5%, 0.7% or 1.0%. In another embodiment, the bilayer tablet has a friability of greater than 0 but less that about 1.0%, greater than 0 but less than about 0.5%, greater than 0 but less than about 0.3%, or greater than 0 but less than about 0.2%.

In one embodiment, the bilayer tablet has a hardness of at least about 10 kilopond (also known as kilopons) (kp). In some embodiments, the tablet has a hardness of about 9 kp to about 25 kp, or about 12 kp to about 20 kp. In further embodiments, the tablet has a hardness of about 11 kp, 12 kp, 13 kp, 14 kp, 15 kp, or 16 kp.

In one embodiment, the tablets have a content uniformity of from about 85 to about 115 percent by weight or from about 90 to about 110 percent by weight, or from about 95 to about 105 percent by weight. In other embodiments, the content uniformity has a relative standard deviation (RSD) equal to or less than about 3.5%, 3.0%, 2.5%, 2.0%, 1.5%, 1.0% or 0.5%.

In one embodiment, the dosage form comprises an opioid or an opioid-like compound chosen from: adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, and pharmaceutical salts of any of the foregoing.

In one embodiment, acetaminophen can be present in the dosage form in an amount ranging from about 100 milligrams (mg) to about 1300 mg.

In another embodiment, acetaminophen is present in the dosage form at an amount of about 150 mg, 175 mg, 200 mg, 225 mg, 250 mg, 275 mg, 300 mg, 325 mg, 350 mg, 400 mg, 425 mg, 450 mg, 500 mg, 525 mg, 530 mg, 535 mg, 540 mg, 545 mg, 550 mg, 600 mg, 650 mg or about 700 mg.

In some embodiments, an opioid is present in the dosage form at an amount of about 5 mg, 7.5 mg, 10 mg, 12 mg, 15 mg, 20 mg, 22.5 mg, 25 mg, 30 mg, 32 mg, 34 mg, 35 mg, 37 mg, 40 mg, 50 mg, 60 mg, 70 mg or higher. In one embodiment, wherein the opioid is tramadol, an amount of about 5 mg to about 40 mg, about 10 mg to about 30 mg, or about 15 mg to about 20 mg may be employed. In another embodiment, wherein the opioid is codeine, an amount of about 50 mg to about 300 mg, or about 75 mg to about 200 mg, or about 120 mg to about 180 mg may be employed. In yet another embodiment, wherein the opioid is oxycodone, an amount of 2 mg to about 100 mg, 5 mg to about 75 mg, about 5 mg to about 40 mg, about 10 mg to about 30 mg, or about 15 mg may be employed. In yet another embodiment, wherein the opioid is hydrocodone, an amount of 2 mg to about 80 mg, 5 mg to about 40 mg, about 10 mg to about 30 mg, or about 15 to about 20 mg may be employed.

In another aspect, a pharmaceutical or gastric retentive oral dosage form comprising acetaminophen and an opioid, wherein the formulation is administered to a mammal once in a 24 hour period (q.d. or once-daily), two times in a 24 hour period (b.i.d. or twice-daily) or three times in a 24 hour period (t.i.d. or three times daily) is provided.

Also provided, is a method of making a pharmaceutical or gastric retentive dosage form comprising a first dose of an opioid, a first dose of acetaminophen dispersed in an ER polymer matrix comprised of a polymer that swells upon imbibition of fluid to a size sufficient for gastric retention in the upper gastrointestinal tract in a fed mode.

In one embodiment, the method comprises wet granulation of a first mixture that comprises an opioid, acetaminophen and a binder to produce a first granulation mixture. In another embodiment, the wet granulating comprises spraying a solution of the binder and the opioid dissolved in water onto acetaminophen particles. In a further embodiment, the particles of the first granulation mixture are blended with a polymer and one or more excipients to form an ER portion of a dosage form.

In one embodiment, the one or more excipients blended with the first granulation mixture are chosen from among a filler, a lubricant and a color agent.

In one embodiment, the wet granulation comprises making a solution containing an opioid and a binder and spraying the solution onto the acetaminophen particles in a fluid bed granulator.

In a further embodiment, the method comprises compressing the ER portion of the dosage form into a tablet.

In one embodiment, the wet granulation of the ER portion of the dosage form produces particles with a bulk density ranging from about 0.30 to 0.40 grams/milliliter (g/ml). In other aspects, the wet granulation produces particles with a tap density ranging from about 0.35 g/ml to about 0.45 g/ml. In other embodiments, the wet granulation produces particles, wherein at least about 50% of the particles have a size greater than 250μ. In still other embodiments, the wet granulation produces particles wherein about 20% to about 30% of the particles have a size greater than about 150μ and less than about 250μ.

In one embodiment, the method of making a pharmaceutical and/or gastric retentive oral dosage form comprising acetaminophen and an opioid further comprises wet granulating a second mixture comprising the acetaminophen, the opioid, and the binder to form a second granulation mixture. In a further embodiment, the second granulation mixture is blended with one or more excipients to produce an IR portion of the dosage form. In yet a further embodiment, the IR portion is compressed with the ER portion of the dosage form to produce a bilayer tablet.

In further embodiments, wet granulating the second mixture is achieved by fluid bed granulation. In other embodiments, wet granulating the second mixture is achieved by a high shear granulation method.

In an alternative embodiment, the method of making a pharmaceutical and/or gastric retentive oral dosage form comprising acetaminophen and an opioid comprises using a high-shear fluid bed granulator to prepare a first granulation mixture which comprises an opioid, a filler, and a first binder. In one embodiment, the first granulation mixture further comprises an antioxidant. In yet another embodiment, the first granulation mixture further comprises a metal ion chelator. In another embodiment, the method further comprises drying the first granulation mixture. In yet another embodiment, the method further comprises using a fluid-bed granulator to prepare a second granulation mixture comprising the first granulation mixture and acetaminophen. In yet another embodiment, the method further comprises blending the second granulation mixture with a hydrophilic polymer and one or more excipients to form an extended release portion. In yet another embodiment, the method further comprises compressing the extended release portion of the dosage form to form a monolithic tablet.

In one embodiment, the method of making a pharmaceutical and/or gastric retentive oral dosage comprises using a fluid-bed granulator to prepare a third granulation mixture which comprises the first granulation mixture, acetaminophen and a binder. In another embodiment, the method further comprises blending the third granulation mixture with a lubricant to form an immediate release portion. In yet another embodiment, the method further comprises compressing the extended release portion and the immediate release portion to for a bilayer tablet.

Also provided is a method of treating pain in a subject in need of such treatment comprising administering a therapeutic effective amount of any of the describe dosage forms or pharmaceutical formulations herein.

In one embodiment, a gastric retained dosage form comprising acetaminophen, an opioid and a swellable polymer is administered to a subject suffering from or diagnosed with a pain state. In other embodiments, the subject is suffering from chronic pain. In yet another embodiment, the subject is suffering from acute pain. In yet other embodiments, the subject is suffering from both chronic and acute pain.

In one embodiment, a gastric retained dosage form is administered to a subject in a fed mode. In another embodiment, the dosage form is administered with a meal to a subject once in a 24 hour period. In other embodiments, the dosage form is administered with a meal to the subject twice in a 24 hour period. In some embodiments, the dosage form is administered with a meal to the subject three times in a 24 hour period.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment or aspect. Additional aspects and embodiments are set forth in the following description and claims, particularly when considered in conjunction with the accompanying examples and drawings.

DETAILED DESCRIPTION

Figure 1:
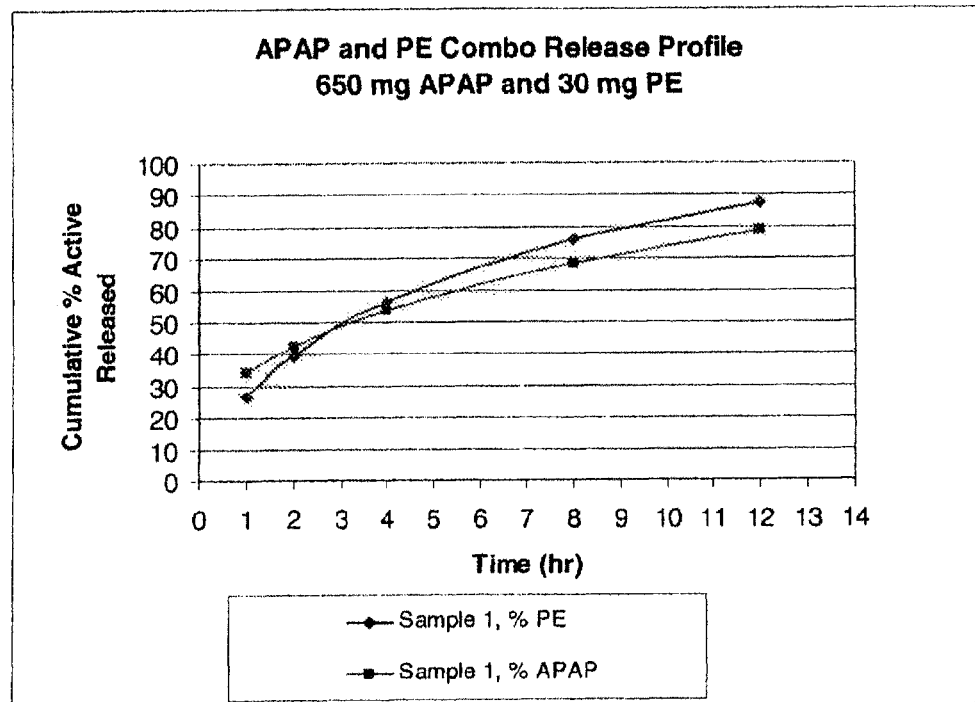
FIG. 1 is a graphical representation of the dissolution profile of a 960 mg tablet containing 650 mg acetaminophen, 30 mg phenylephrine, and 24.28 wt % POLYOX® PEO N-60K.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art.

All publications, patents and patent applications cited herein, whether supra or infra, are hereby incorporated by reference in their entirety.

I. Definitions

It must be noted that, as used in this specification, the singular forms "a," "an," and "the" include plural referents unless the context clearly dictates otherwise.

The term "about," particularly in reference to a given quantity, is meant to encompass deviations of plus or minus five percent.

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, glucepate and lactobionate salts. Similarly salts containing pharmaceutically acceptable cations include, but are not limited to, sodium, potassium, calcium, aluminum, lithium, and ammonium (including substituted ammonium).

"Optional" or "optionally" means that the subsequently described element, component or circumstance may or may not occur, so that the description includes instances where the element, component, or circumstance occurs and instances where it does not.

The terms "subject," "individual" or "patient" are used interchangeably herein and refer to a vertebrate, preferably a mammal. Mammals include, but are not limited to, humans.

The term "drug" or "active agent" is used herein to refer to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The term "sparingly soluble," as used herein, refers to a drug having a solubility (measured in water at 37° C.) in the range of about 0.001% to about 2% by weight, more preferably about 0.001% to about 0.5% by weight. The term "soluble," as used herein, refers to a drug having a solubility (measured in water at 37° C.) in the range of about 2% to about 10% by weight, more preferably about 2% to about 5% by weight.

The term "fed mode," as used herein, refers to a state which is typically induced in a patient by the presence of food in the stomach, the food giving rise to two signals, one that is said to stem from stomach distension and the other a chemical signal based on food in the stomach. It has been determined that once the fed mode has been induced, larger particles are retained in the stomach for a longer period of time than smaller particles. Thus, the fed mode is typically induced in a patient by the presence of food in the stomach.

Administration of a dosage form "with a meal," as used herein, refers to administration before, during or after a meal, and more particularly refers to administration of a dosage form about 1, 2, 3, 4, 5, 10, 15 minutes before commencement of a meal, during the meal, or about 1, 2, 3, 4, 5, 10, 15 minutes after completion of a meal.

A drug "release rate," as used herein, refers to the quantity of drug released from a dosage form or pharmaceutical composition per unit time, e.g., milligrams of drug released per hour (mg/hr). Drug release rates for drug dosage forms are typically measured as an in vitro rate of dissolution, i.e., a quantity of drug released from the dosage form or pharmaceutical composition per unit time measured under appropriate conditions and in a suitable fluid. The specific results of dissolution tests claimed herein are performed on dosage forms or pharmaceutical compositions in a USP Type II apparatus and immersed in 900 ml of simulated intestinal fluid (SIF) at pH 6.8 and equilibrated in a constant temperature water bath at 37° C. Suitable aliquots of the release rate solutions are tested to determine the amount of drug released from the dosage form or pharmaceutical composition. For example, the drug can be assayed or injected into a chromatographic system to quantify the amounts of drug released during the testing intervals.

The term "swellable polymer," as used herein, refers to a polymer that will swell in the presence of a fluid. It is understood that a given polymer may or may not swell when present in a defined drug formulation. Accordingly, the term "swellable polymer" defines a structural feature of a polymer which is dependent upon the composition in which the polymer is formulated. Whether or not a polymer swells in the presence of fluid will depend upon a variety of factors, including the specific type of polymer and the percentage of that polymer in a particular formulation. For example, the term "polyethylene oxide," or "PEO" refers to a polyethylene oxide polymer that has a wide range of molecular weights. PEO is a linear polymer of unsubstituted ethylene oxide and has a wide range of viscosity-average molecular weights. Examples of commercially available PEOs and their approximate molecular weights are: POLYOX® NF, grade WSR coagulant, molecular weight 5 million, POLYOX® grade WSR 301, molecular weight 4 million, POLYOX® grade WSR 303, molecular weight 7 million, and POLYOX® grade WSR N-60K, molecular weight 2 million. It will be understood by a person with ordinary skill in the art that an oral dosage form which comprises a swellable polymer will swell upon imbibition of water or fluid from gastric fluid The term "friability," as used herein, refers to the ease with which a tablet will break or fracture. The test for friability is a standard test known to one skilled in the art. Friability is measured under standardized conditions by weighing out a certain number of tablets (generally 20 tablets or less), placing them in a rotating Plexiglas drum in which they are lifted during replicate revolutions by a radial lever, and then dropped approximately 8 inches. After replicate revolutions (typically 100 revolutions at 25 rpm), the tablets are reweighed and the percentage of formulation abraded or chipped is calculated. The friability of the tablets, of the present invention, is preferably in the range of about 0% to 3%, and values about 1%, or less, are considered acceptable for most drug and food tablet contexts. Friability which approaches 0% is particularly preferred.

The term "tap density" or "tapped density," as used herein, refers to a measure of the density of a powder. The tapped density of a pharmaceutical powder is determined using a tapped density tester, which is set to tap the powder at a fixed impact force and frequency. Tapped density by the USP method is determined by a linear progression of the number of taps.

The term "bulk density," as used herein, refers to a property of powders and is defined as the mass of many particles of the material divided by the total volume they occupy. The total volume includes particle volume, inter-particle void volume and internal pore volume.

The term "capping," as used herein, refers to the partial or complete separation of top or bottom crowns of the tablet main body. For multilayer tablets, capping refers to separation of a portion of an individual layer within the multilayer tablet. Unintended separation of layers within a multilayer tablet prior to administration is referred to herein as "splitting."

The term "content uniformity," as used herein refers to the testing of compressed tablets to provide an assessment of how uniformly the micronized or submicron active ingredient is dispersed in the powder mixture. Content uniformity is measured by use of USP Method (General Chapters, Uniformity of Dosage Forms), unless otherwise indicated. A plurality refers to five, ten or more tablet compositions.

II. Gastric Retentive Extended Release Dosage Form

It has been surprisingly discovered that a pharmaceutically acceptable gastric retentive dosage form can be formulated to provide release in the stomach of a combination of a sparingly soluble drug and a highly soluble drug at rates proportional to one another over an extended period of time. Described herein is a pharmaceutically acceptable dosage form for the treatment of pain in a subject, comprising an opioid and acetaminophen dispersed in a polymer matrix that, upon oral administration, swells dimensionally unrestrained, with the imbibition of fluid to a size sufficient for gastric retention in a stomach of a subject in a fed mode. In the presently described dosage form, acetaminophen is released from the dosage form through erosion and an opioid also present in the dosage form is released at a rate proportional to that of the acetaminophen. This proportional rate of release may occur over a period of 3, 4, 5, 6, 7, 8, 9, 10, 11, 12 hours or more.

Gastric retentive dosage forms described herein typically contain at least one hydrophilic polymer in a water-swellable polymer matrix having at least one drug dispersed therein. The polymer matrix, wherein the at least one drug is dispersed, absorbs water, causing the matrix to swell, which in turn promotes retention of the dosage form in the upper gastrointestinal tract (GI) of a subject. In addition, the matrices become slippery, which provides resistance to peristalsis and further promotes gastric retention.

The imbibition of water and subsequent swelling also allows drugs to diffuse out of the matrix, to be released from the matrix as a result of physical erosion, i.e., degradation, or a combination of the two. Whether the drugs are released via diffusion or erosion depends, in part, on the solubility of the drug in the relevant environment Thus, successful formulation of effective oral pharmaceutical dosage forms may be highly dependent upon the solubility of the incorporated drugs. For example, compositions in a tablet may differ when the tablet contains a high solubility drug as compared to when the tablet contains a low solubility drug.

With the dosage forms described herein, the rate at which the drugs are released by the gastric retentive dosage form into the gastrointestinal tract is largely dependent on the rate at and the degree to which the polymer matrix swells and. The polymer used in the dosage forms of the present invention should not release the drug at too rapid a rate so as to result in a drug overdose or rapid passage into and through the gastrointestinal tract, nor should the polymer release drug too slowly to achieve the desired biological effect. Thus, polymers that permit a rate of drug release that achieves the requisite pharmacokinetics for both the acetaminophen and the opioid for a desired duration, as may be determined using a USP Disintegration Test or Dissolution Test, are determined for use in the dosage forms described herein.

Polymers suitable for use in the dosage forms described herein include those that both swell upon absorption of gastric fluid and gradually erode over a time period of hours. Upon swelling of the polymer matrix, soluble drugs dispersed in the matrix will slowly dissolve in the permeating fluid and diffuse out from the matrix. Drugs that are poorly, or sparingly, soluble are released primarily via erosion of the polymer matrix. Erosion initiates simultaneously with the swelling process, upon contact of the surface of the dosage form with gastric fluid. Erosion reflects the dissolution of the polymer beyond the polymer gel-solution interface where the polymer has become sufficiently dilute that it can be transported away from the dosage form by diffusion or convection. This may also depend on the hydrodynamic and mechanical forces present in the gastrointestinal tract during the digestive process. While swelling and erosion occur at the same time, it is preferred herein that drug release should be erosion-controlled, meaning that the selected polymer should be such that complete drug release occurs primarily as a result of erosion rather than swelling and dissolution. However, swelling should take place at a rate that is sufficiently fast to allow the tablet to be retained in the stomach. At minimum, for an erosional gastric retentive dosage form, there should be an extended period during which the dosage form maintains its size before it is diminished by erosion. Furthermore, the polymer which imbibes fluid to form a gastric retained, extended release polymer matrix is any polymer that is non-toxic, that swells in a dimensionally unrestricted manner upon imbibition of water, and that provides for sustained release of at least one incorporated drug.

Suitable polymers for use in the present dosage forms may be linear, branched, dendrimeric, or star polymers, and include synthetic hydrophilic polymers as well as semi-synthetic and naturally occurring hydrophilic polymers. The polymers may be homopolymers or copolymers, if copolymers, either random copolymers, block copolymers or graft copolymers. Synthetic hydrophilic polymers useful herein include, but are not limited to: polyalkylene oxides, particularly poly(ethylene oxide), polyethylene glycol and poly(ethylene oxide)-poly(propylene oxide) copolymers; cellulosic polymers; acrylic acid and methacrylic acid polymers, copolymers and esters thereof, preferably formed from acrylic acid, methacrylic acid, methyl acrylate, ethyl acrylate, methyl metbacrylate, ethyl methacrylate, and copolymers thereof, with each other or with additional acrylate species such as aminoethyl acrylate; maleic anhydride copolymers; polymaleic acid; poly(acrylamides) such as polyacrylamide per se, poly(methacrylamide), poly(dimethylacrylamide), and poly(N-isopropyl-acrylamide); poly(olefinic alcohol)s such as poly(vinyl alcohol); poly(N-vinyl lactams) such as poly(vinyl pyrrolidone), poly(N-vinyl caprolactam), and copolymers thereof; polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol and polyoxyethylated glucose; polyoxazolines, including poly(methyloxazoline) and poly (ethyloxazoline); polyvinylamines; polyvinylacetates, including polyvinylacetate per se as well as ethylene-vinyl acetate copolymers, polyvinyl acetate phthalate, and the like, polyimines, such as polyethyleneimine; starch and starch-based polymers; polyurethane hydrogels; chitosan; polysaccharide gums; zein; and shellac, ammoniated shellac, shellac-acetyl alcohol, and shellac n-butyl stearate.

Examples of polymers suitable for use in this invention are cellulose polymers and their derivatives (such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly(2-ethyl-2-oxazoline), poly(ethyleneimine), polyurethane hydrogels, and crosslinked polyacrylic acids and their derivatives. Further examples are copolymers of the polymers listed in the preceding sentence, including block copolymers and grafted polymers.

The terms "cellulose" and "cellulosic" are used herein to denote a linear polymer of anhydroglucose. Preferred cellulosic polymers are alkyl-substituted cellulosic polymers that ultimately dissolve in the gastrointestinal (GI) tract in a predictably delayed manner. Preferred alkyl-substituted cellulose derivatives are those substituted with alkyl groups of 1 to 3 carbon atoms each. Examples are methylcellulose, hydroxymethyl-cellulose, hydroxyethylcellulose, hydroxypropylcellulose, hydroxypropylmethylcellulose, and carboxymethylcellulose. In terms of their viscosities, one class of preferred alkyl-substituted celluloses includes those whose viscosity is within the range of about 100 to about 110,000 centipoise as a 2% aqueous solution at 20° C. Another class includes those whose viscosity is within the range of about 1,000 to about 4,000 centipoise as a 1% aqueous solution at 20° C.

The amount of polymer relative to the drug can vary, depending on the drug release rate desired and on the polymer, its molecular weight, and excipients that may be present in the formulation. The amount of polymer will be sufficient however to retain at least about 50% of the drugs within the matrix one hour after ingestion (or immersion in the gastric fluid). Preferably, the amount of polymer is such that at least 55%, 60%, 65%, 70%, 75%, or 80% of the drugs remains in the extended release matrix one hour after ingestion. The amount of polymer is such that at least 20%, 25%, 30%, 35%, 40% or 45% of the drugs remains in the extended release matrix four hours after ingestion. The amount of polymer is such that at least 75%, 80%, or 85% of the drugs is released within six hours after ingestion. In all cases, however, the drugs will be substantially all released from the matrix within about ten hours, and preferably within about eight hours, after ingestion, and the polymeric matrix will remain substantially intact until all of the drug is released. The term "substantially intact" is used herein to denote a polymeric matrix in which the polymer portion substantially retains its size and shape without deterioration due to becoming solubilized in the gastric fluid or due to breakage into fragments or small particles.

The water-swellable polymers can be used individually or in combination. Certain combinations will often provide a more controlled release of the drug than their components when used individually. Examples are cellulose-based polymers combined with gums, such as hydroxyethyl cellulose or hydroxypropyl cellulose combined with xanthan gum. Another example is poly(ethylene oxide) combined with xanthan gum.

As discussed above, the gastric retentive nature and release profiles of a dosage form will depend partially upon the molecular weight of the swellable polymer. The polymers are preferably of a moderate to high molecular weight (900,000 Da to 4,000,000 Da) to enhance swelling and provide control of the release of the opioid and acetaminophen via erosion of the polymer matrix. An example of suitable polyethylene oxide polymers are those having molecular weights (viscosity average) on the order of 900,000 Da to 2,000,000 Da. Using a lower molecular weight ("MW") polyethylene oxide, such as POLYOX™ 1105 (900,000 MW) release for both drugs are higher. Using a higher molecular weight polyethylene oxide (such as POLYOX™ N-60K (2,000,000 MW) or POLYOX™ WSR-301 (4,000,000 MW) reduces the rate of release for both drugs. In one embodiment of the invention, a hydroxypropylmethylcellulose polymer of such molecular weight is utilized so that the viscosity of a 1% aqueous solution is about 4000 cps to greater than 100,000 cps.

A typical dosage form should swell to approximately 115% of its original volume within 30 minutes after administration, and at a later time should swell to a volume that is 130% or more of the original volume.

The acetaminophen and opioid are dispersed within the polymeric matrix described above. The acetaminophen as used herein is preferably a USP powder. Such powders of acetaminophen are known in the art as difficult to compress into tablet forms. In alternative gastric retentive extended release oral dosage forms comprising acetaminophen and an opioid, the acetaminophen used may be a milled form, for example, various COMPAP® compositions (Mallinckrodt, Inc.). In certain embodiments, the opioid analgesic is selected from tramadol, oxycodone, hydrocodone, hydromorphone, oxymorphone, methadone, morphine, or codeine, or pharmaceutically acceptable salts thereof.

Dosage forms prepared for oral administration according to the present disclosure will generally contain other inactive additives (excipients) such as binders, lubricants, disintegrants, fillers, stabilizers, antioxidants, chelating agents, surfactants, coloring agents, and the like. The excipients described below may be present in the ER layer, the IR layer or both layers.

Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum.

Lubricants are used to facilitate tablet manufacture, promoting powder flow and preventing particle capping (i.e., particle breakage) when pressure is relieved. Useful lubricants are magnesium stearate (in a concentration of from 0.25 wt % to 3 wt %, preferably 0.2 wt % to 1.0 wt %, more preferably about 0.3 wt %), calcium stearate, stearic acid, and hydrogenated vegetable oil (preferably comprised of hydrogenated and refined triglycerides of stearic and palmitic acids at about 1 wt % to 5 wt %, most preferably less than about 2 wt %).

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Fillers include, for example, materials such as silicon dioxide, titanium dioxide, alumina, talc, kaolin, powdered cellulose, and microcrystalline cellulose, as well as soluble materials such as mannitol, urea, sucrose, lactose, lactose monohydrate, dextrose, sodium chloride, and sorbitol. Solubility-enhancers, including solubilizers per se, emulsifiers, and complexing agents (e.g., cyclodextrins), may also be advantageously included in the present formulations.

Stabilizers, as well known in the art, are used to inhibit or retard drug decomposition reactions that include, by way of example, oxidative reactions.

Chelating agents tend to form complexes with trace amount of heavy metal ions inactivating their catalytic activity in the oxidation of medicaments. Chelating agents for use in the dosage forms described herein include, but are not limited to, ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N',N", N'''-tetraacetic acid, 1,4,7,10-tetraaza-cyclododecane-N,N', N"-triacetic acid, 1,4,7-tris(carboxymethyl)-10-(2'-hydroxypropyl)-1,4,7,10-tetraazocyclodecane, 1,4,7-triazacyclonane-N,N',N"-triacetic acid, 1,4,8,11-tetraazacyclotetra-decane-N,N',N",N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N, N',N'-tetraacetic acid.

Anti-oxidant may increase the stability of the dosage form by increasing the stability of the active ingredient as well as the dosage form as a whole. The anti-oxidant may be selected from ascorbic acid, citric acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, or propylgallate, or any combination of the above.

The formulations are typically in the form of tablets. Other formulations contain the matrix/active agent particles in capsules. The encapsulating material should be highly soluble so that the particles are freed and rapidly dispersed in the stomach after the capsule is ingested. Such dosage forms are prepared using conventional methods known to those in the field of pharmaceutical formulation and described in the pertinent texts, e.g., in Gennaro, A. R., editor. "Remington: The Science & Practice of Pharmacy", 21st ed., Williams & Williams, and in the "Physician's Desk Reference", 2006, Thomson Healthcare.

The tablets described herein may have individual layers containing one or both drugs for delivering the component drug(s) in the immediate release or the extended release mode. For example, a layer for immediate release of acetaminophen or both acetaminophen and opioid can be added to the layer containing both drugs for extended release. As to acetaminophen in this embodiment, although at steady state, unlike single dose administration, bioavailability is quite constant between the doses of 325 mg and 2000 mg. This may be desirable for prompt relief or bioavailability enhancement due to first-pass metabolism of acetaminophen or the particular opioid.

Alternative gastric retentive drug delivery systems include the swellable bilayer described by Franz, et al., U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389, and Shell, et al., WO 9855107, and the pulsatile gastric retentive dosage form by Cowles et al., U.S. Pub. No. 2009/0028941, all of which are incorporated herein by reference.

A bilayer tablet can be made with one layer containing only the opioid and the second layer containing only the acetaminophen if a substantially different release profile for each drug is desired if the two drugs are not chemically compatible.

It is also envisioned that a third layer containing one or more drugs for immediate release can be added to the dosage form.

Thus, the dosage forms provide controlled delivery of acetaminophen, and an opioid analgesic to the upper GI tract by a polymer matrix that swells unrestrained dimensionally, and is retained in the stomach when taken with food, i.e., in the fed mode. In an environment of use, the dosage forms swell on contact with water from gastric fluid due to the component hydrophilic polymers, (for example, polyethylene oxide and/or hypromellose), and increase in size to be retained in the fed stomach. Acetaminophen and an opioid, for example oxycodone, hydrocodone, or codeine, will be released from these gastric retained dosage forms over an extended period of time, about 3 to about 12 hours, preferably about 4 to about 9 hours, more preferably at least about 5 hours, to the upper gastrointestinal (GI) tract where acetaminophen, and potentially the opioid, is best absorbed, It is also notable that the presence of an opioid in a gastric retentive dosage form may adversely affect the ability of a dosage form to erode at a rate that allows the desired release rates for the active agents. This is due to the fact that administration of opioids is known to reduce gastric motility (Nimmo et al., Br. J. Clin. Pharmac. (1975) 2:509-513). The reduced gastric motility, in turn, may reduce the ability of the dosage form to erode and release the drug within the erodible matrix.

Studies presented herein show that co-administration to dogs of a gastric retentive dosage form and a solution of opioid in amounts to simulate release by the embodied immediate release component have no significant effects on erosion of the gastric retentive extended release dosage forms. Furthermore, studies are done with the disclosed gastric retentive tablet which comprises both the extended release and immediate release drug layers to show the presence of opioid in the described dosage forms does not significantly affect erosion of the tablets in the dog stomach.

The pharmaceutically acceptable dosage form described herein further comprises an immediate release component. The immediate release component comprises acetaminophen and an opioid at lower amounts as compared to the amounts of the opioid and the acetaminophen the gastric retained extended release portion of the dosage form. In another aspect, the amount of acetaminophen in generally between about 10 to 20, more typically between 12 to 16 times the amount of opioid in the immediate release component.

In a preferred aspect, the immediate release component is in contact with the extended release component.

The immediate release component may further comprise excipients such as binders, lubricants, disintegrants, fillers, stabilizers, surfactants, coloring agents, and the like, as described above for the extended release component.

The immediate release component may release at least 80-100% of the active agents within the first hour of oral administration.

Is it understood by the skilled artisan that delivery time or duration of drug release by a particular dosage form is distinct from the duration of drug delivery by the dosage form. As an example, while an extended release dosage form may release one or more drugs over a period of 3, 4 or more hours, depending on the half-life of the drug and the time of transit of that drug through the gastrointestinal tract, the relevant sites of absorption will be exposed for a period of time beyond the time of drug release from the dosage form. Thus, for example, a dosage form that releases one or more drugs over a period of approximately 8 hours may be providing delivery of that drug for a period of approximately 12 hours.

The dosage form, as presently described, possesses the additional advantageous feature of being formulated as a standard oral dosage size, then after administration, imbibing water from the gastric fluid and swelling to a size large enough to be retained in the stomach in a fed mode.

III. Methods for Making Solid Dosage Forms

The presently described dosage forms provide for extended release of both acetaminophen and an opioid in the stomach at rates proportional to one another wherein the dosage forms are comprised of a polymer matrix that swells upon imbibition of fluid to a size sufficient for gastric retention. Thus, in formulating the dosage forms, it is critical to provide the properties which simultaneously allow: a) an extent of swelling to provide gastric retention over an extended period, and b) a rate of swelling and erosion that allows extended and proportional release of both a highly soluble and poorly soluble drug.

Furthermore, the formulation of these pharmaceutical oral dosage forms preferably result in final products that meet the requirements of the Food and Drug Administration (FDA). For example, final products preferably have a stable product that does not fracture during storage and transport. This is measured, in part, in terms of friability and hardness. Dosage forms preferably also meet the requirements for content uniformity, which essentially means that the dispersion of the active ingredient(s) is uniform throughout the mixture used to make the dosage form, such that the composition of tablets formed from a particular formulation does not vary significantly from one tablet to another. The FDA requires a content uniformity within a range of 95% to 105%. Moreover, the active ingredients within the dosage forms should remain stable for long periods of time as required for standard consumer use. For example, it is very helpful to provide formulations that protect the active ingredients from undergoing, for example, oxidative degradation.

It is significant to note that acetaminophen can be a particularly challenging pharmaceutical ingredient with which to formulate solid oral dosage forms. Acetaminophen powders are difficult to compress into a tablet form which will not break or fall apart.

The ability to formulate a pharmaceutical oral dosage form which both delivers the desired therapeutically effective ingredient and meets FDA requirements depends, in part, upon the process by which the product is made.

In the case of tablets, as disclosed herein, a first step may involve the granulation. How the granulation is carried out has great impact on the properties of the final product.

Granulation is a manufacturing process which increases the size and homogeneity of active pharmaceutical ingredients and excipients which comprise a solid dose formulation. The granulation process, which is often referred to as agglomeration, changes important physical characteristics of the dry formulation, with the aim of improving manufacturability and, thereby, product quality, as well as providing desired release kinetics. As an example, water-soluble active agents may be granulated with dissolution-retarding materials such as polymers to provide an additional barrier. Such a process may reduce the release-rate of a water-soluble active agent. In the present embodiments, wherein the dosage form comprises a poorly soluble active agent (e.g., acetaminophen) with a highly soluble opioid (e.g., oxycodone HCl), the opioid may be granulated separately from the poorly soluble agent in order to retard the dissolution of the opioid. Moreover, depending upon the polymers applied to the water-soluble active agent, the extent of the diffusion rate of the active agents within a polymer (e.g., PolyOx) matrix may be manipulated to produce the desired release profiles, i.e., one may individually control the release rates of multiple active agents within a dosage form, wherein the active agents have different solubilities. Dissolution-retarding components include, but are not limited to, water soluble or non-water soluble polymers, hydrogel polymers, pH sensitive polymers or any combination thereof in a desired ratio.

Granulation technology can be classified into one of two basic types: Wet granulation and dry granulation. Wet granulation is by far the more prevalent agglomeration process utilized within the pharmaceutical industry.

Most wet granulation procedures follow some basic steps; the drug(s) and excipients are mixed together, and a binder solution is prepared and added to the powder mixture to form a wet mass. The moist particles are then dried and sized by milling or by screening through a sieve. In some cases, the wet granulation is "wet milled" or sized through screens before the drying step. There are four basic types of wet granulation; high shear granulation, fluid bed granulation, extrusion and spheronization and spray drying.

A. Fluid Bed Granulation

The fluid bed granulation process involves the suspension of particulates within an air stream while a granulation solution is sprayed down onto the fluidized bed. During the process, the particles are gradually wetted as they pass through the spay zone, where they become tacky as a result of moisture and the presence of binder within the spray solution. These wetted particles come into contact with, and adhere to, other wetted particles resulting in the formation of particles.

A fluid bed granulator consists of a product container into which the dry powders are charged, an expansion chamber which sits directly on top of the product container, a spray gun assembly, which protrudes through the expansion chamber and is directed down onto the product bed, and air handling equipment positioned upstream and downstream from the processing chamber.

The fluidized bed is maintained by a downstream blower which creates negative pressure within the product container/expansion chamber by pulling air through the system. Upstream, the air is "pre-conditioned" to target values for humidity, temperature and dew point, while special product retention screens and filters keep the powder within the fluid bed system.

As the air is drawn through the product retention screen it "lifts" the powder out of the product container and into the expansion chamber. Since the diameter of the expansion chamber is greater than that of the product container, the air velocity becomes lower within the expansion chamber. This design allows for a higher velocity of air to fluidize the powder bed causing the material to enter the spray zone where granulation occurs before loosing velocity and falling back down into the product container. This cycle continues throughout the granulation process.

The fluid bed granulation process can be characterized as having three distinct phases; pre-conditioning, granulation and drying. In the initial phase, the process air is pre-conditioned to achieve target values for temperature and humidity, while by-passing the product container altogether. Once the optimal conditions are met, the process air is re-directed to flow through the product container, and the process air volume is adjusted to a level which will maintain sufficient fluidization of the powder bed. This pre-conditioning phase completes when the product bed temperature is within the target range specified for the process.

In the next phase of the process, the spraying of the granulating solution begins. The spray rate is set to a fall within a pre-determined range, and the process continues until all of the solution has been sprayed into the batch. It is in this phase where the actual granulation, or agglomeration, takes place.

Once the binder solution is exhausted, the product continues to be fluidized with warm process air until the desired end-point for moisture content is reached. This end-point often correlates well with product bed temperature, therefore in a manufacturing environment, the process can usually be terminated once the target product bed temperature is reached. A typical fluid bed process may require only about thirty to forty-five minutes for the granulation step, plus ten to fifteen minutes on either side for pre-conditioning and drying.

As with any of the wet granulation processes, the most important variable is the amount of moisture required to achieve successful agglomeration. The fluid bed granulation process requires a "thermodynamic" balance between process air temperature, process air humidity, process air volume and granulation spray rate. While higher process air temperature and process air volume add more heat to the system and remove moisture, more granulating solution and a higher solution spray rate add moisture and remove heat via evaporative cooling. These are the critical process parameters which preferably are evaluated as a manufacturing process is developed, and the key is understanding the interdependency of each variable.

Additional factors affecting the outcome of the fluid bed granulation process are the amount and type of binder solution, and the method by which the binder is incorporated within the granulation. However, the most important process variables are the total amount of moisture added through the process, and the rate at which the moisture content is increased. These parameters can have a significant effect on the quality and the characteristics of the granulation. For instance, a wetter fluid bed granulation process tends to result in a stronger granule with a higher bulk density. However, an overly aggressive process, where moisture is added too rapidly, can loose control over achieving the final particle size and particle size distribution objectives.

"Fluid-bed granulating," as used herein, refers to the method of preparing granules using a fluid bed granulation process as understood by one having ordinary skill in the art.

B. High Shear Granulation

Most pharmaceutical products manufactured by wet granulation utilize a high shear process, where blending and wet massing are accomplished by the mechanical energy generated by an impeller and a chopper. Mixing, densification and agglomeration are achieved through the "shear" forces exerted by the impeller; hence the process is referred to as high shear granulation.

"High shear granulating," as used herein, refers to the method of preparing granules using a high shear granulation process as understood by one having ordinary skill in the art.

The process begins by adding the dry powders of the formulation to the high shear granulator, which is a sealed "mixing bowl" with an impellor which rotates through the powder bed, and a chopper blade which breaks up over-agglomerates which can form during the process. There are typically three phases to the high shear process; dry mixing, solution addition, or wet massing and high shear granulation.

In the first phase, dry powders are mixed together by the impeller blade which rotates through the powder bed. The impeller blade is positioned just off the bottom of the product container. There is a similar tolerance between the tips of the impeller blade and the sides of the container. The impeller blades rotation trough the powder bed creates a "roping" vortex of powder movement. The dry mixing phase typically lasts for only a few minutes.

In the second phase of the process, a granulating liquid is added to the sealed product container, usually by use of a peristaltic pump. The solution most often contains a binder with sufficient viscosity to cause the wet massed particles to stick together or agglomerate. It is common for the solution addition phase to last over a period of from three to five minutes. While the impeller is rotating rather slowly during this step of the process, the chopper blade is turning at a fairly high rate of speed, and is positioned within the product container to chop up over-sized agglomerates, while not interfering with the impellers movement.

Once the binder solution has been added to the product container, the final stage of the granulation process begins. In this phase, high shear forces are generated as the impeller blades push through the wet massed powder bed, further distributing the binder and intimately mixing the ingredients contained therein. The impeller and chopper tool continue to rotate until the process is discontinued when the desired granule particle size and density end-points are reached. This end-point is often determined by the power consumption and/or torque on the impeller.

Once the high shear granulation process has been completed, the material is transferred to a fluid bed dryer, or alternatively, spread out onto trays which are then placed in a drying oven, where the product is dried until the desired moisture content is achieved, usually on the order of 1-2% as measured by Loss On Drying technique.

The most important variable which affects the high shear process is the amount of moisture required to achieve a successful granulation. A key to the process is having the right amount of moisture to allow for agglomeration to occur. Too little moisture will result in an under-granulated batch, with weak bonds between particles and smaller, to non-existent particles, with properties similar to those of the dry powder starting materials. On the other hand, excess moisture can result in a "crashed" batch with results varying from severe over-agglomeration to a batch which appears more like soup.

Other critical formulation parameters affecting the outcome of the high shear granulation process are the amount and type of binder solution, and the method by which the binder is incorporated within the granulation. For example, it is possible to include some of the binder in the dry powder mixture as well as in the granulating solution, or it may be incorporated only in the granulating solution or only in the dry powder, as is the case where water is used as the granulating solution.

The high shear granulation process parameters which are variable include impeller and chopper speeds, the solution addition rate, and the amount of time allocated to the various phases of the process. Of these, the most important variables are the solution addition rate and the amount of time the wet massed product is under high shear mixing C. Extrusion and Spheronization This specialized wet granulation technique involves multiple processing steps and was developed to produce very uniform, spherical particles ideally suited for multi-particulate drug delivery of delayed and sustained release dosage forms.

Similar to high shear granulation initially, the first step involves the mixing and wet massing of the formulation. Once this step is complete, the wet particles are transferred to an extruder which generates very high forces used to press the material out through small holes in the extruder head. The extrudate is of uniform diameter and is then transferred onto a rotating plate for spheronization. The forces generated by the rotating plate initially break up the extruded formulation strands into uniform lengths. Additional dwell time within the spheronizer creates particles which are quite round and very uniform in size. These pellets or spheres may then be dried to the target moisture content, usually within a fluid bed system.

Particles produced in this manner tend to be very dense, and have a capacity for high drug loading, approaching 90% or more in some cases. Importantly, the particle size is very uniform, and the size distribution is very narrow, as compared to other granulation approaches. This quality assures consistent surface area within and between batches, which is extremely important when functional coatings are subsequently applied to create sustained release formulations, delayed release formulations and formulations designed to target a specific area within the body.

Uniform surface area is important because the pharmaceutical coating process endpoint is determined not by coating thickness, but by the theoretical batch weight gain of the coating material. If the batch surface area is consistent, then the coating thickness will also be consistent for a given weight gain, and coating thickness is the primary variable in determining the functionality of the coating system, whether the goal is controlling the duration of sustained release formulations or imparting an acid resistant characteristic to "beads" necessary to protect certain compounds which would otherwise be severely degraded in the presence of the acidic environment of the stomach.

D. Spray Drying

Spray drying is a unique and specialized process which converts liquids into dry powders. The process involves the spraying of very finely atomized droplets of solution into a "bed" or stream of hot process air or other suitable gas. Not typically utilized for the conventional granulation of dosage form intermediates, spray drying has gained acceptance within the industry as a robust process which can improve drug solubility and bioavailability.

Spray drying can be used to create co-precipitates of a drug/carrier which can have improved dissolution and solubility characteristics. In addition, the process can also be useful as a processing aid. For example, it is much more difficult to maintain the uniformity of a drug in suspension, as compared to the same compound in solution. One may have a need to develop an aqueous coating or drug layering process utilizing a drug which is otherwise not soluble in water. By creating a co-precipitate of the drug and a suitable water soluble carrier, often a low molecular weight polymer, the co-precipitate will remain in solution throughout the manufacturing process, improving uniformity of the spray solution and the dosage form created by the coating process. Uniformity is particularly important where lower doses of potent compounds are intended to be coated onto beads or tablet cores.

This same process may be used to enhance the solubility and bioavailability of poorly soluble drugs. By complexing certain excipients and the active ingredient within a solvent system which is then spray dried, it is possible to enhance the drugs absorption within the body. Selection of the solvent system, the complexing agent(s) and the ratios utilized within the formulation are all important formulation variables which determine the effectiveness of solubility enhancement utilizing the spray drying technique. Important process parameters which also have a profound effect on drug solubility are the temperatures of the spray solution and process gas, the spray rate and droplet size and the rate of re-crystallization. The spray dried granulations created by these techniques can then be incorporated into capsules or tablets by conventional manufacturing processes.

E. Dry Granulation

The dry granulation process involves three basic steps; the drug(s) and excipients(s) are mixed (along with a suitable binder if needed) and some form of lubrication, the powder mixture is compressed into dry "compacts," and then the compacts are sized by a milling step. The two methods by which dry granulation can be accomplished are slugging and roller compaction.

IV. Methods of Making the Extended Release Gastric Retentive Dosage Forms Disclosed Herein In one aspect, a method of making a gastric retentive extended-release dosage form as a single layer tablet comprising wet granulation of the opioid and the acetaminophen with the binder is provided. The wet granulation can be a fluid-bed or high shear granulation method. The granulated particles are then blended with additional excipients as needed to form a mixture which is then compressed to form tablets.

Extended release polymer matrices comprising acetaminophen and an opioid are made using either POLYOX™ 1105 (approximate molecular weight of 900,000 Daltons), POLYOX™ N-60K (approximate molecular weight of 2,000,000 Daltons), or POLYOX™ WSR-301 (approximate molecular weight of 4,000,000 Daltons). Prior to compression, components are granulated using a top spray fluid bed granulator A solution of povidone (PVP) in water is sprayed onto the acetaminophen and fluid-bed granulated.

After fluid bed granulation and drying of the resultant particles, batches are characterized with respect to properties such as final Loss on Drying (LOD), bulk density, tap density, and particle size.

Loss on Drying (LOD) is determined after each granulation using the Moisture Analyzer. A 1 g samples are taken and loaded into the moisture analyzer. The sample is run for 5 minutes at a temperature of 105° C.

Bulk and tap densities can be determined as follows. A graduated cylinder is filled with a certain amount of material (82-88 g), and the volume recorded to determine the material bulk density. Tap density can be determined with a help of a Tap Density Tester by exposing the material to 100 taps per test and recording the new volume.

Particle size determination is performed immediately after granulation, after sieving through 20 mesh screen to remove agglomerates. Particle diameter is determined with a sieve-type particle diameter distribution gauge using sieves with openings of 44, 53, 75, 106, 150, and 250 mesh. Fractions are weighed on Mettler balance to estimate size distribution. This provides determination of the quantitative ratio by particle diameter of composition comprising extended release particles. Sieve analysis according to standard United States Pharmacopoeia methods (e.g., USP-23 NF 18), may be done such as by using a Meinzer II Sieve Shaker.

The granulated mixture can be blended with the polymer, filler and lubricant in a V-blender. The resultant mixture can be compressed into monolithic, single-layer tablets using a Manesty® BB4 press, with a modified oval 0.3937" width× 0.6299" length×0.075" cup depth tool. Tablets may be prepared at a rate, for example, of approximately 800 tablets per minute.

Tablets are then characterized with respect to disintegration and dissolution release profiles as well as tablet hardness, friability and content uniformity.

In vitro dissolution profiles for the tablets may be determined in USP apparatus (40 mesh baskets), 100 rpm, in pH 5.8 phosphate buffer (0.1N HCl), 37° C. Samples of 5 ml at each time-point, may be taken without media replacement at 1, 2, 4, 6, 8 and 12 hours. In some embodiments, the dissolution profiles may be determined at varying pH values, such as at a pH of about 3.0, 3.5, 4.0, 4.5, 5.0, 5.5, 6.0 or 6.5. The fluid used may be, for example, HCl, phosphate buffer or simulated gastric fluid. The resulting cumulative dissolution profiles for the tablets are, based upon a theoretical percent active added to the formulations.

A tablet preferably disintegrates before it dissolves. A disintegration tester measures the time it takes a tablet to break apart in solution. The tester suspends tablets in a solution bath for visual monitoring of the disintegration rate. Both the time to disintegration and the disintegration consistency of all tablets are measured. The disintegration profile may be determined in a USP Disintegration Tester in pH 5.8 phosphate buffer. In some embodiments, the disintegration profiles may be determined at varying pH values, such as at a pH of about 3.0, 3.5, 4.0, 4.5, 5.0, 5.5, 6.0 or 6.5. The fluid used may be, for example, HCl, phosphate buffer, or simulated gastric fluid. Samples, 1 ml at each time-point, may be taken, for example, without media replacement at 0.5, 1, 2, 3, 4, 5, 6, 7 and 8 hours. The resulting cumulative disintegration profiles are based upon a theoretical percent active added to the formulation is determined.

Tablet hardness changes rapidly after compression as the tablet cools. A tablet that is too hard may not break up and dissolve into solution before it passes through the body. In the case of the presently disclosed gastric retentive dosage forms, a tablet that is too hard may not be able to imbibe fluid rapidly enough to prevent passage through the pylorus in a stomach in a fed mode. A tablet that is too soft may break apart, not handle well, and can create other defects in manufacturing. A soft tablet may not package well or may not stay together in transit.

After tablets are formed by compression, it is desired that the tablets have a strength of at least 9-25 Kiloponds (Kp)/cm$^2$, preferably at least about 12-20 (Kp)/cm$^2$. A hardness tester is used to determine the load required to diametrically break the tablets (crushing strength) into two equal halves. The fracture force may be measured using a Venkel Tablet Hardness Tester, using standard USP protocols.

Friability is a well-known measure of a tablet's resistance to surface abrasion that measures weight loss in percentage after subjecting the tablets to a standardized agitation procedure. Friability properties are especially important during any transport of the dosage form as any fracturing of the final dosage form will result in a subject receiving less than the prescribed medication. Friability can be determined using a Roche Friability Drum according to standard USP guidelines which specifies the number of samples, the total number of drum revolutions and the drum rpm to be used. Friability values of from 0.8 to 1.0% are regarded as constituting the upper limit of acceptability.

The prepared tablets are tested for content uniformity to determine if they meet the pharmaceutical requirement of <6% relative standard deviation (RSD). Each tablet is placed in a solution of 1.0 N HCl and stirred at room temperature until all fragments have visibly dissolved. The solution containing the dissolved tablet is analyzed by HPLC.

In another aspect, a method of making a bilayer tablet comprising a gastric retentive extended-release layer and an immediate release layer is provided. In a further aspect, the gastric retentive extended-release layer is wet-granulated using the fluid bed or high shear granulation process. In yet a further aspect, the immediate release layer is wet-granulated using the fluid bed or high shear granulation process.

In another aspect, a dosage form for release of acetaminophen and an opioid is provided. The dosage form has an immediate release component and an extended release component, each of the components comprising acetaminophen and an opioid. The dosage form when placed in a USP Disintegration test with 800 mL aqueous buffer at pH 1.2 (0.1N HCl) at 37° C. apparatus provides an in vitro release of acetaminophen rate wherein 40-65% acetaminophen is released after 1 hour, 55-80% acetaminophen is released after 2 hours and at least about 75% acetaminophen is released after 6 hours. In one embodiment, the amount of opioid released is within about 20%, more preferably 15%, still more preferably within about 10% or 5% of the amount of acetaminophen released between 1-6 hours, more preferably 1-8 hours.

In another embodiment, the immediate release component of the dosage form releases at least about 70% of the dose of acetaminophen in the immediate release component after 1 hour in a USP disintegration tester with 800 mL aqueous buffer at pH 1.2 at 37° C. and at least about 70% of the dose of opioid in the same test. In another embodiment, the controlled release component of the dosage form releases at least about 40% of the dose of acetaminophen in the controlled release component after 6 hours and at least about 70% of the dose of acetaminophen in the controlled release component after 10 hours, when tested in a USP disintegration tester with 800 mL aqueous buffer at pH 1.2 at 37° C. The dose opioid released from the controlled release component is within about 20%, more preferably 15%, still more preferably within about 10% or 5% of the amount of acetaminophen released from the controlled release component over the desired period of sustained delivery, typically up to 6 hours, more preferably 8 hours.

In still another embodiment, the dosage form is a tablet comprised of an immediate release layer in direct contact with a sustained release, gastric retentive layer. The tablet when placed in a USP Disintegration test apparatus with 800 mL aqueous buffer at pH 1.2 (0.1N HCl) at 37° C. provides an in vitro release such that between 40-65% acetaminophen is released after 1 hour, more preferably between 45-60%, and the amount of opioid released is within about 15%, 10%, or 5% of the amount of acetaminophen released; and between 55-80% acetaminophen is released after 2 hours, more preferably between 60-75%, and the amount of opioid released is within about 15%, 10%, or 5% of the amount of acetaminophen released at this time point.

In still another embodiment, the dosage form is a tablet comprised of an immediate release layer in direct contact with a sustained release, gastric retentive layer. The tablet when placed in a USP Disintegration test apparatus with 800 mL aqueous buffer at pH 1.2 (0.1N HCl) at 37° C. provides an in vitro release such that between 10-25% acetaminophen is released after 1 hour, and the amount of opioid released is within about 15%, 10%, or 5% of the amount of acetaminophen released; and between 30-45% acetaminophen is released after 2 hours, and the amount of opioid released is within about 15%, 10%, or 5% of the amount of acetaminophen released at this time point.

In another embodiment, release of acetaminophen and opioid from the controlled release component of the dosage form is achieved by erosion of the controlled release component and diffusion of the drug. In one embodiment, release of acetaminophen from the controlled release component is achieved by erosion of one or more polymer components in the layer to expose the acetaminophen to the external environment for release of the drug. In another embodiment, release of the opioid from the controlled release component of the dosage form is achieved by erosion of the controlled release component and diffusion of the opiod through a hydrated polymer layer in the controlled release component. The cumulative percent of opioid released is linear when plotted as a function of square root of time for at least a period of 2 hours, more preferably 4 hours.

V. Methods of Treating Pain

In another aspect, a subject suffering from pain or at risk of experiencing pain is treated by oral administration of a gastric retentive extended release dosage form as described above. Treatment of both acute pain and chronic pain are contemplated.

The method of the present invention is useful for treating numerous pain states that are currently being treated with conventional immediate formulations comprising acetaminophen and/or and opioid. These and additional pain states include, by way of illustration and not limitation, headache pain, pain associated with migraine, neuropathic pain selected from the group consisting of diabetic neuropathy, HIV sensory neuropathy, post-herpetic neuralgia, post-thoracotomy pain, trigeminal neuralgia, radiculopathy, neuropathic pain associated with chemotherapy, reflex sympathetic dystrophy, back pain, peripheral neuropathy, entrapment neuropathy, phantom limb pain, and complex regional pain syndrome, dental pain, pain associated with a surgical procedure and or other medical intervention, bone cancer pain, joint pain associated with psoriatic arthritis, osteoarthritic pain, rheumatoid arthritic pain, juvenile chronic arthritis associated pain, juvenile idiopathic arthritis associated pain, Spondyloarthropathies (such as ankylosing spondylitis (Mb Bechterew) and reactive arthritis (Reiter's syndrome)) associated pain, pain associated with psoriatic arthritis, gout pain, pain associated with pseudogout (pyrophosphate arthritis), pain associated with systemic lupus erythematosus (SLE), pain associated with systemic sclerosis (scleroderma), pain associated with Behcet's disease, pain associated with relapsing polychondritis, pain associated with adult Still's disease, pain associated with transient regional osteoporosis, pain associated with neuropathic arthropathy, pain associated with sarcoidosis, arthritic pain, rheumatic pain, joint pain, osteoarthritic joint pain, rheumatoid arthritic joint pain, juvenile chronic arthritis associated joint pain, juvenile idiopathic arthritis associated joint pain, Spondyloarthropathies (such as ankylosing spondylitis (Mb Bechterew) and reactive arthritis (Reiter's syndrome)) associated joint pain, gout joint pain, joint pain associated with pseudogout (pyrophosphate arthritis), joint pain associated with systemic lupus erythematosus (SLE), joint pain associated with systemic sclerosis (scleroderma), joint pain associated with Behcet's disease, joint pain associated with relapsing polychondritis, joint pain associated with adult Still's disease, joint pain associated with transient regional osteoporosis, joint pain associated with neuropathic arthropathy, joint pain associated with sarcoidosis, arthritic joint pain, rheumatic joint pain, acute pain, acute joint pain, chronic pain, chronic joint pain, inflammatory pain, inflammatory joint pain, mechanical pain, mechanical joint pain, pain associated with the fibromyalgia syndrome (FMS), pain associated with polymyalgia rheumatica, monarticular joint pain, polyarticular joint pain, nociceptive pain, psychogenous pain, pain of unknown etiology, pain mediated by IL-6, IL-6 soluble receptor, or IL-6 receptor, pain associated with a surgical procedure in a patient with a clinical diagnosis of OA, pain like static allodynia, pain like dynamic allodynia, pain associated with Crohn's disease, and/or pain associated with completion of a large number of patent applications within a limited interval of time.

Generally, the frequency of administration of a particular dosage form is determined to provide the most effective results in an efficient manner without overdosing and varies according to the following criteria: (1) the characteristics of the particular drug(s), including both its pharmacological characteristics and its physical characteristics, such as solubility; (2) the characteristics of the swellable matrix, such as its permeability; and (3) the relative amounts of the drug and polymer. In most cases, the dosage form is prepared such that effective results are achieved with administration once every eight hours, once every twelve hours, or once every twenty-four hours. As previously discussed, due to the physical constraints placed on a tablet or capsule that is to be swallowed by a patient, most dosage forms can only support a limited amount of drug within a single dosage unit.

In one embodiment, the dosage form allows a dosing frequency of two times a day (b.i.d.) or three times a day (t.i.d.) to result in sustained plasma concentration of both drugs as compared to current immediate release products which require more frequent administration for effective sustained pain relief.

Within the context of the present disclosure, the gastric retentive dosage forms have the advantage of improving patient compliance with administration protocols because the drugs may be administered in a once-daily or twice-daily dosing regimen, rather than the multiple dosing administrations necessary for the immediate release dosage forms of acetaminophen and/or opioids in order to maintain a desired level of pain relief. One embodiment of the invention relates to a method of administering a therapeutically effective amount of a combination of acetaminophen and an opioid to a patient in need thereof, comprising administering the acetaminophen and opioid or pharmaceutically acceptable salts thereof, in a gastric retentive dosage form once in the morning or evening in a once a day daily regime. Another embodiment comprises administering the gastric retentive dosage form twice a day, for example once in the morning and once in the evening in a twice a day daily dosage regime.

For all modes of administration, the gastric retentive dosage forms described herein are preferably administered in the fed mode, i.e., with or just after consumption of a small meal (see U.S. Publication No. 2003/0104062, herein incorporated by reference). When administered in the evening fed mode, the gastric retentive dosage form may provide the subject with continued relief from pain through the night and into the next day. The gastric retentive dosage form of the present invention is able to provide pain relief for an extended period of time because the dosage form allows for both extended release of the acetaminophen and opioid and the superior absorption of the drugs in the GI tract.

In some aspects, the postprandial or fed mode can also be induced pharmacologically, by the administration of pharmacological agents that have an effect that is the same or similar to that of a meal. These fed-mode inducing agents may be administered separately or they may be included in the dosage form as an ingredient dispersed in the shell, in both the shell and the core, or in an outer immediate release coating. Examples of pharmacological fed-mode inducing agents are disclosed in U.S. Pat. No. 7,405,238, entitled "Pharmacological Inducement of the Fed Mode for Enhanced Drug Administration to the Stomach," inventors Markey, Shell, and Berner, the contents of which are incorporated herein by reference.

EXAMPLES

The following examples illustrate certain aspects and advantages of the subject matter, however, the present invention is in no way considered to be limited to the particular embodiments described below.

Example 1

Acetaminophen (APAP) and Phenylephrine (PE) Combination Formulations

Dosage forms were made using an phenylephrine HCl ("PE") model. Phenylephrine is highly soluble in water (500 mg/ml) with a molecular weight (203.67 Daltons (Da)). This solubility is of the same order of magnitude as the above mentioned opioids in a similar molecular weight range (approximately 350 to 450 Da) with similar dose strength and dose range on a milligram basis.

Four formulations for the production of extended release 960 mg tablets comprising acetaminophen (APAP), phenylephrine (PE) and a swellable polymer were manufactured using a dry blend process, and hand made on a Carver Auto C Press (Fred Carver, Inc., Indiana). The formulations also included polyvinylpyrrolidone (PVP) and magnesium stearate. In formulations (samples) 3 and 4, microcrystalline cellulose (MCC) was also added. The dry blend process consisted of blending all the ingredients in a glass jar, and compressing into a 960 mg tablet using a 0.3937"×0.7086" Modified Oval die (Natoli Engineering, St. Charles, Mo.).

The parameters for the operation of the carver Auto C Press were as follows: 3000 lbs force, 0 second dwell time (the setting on the Carver Press), and 100% pump speed. Samples 1 and 2 contain 650 mg acetaminophen and 30 mg phenylephrine. Samples 3 and 4 contain 500 mg acetaminophen and 30 mg phenylephrine. The formulations for the tablets are set forth below in Tables 1-4:

TABLE 1

FORMULATION COMPOSITION (wt %)

| Sample No. | APAP | PE | PVP | PEO N-60K | Mg Stearate |
|---|---|---|---|---|---|
| 1 | 67.71 | 3.13 | 3.88 | 24.28 | 1 |

TABLE 2

FORMULATION COMPOSITION (wt %)

| Sample No. | APAP | PE | PVP | PEO 1105 | Mg Stearate |
|---|---|---|---|---|---|
| 2 | 67.71 | 3.13 | 3.88 | 24.28 | 1 |

TABLE 3

FORMULATION COMPOSITION (wt %)

| Sample No. | APAP | PE | PVP | PEO N-60K | MCC | Mg Stearate |
|---|---|---|---|---|---|---|
| 3 | 52.08 | 3.13 | 3.88 | 24.22 | 16.60 | 1 |

TABLE 4

FORMULATION COMPOSITION (wt %)

| Sample No. | APAP | PE | PVP | PEO 1105 | MCC | Mg Stearate |
|---|---|---|---|---|---|---|
| 4 | 52.08 | 3.13 | 2.97 | 24.22 | 16.60 | 1 |

Gastric retentive acetaminophen (APAP) and phenylephrine (PE) combination 1000 mg tablets were manufactured using a dry blend process, and hand made on a Carver Auto C Press (Fred Carver, Inc., Indiana). The dry blend process consisted of blending all the ingredients in a glass jar, and compressing into a 1000 mg tablet (650 mg APAP and 30 mg PE dose) using a 0.3937"×0.7086" Modified Oval die (Natoli Engineering, St. Charles, Mo.). The parameters for the operation of the carver Auto C Press were as follows: 3000 lbs force, 0 second dwell time (the setting on the Carver Press), and 100% pump speed. The formulations for the tablets are set forth in Table 9:

TABLE 5

FORMULATION COMPOSITION (wt %)

| Sample No. | APAP | PE | MCC | PEO N-60K | Mg Stearate |
|---|---|---|---|---|---|
| 5 | 65 | 3 | 0 | 31 | 1 |
| 6 | 0 | 3 | 65 | 31 | 1 |
| 7 | 65 | 0 | 3 | 31 | 1 |

The dissolution profiles for the above samples 1-7 were determined in USP apparatus (40 mesh baskets), 100 rpm, in pH 5.8 phosphate buffer. Samples of 5 ml at each time-point, were taken without media replacement at 1, 2, 4, 6, 8 and 12 hours. The resulting cumulative dissolution profiles for samples 1-4, based upon a theoretical percent active added to the formulations, are set forth in Tables 6 and 7 below.

TABLE 6

| | THEORETICAL wt % OF ACTIVE RELEASED | | | |
|---|---|---|---|---|
| | SAMPLE 1 | | SAMPLE 2 | |
| TIME (HOURS) | APAP | PE | APAP | PE |
| 1 | 34.0 | 26.5 | 22.1 | 33.6 |
| 2 | 42.5 | 39.5 | 32.1 | 46.5 |
| 4 | 53.8 | 56.4 | 46.8 | 64.5 |
| 8 | 68.4 | 76.2 | 66.8 | 86.4 |
| 12 | 79.0 | 87.5 | 80.4 | 97.6 |

TABLE 7

| | THEORETICAL wt % OF ACTIVE RELEASED | | | |
|---|---|---|---|---|
| | SAMPLE 3 | | SAMPLE 4 | |
| TIME (HOURS) | APAP | PE | APAP | PE |
| 1 | 10.9 | 28 | 11.4 | 33.7 |
| 2 | 18.3 | 39.5 | 21.4 | 47.7 |
| 4 | 31.1 | 55.3 | 38.5 | 66.3 |
| 8 | 66.5 | 87.1 | 79.3 | 97.7 |
| 12 | 51.5 | 75.3 | 62.6 | 87.3 |

The cumulative dissolution release profiles of formulation samples 1-4 are shown in FIG. 1-FIG. 4.

The cumulative dissolution profiles for 5, 6 and 7, based upon a theoretical percent active added to the formulations is set forth in Table 8:

TABLE 8

| | THEORETICAL wt % OF ACTIVE RELEASED | | |
|---|---|---|---|
| | SAMPLE 5 | | SAMPLE 6 | SAMPLE 7 |
| TIME (HOURS) | APAP | PE | PE | APAP |
| 1 | 11 | 31.5 | 21.9 | 11.7 |
| 2 | 18 | 44.2 | 34.4 | 18.9 |
| 4 | 30 | 61.3 | 53.9 | 30.8 |
| 8 | 49 | 82.1 | 77.4 | 49.5 |
| 12 | 64.6 | 94 | 90.2 | 64.6 |

Figure 5:
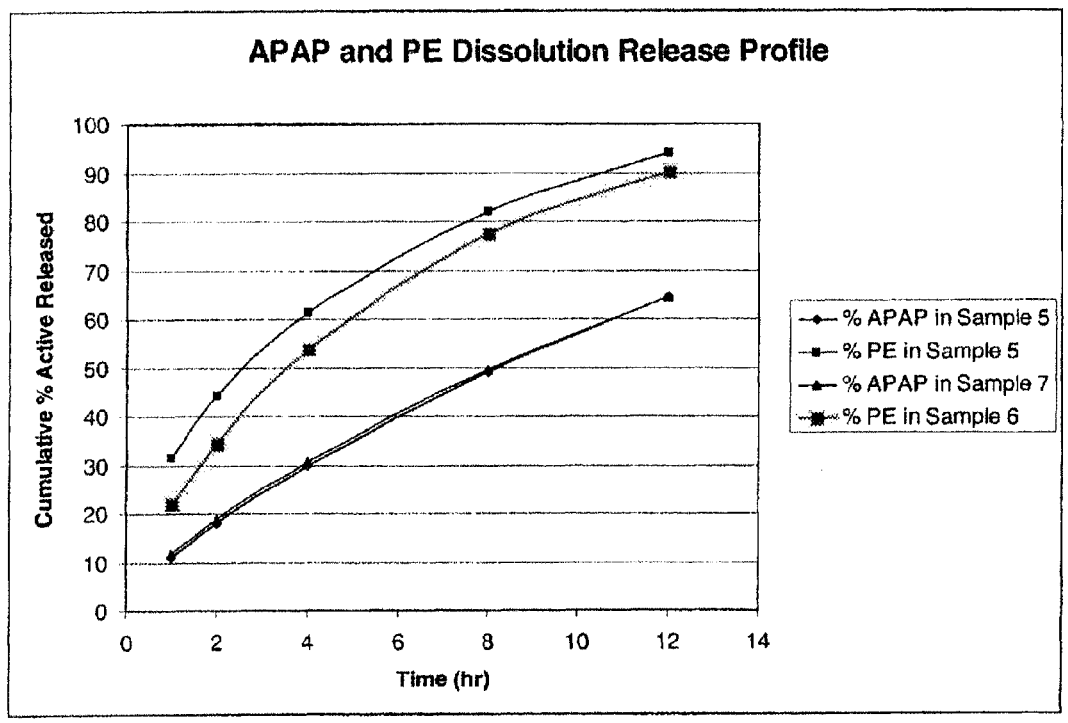
FIG. 5 is a graphical representation of the dissolution profile of a 1000 mg tablet containing 31 weight percent POLYOX® PEO N-60K and varying amounts of microcrystalline cellulose.
Figure 6:
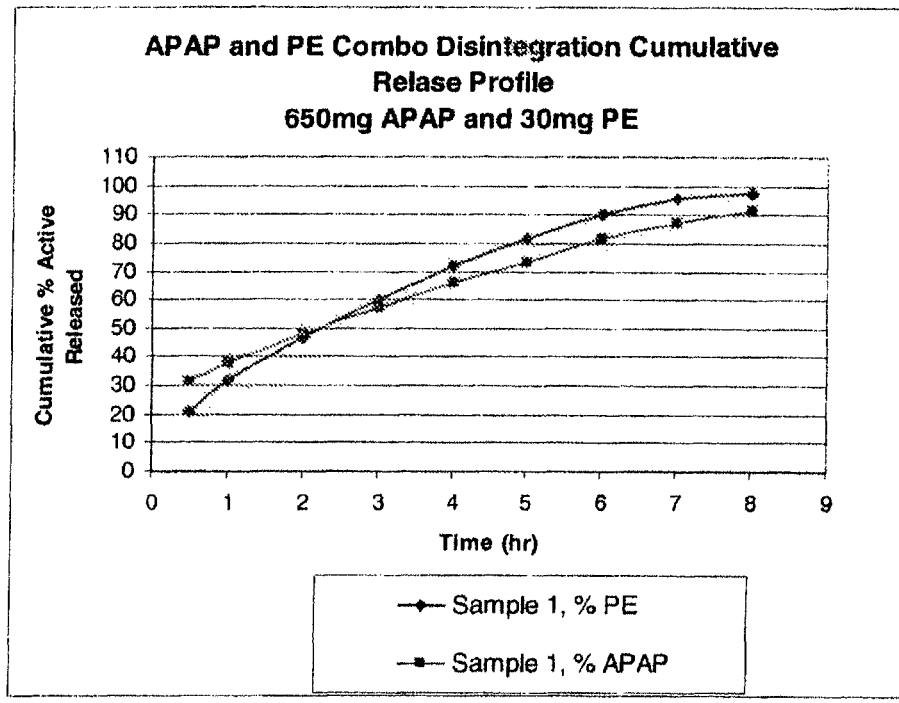
FIG. 6 is a graphical representation of the disintegration profile of a 960 mg tablet containing 650 mg acetaminophen, 30 mg phenylephrine, and 24.28 wt % POLYOX® PEO N-60K.
Figure 7:
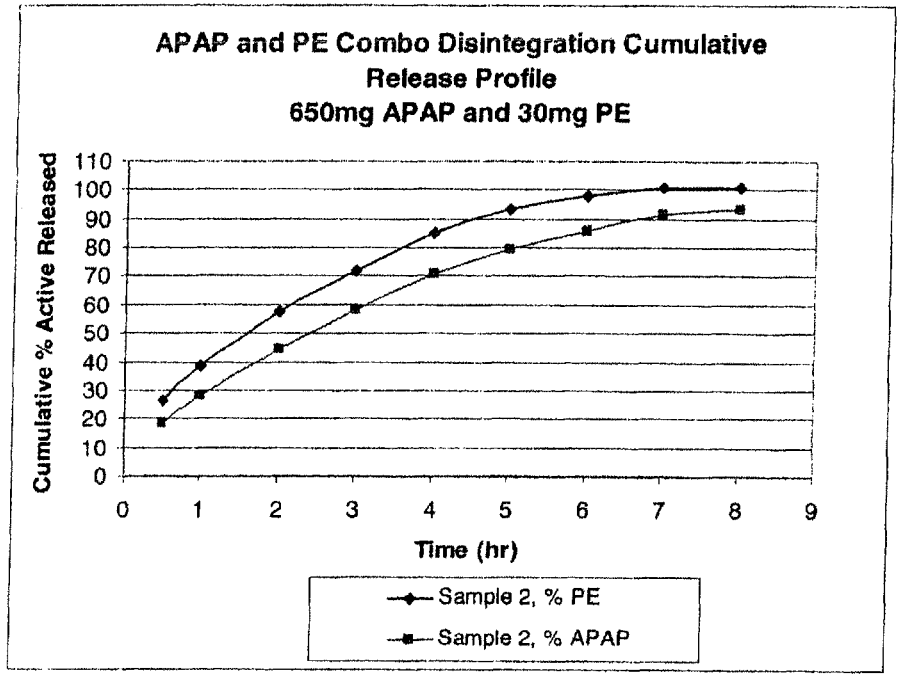
FIG. 7 is a graphical representation of the disintegration profile of a 960 mg tablet containing 650 mg acetaminophen, 30 mg phenylephrine, and 24.28 vvt % POLYOX® PEO 1105.
Figure 8:
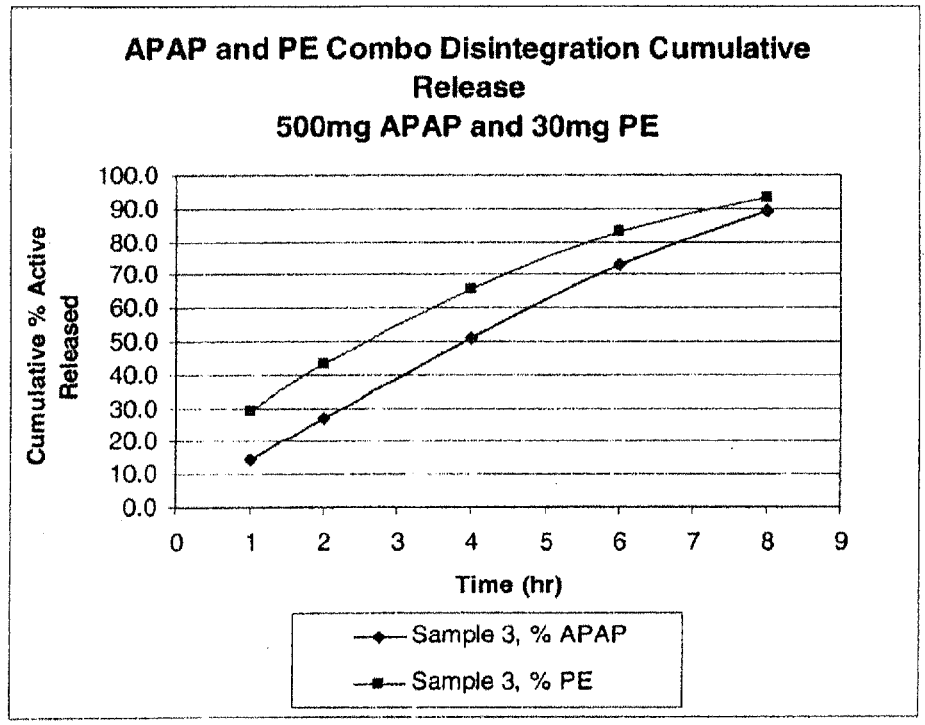
FIG. 8 is a graphical representation of the disintegration release profile of a 960 mg tablet containing 500 mg acetaminophen, 30 mg phenylephrine, 24.22 wt % POLYOX® PEO N-60K and 16.60 wt % MCC.
Figure 9:
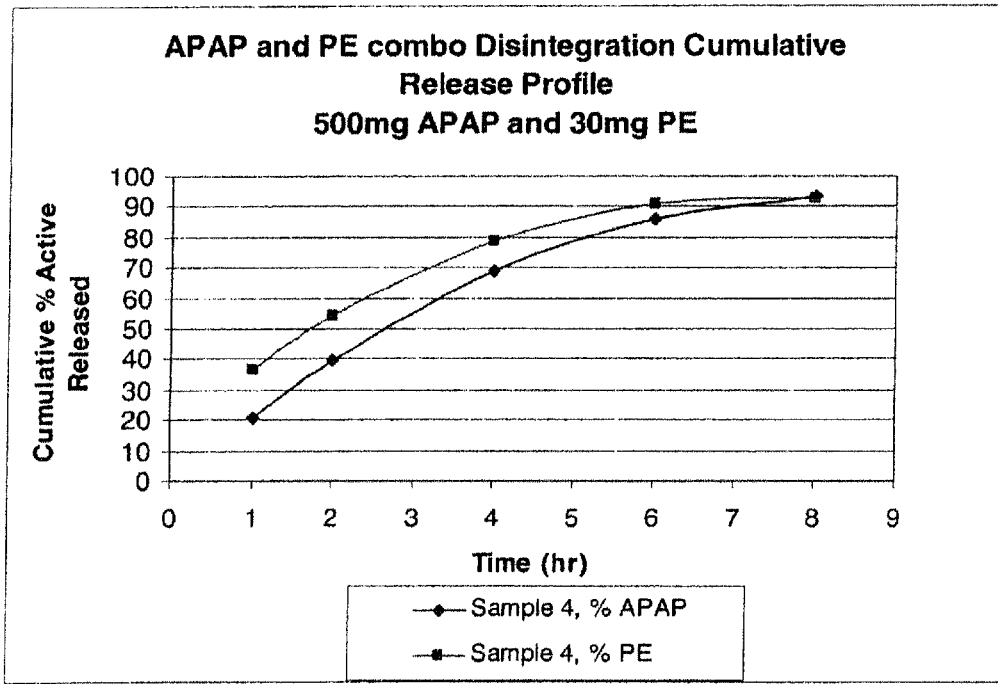
FIG. 9 is a graphical representation of the disintegration release profile of a 960 mg tablet containing 500 mg acetaminophen, 30 mg phenylephrine, 24.22 wt % POLYOX® PEO 1105 and 16.60 wt % MCC.

The cumulative dissolution release profiles of samples 5, 6 and 7 are shown in FIG. 5.

The disintegration was determined in USP Disintegration Tester in pH 5.8 phosphate buffer. Samples, 1 ml at each time-point, were taken without media replacement at 0.5, 1, 2, 3, 4, 5, 6, 7 and 8 hours. The resulting cumulative disintegration profile, based upon a theoretical percent active added to the formulation is set forth in Tables 7 and 8 below.

TABLE 9

| | THEORETICAL wt % OF ACTIVE RELEASED | | | |
|---|---|---|---|---|
| | SAMPLE 1 | | SAMPLE 2 | |
| TIME (HOURS) | APAP | PE | APAP | PE |
| 0.5 | 31.0 | 21.2 | 18.5 | 26.7 |
| 1 | 38.1 | 31.7 | 28.5 | 38.8 |
| 2 | 48.3 | 47.1 | 44.6 | 57.4 |
| 3 | 57.2 | 59.9 | 58.4 | 72.0 |
| 4 | 66.3 | 72.4 | 70.9 | 85.3 |

TABLE 9-continued

| | THEORETICAL wt % OF ACTIVE RELEASED | | | |
|---|---|---|---|---|
| | SAMPLE 1 | | SAMPLE 2 | |
| TIME (HOURS) | APAP | PE | APAP | PE |
| 5 | 73.5 | 81.5 | 79.3 | 93.2 |
| 6 | 81.5 | 90.3 | 86.0 | 98.2 |
| 7 | 87.3 | 95.5 | 91.4 | 100.5 |
| 8 | 91.5 | 97.6 | 93.3 | 100.6 |

TABLE 10

| | THEORETICAL wt % OF ACTIVE RELEASED | | | |
|---|---|---|---|---|
| | SAMPLE 3 | | SAMPLE 4 | |
| TIME (HOURS) | APAP | PE | APAP | PE |
| 1 | 14.8 | 29.4 | 20.9 | 36.4 |
| 2 | 27.2 | 43.1 | 39.9 | 54.4 |
| 4 | 51.1 | 65.5 | 68.7 | 78.9 |
| 6 | 73.0 | 82.9 | 85.8 | 91.1 |
| 8 | 89.5 | 93.0 | 93.3 | 92.6 |

The disintegration release profiles of samples 1-4 are shown in FIG. 6-FIG. 9.

Figure 10:
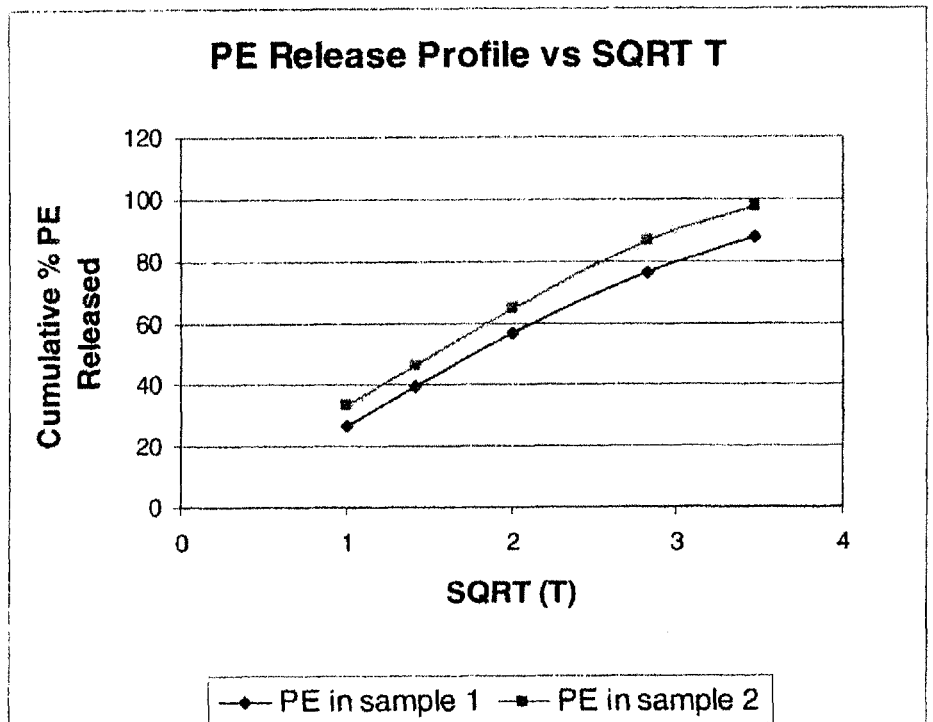
FIG. 10 is a graphical representation of Phenylephrine (PE) release vs. the square root of time of a tablet having 24.28 wt % POLYOX® PEO N-60K (sample 1), and a tablet having 24.28 wt % POLYOX® PEO 1105 (sample 2).
Figure 11:
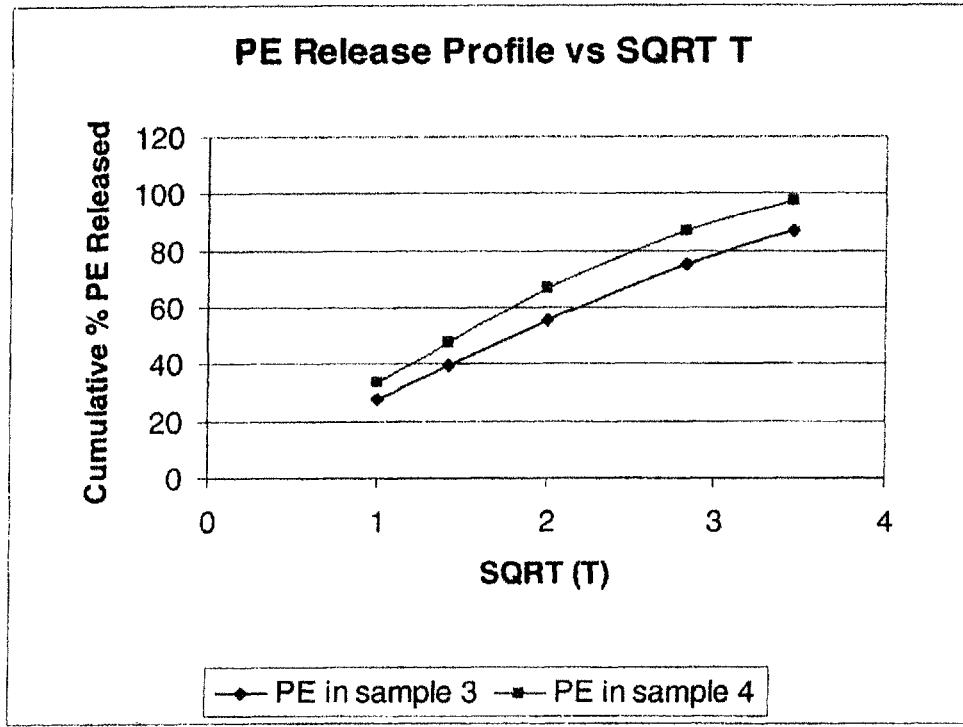
FIG. 11 is a graphical representation of PE release vs. the square root of time generated by a tablet having 24.22 wt % POLYOX® PEO N-60K and 16.60 wt % MCC (sample 3) and a tablet having 24.22 wt % POLYOX® PEO 1105 and 16.60 wt % MCC (sample 4).

Phenylephrine (PE) release profiles vs. square root of time (SQRT (T)) in samples 1-4 are shown in FIG. 10 and FIG. 11, respectively. The graphs show that PE release mechanism in the samples are the mixture of diffusion and erosion. The PE release profiles vs. the square root of time for samples 1 and 2 are shown in FIG. 10. The PE release profiles vs. the square root of time for samples 3 and 4 are shown in FIG. 11.

Figure 2:
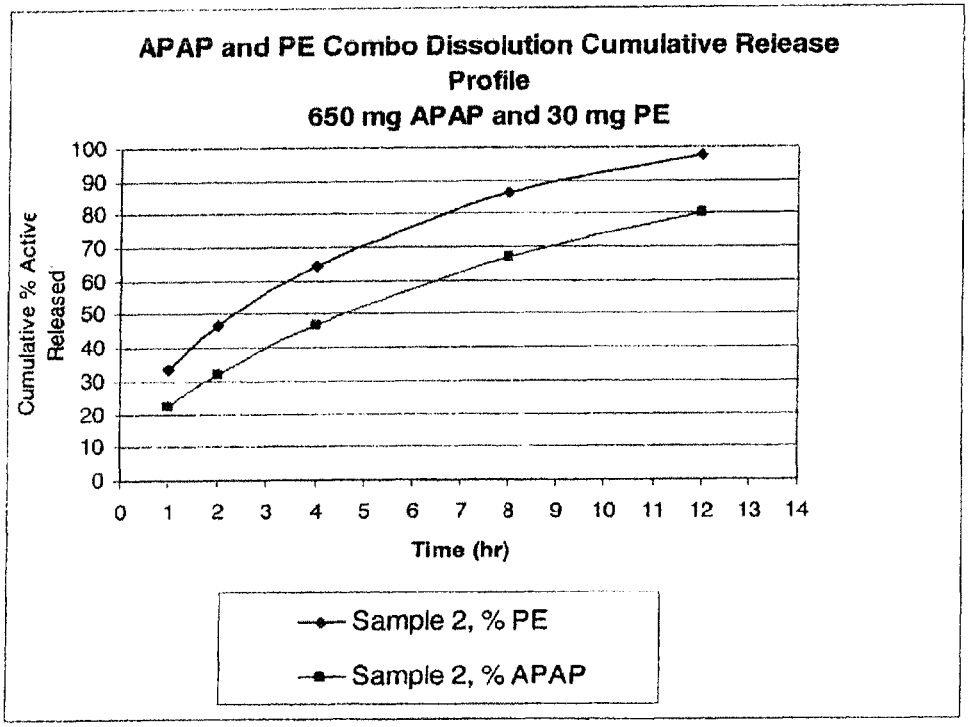
FIG. 2 is a graphical representation of the dissolution profile of a 960 mg tablet containing 650 mg acetaminophen, 30 mg phenylephrine, and 24.28 wt % POLYOX® PEO 1105.
Figure 3:
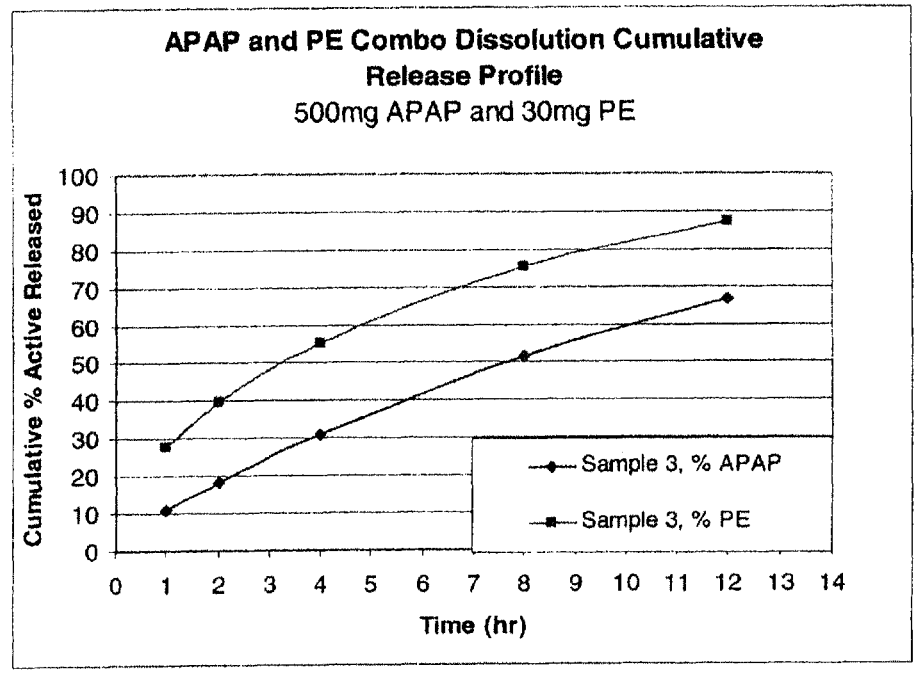
FIG. 3 is a graphical representation of the dissolution release profile of a 960 mg tablet containing 500 mg acetaminophen, 30 mg phenylephrine, 24.22 wt % POLYOX® PEO N-60K and 16.60 wt % MCC.
Figure 4:
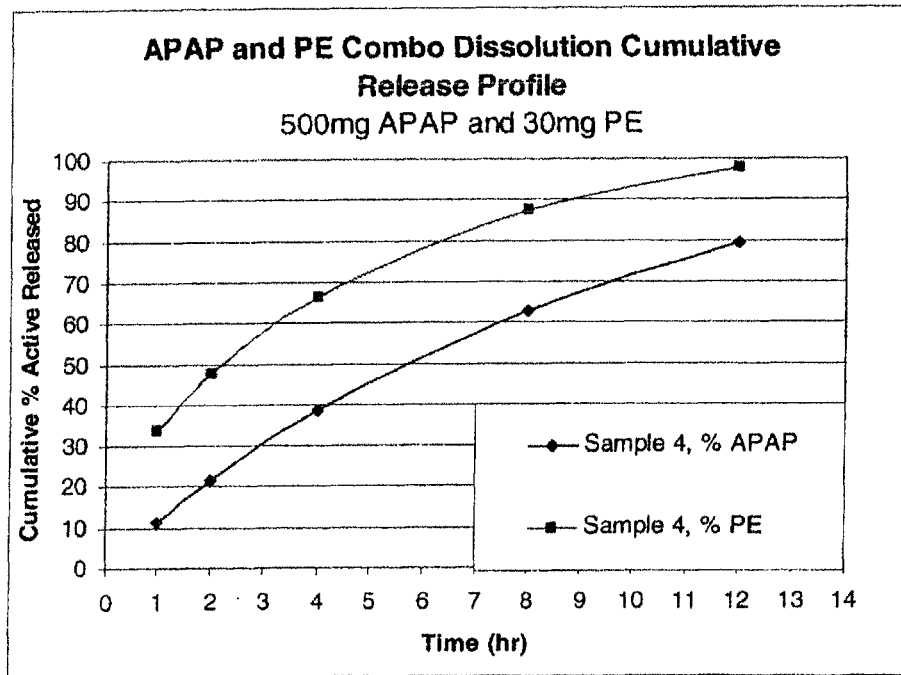
FIG. 4 is a graphical representation of the dissolution release profile of a 960 mg tablet containing 500 mg acetaminophen, 30 mg phenylephrine, 24.22 (wt %) POLYOX® PEO 1105 and 16.60 wt % MCC.

The use of the higher molecular weight polyethylene oxide N60K resulted in a slower rate of release as compared to the use of polyethylene oxide 1105 (for example, compare FIG. 1 and FIG. 2 and compare FIG. 3 and FIG. 4). Adding microcrystalline cellulose to the formulation having 500 mg acetaminophen and polyethylene oxide N60K resulted in a slower release of acetaminophen as compared to the release of phenylephrine (for example, compare FIG. 1 and FIG. 3 and compare FIG. 6 and FIG. 8).

Example 2

Acetaminophen and Oxycodone Hydrochloride Extended Release Gastric Retentive Formulations An extended release matrix comprising acetaminophen, oxycodone hydrochloride and one of two poly(ethylene oxide) polymers (POLYOX®) was manufactured using a fluid bed granulation process followed by screening, blending and compression. Each formulation was prepared in a batch (lot) of 1000 g and contained 42.3 to 42.4 wt % acetaminophen, 2.3 to 2.4 wt % oxycodone hydrochloride, and 1.4 wt % povidone USP (K-29/32). After the granulation, the API granules were screened through USP #20 mesh screen, and blended with various amount of two different grades of POLYOX®, microcrystalline cellulose (Avicel PH 101 NF), and Magnesium Stearate, NF. The blend was then compressed into tablets and ready for analysis. Each batch varied in the amount and type of polymer present. Table 11 below shows the formulation of each batch with POLYOX® 1105 and POLYOX® N60K. Amounts of microcrystalline cellulose (Avicel® PH 101) were varied based on the amounts of the polymer.

TABLE 11

| Lot Number | Polymer (wt/wt %) | Polymer (mg/tablet) | Microcrystalline Cellulose (wt/wt %) | Microcrystalline Cellulose (mg/tablet) |
|---|---|---|---|---|
| 081104-01 | POLYOX® 1105 (20%) | 142.8 mg | (32.9%;) | 235.3 mg |
| 081104-02 | POLYOX® 1105 (32%) | 228.8 mg | (20.9%;) | 149.4 mg |
| 081104-03 | POLYOX® 1105 (50%) | 356.3 mg | (3.2%;) | 23.1 mg |
| 081104-04 | POLYOX® N60K (10%) | 72.0 mg | (42.9%;) | 306.5 mg |
| 081104-05 | POLYOX® N60K (32%) | 229.0 mg | (20.9%;) | 149.4 mg |
| 081104-06 | POLYOX® N60K (45%) | 322.0 mg | (7.9%;) | 56.4 mg |

Batches (lots) of 1 kg each were prepared for each formulation. For each formulation, the acetaminophen was sprayed with a 8.0-8.5% weight/weight solution of povidone and oxycodone hydrochloride in water in a fluid bed granulator (GLATT® top spray GPCG1). Fluid bed process parameters including spray rate (10-30 g/ml), inlet air temperature (50-70° C.), and fluidized air volume were varied to maintain the granule product temperature at a range of 28-35° C. Atomization air pressure was maintained at 1.5 bar for the entire granulation process. Granules were dried and blended with the polymer, filler and lubricant using a V-blender (PK blender, Patterson-Kelly Harsco). The polymer and filler were first blended for 10-15 minutes, the lubricant was then added, and blending was continued for another 4 minutes.

Tablets were then prepared using a Manesty® Beta press, tooled with a modified oval 0.3937" width×0.6299" length× 0.075" cup depth die. A compression force of 7-13 kN (kilo Newton) was used, with a speed of 1000-2200 tablets/min.

Disintegration profiles for the tablets produced from the six batches described above were determined in USP Disintegration Tester in pH 1.2, 0.1N HCl at 37±2° C. Samples were taken without media replacement at 1, 2, 4, 6, 7 and 8 hours.

Results of the disintegration tests for the tablets having the formulations set forth in Table 11 are presented in Table 12 (cumulative oxycodone hydrochloride release) and 13 (cumulative acetaminophen release). Graphical representation of the data is provided in FIG. 12-FIG. 13.

TABLE 12

(Cumulative Oxycodone Hydrochloride Release)

| Time (hr) | Lot 081104-01 | Lot 081104-02 | Lot 081104-03 | Lot 081104-04 | Lot 081104-05 | Lot 081104-06 |
|---|---|---|---|---|---|---|
| 1 | 55 | 31 | 25 | 67 | 26 | 22 |
| 2 | 72 | 51 | 43 | 84 | 40 | 36 |
| 3 | 98 | 85 | 76 | 103 | 67 | 61 |
| 6 | 111 | 106 | 104 | — | 94 | 88 |
| 7 | — | — | 106 | — | 100 | 96 |
| 8 | — | — | — | — | 106 | 105 |

TABLE 13

(Cumulative Acetaminophen Release)

| Time (hr) | Lot 081104-01 | Lot 081104-02 | Lot 081104-03 | Lot 081104-04 | Lot 081104-05 | Lot 081104-06 |
|---|---|---|---|---|---|---|
| 1 | 50 | 24 | 17 | 63 | 18 | 14 |
| 2 | 68 | 45 | 35 | 81 | 32 | 27 |
| 3 | 96 | 80 | 71 | 107 | 60 | 52 |
| 6 | 114 | 107 | 106 | — | 90 | 81 |
| 7 | — | 108 | 110 | — | 98 | 92 |
| 8 | — | — | — | — | 106 | 104 |

The results clearly show that release depends at least in part upon the molecular weight of the poly(ethylene oxide) polymer, the percent composition of the polymer, and the amount of microcrystalline cellulose in the formulation. The cumulative release of oxycodone hydrochloride is presented in FIG. 12, which shows that approximately 20-55% of the oxycodone hydrochloride was released from the tablets containing POLYOX® 1105 within the first hour. The cumulative release profiles of oxycodone hydrochloride from tablets having POLYOX® N60K, shows that approximately 20-65% of the oxycodone hydrochloride was released from the tablets within the first hour. Extended release approaching zero-order was observed over a period of approximately 6 hours for the tablets containing POLYOX® 1105, while tablets containing 32% or 45% POLYOX® N60K exhibited approximately zero-order release over a period of approximately 8 hours.

Figure 13:
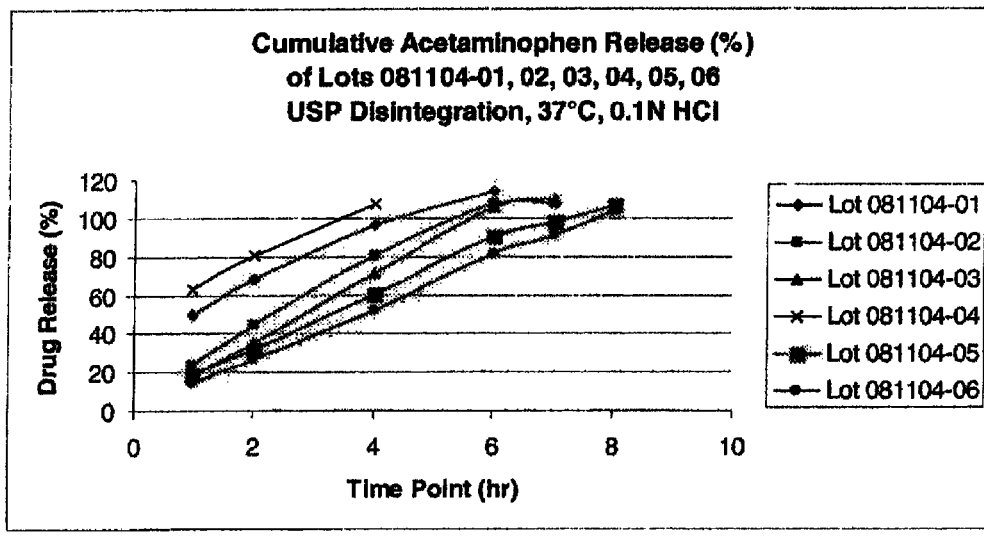
FIG. 13 is a graphical representation of the cumulative acetaminophen disintegration release of tablets containing varying amounts of POLYOX® PEO N-60K or POLYOX® PEO 1105.

The acetaminophen cumulative release profiles for the same dosage forms are presented in FIG. 13, which shows that a range of approximately 20-50% of the acetaminophen was released from the tablets containing POLYOX® 1105 in the first hour, while the cumulative release profiles of acetaminophen from tablets having POLYOX® N60K, show that approximately 15-65% of the acetaminophen was released from the tablets within the first hour. The tablets containing 32% or 45% POLYOX® N60K exhibited extended release approaching zero-order over a period of approximately 8 hours, as seen with the oxycodone hydrochloride.

Figure 12:
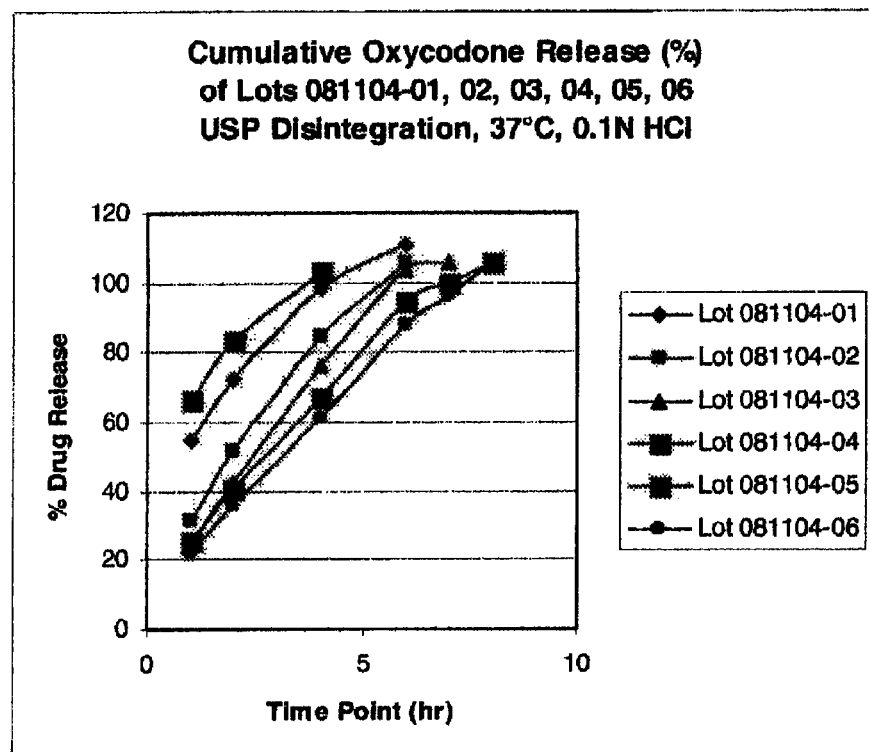
FIG. 12 is a graphical representation of the cumulative oxycodone disintegration release of tablets containing varying amounts of POLYOX® PEO N-60K or POLYOX® PEO 1105.
Figure 14:
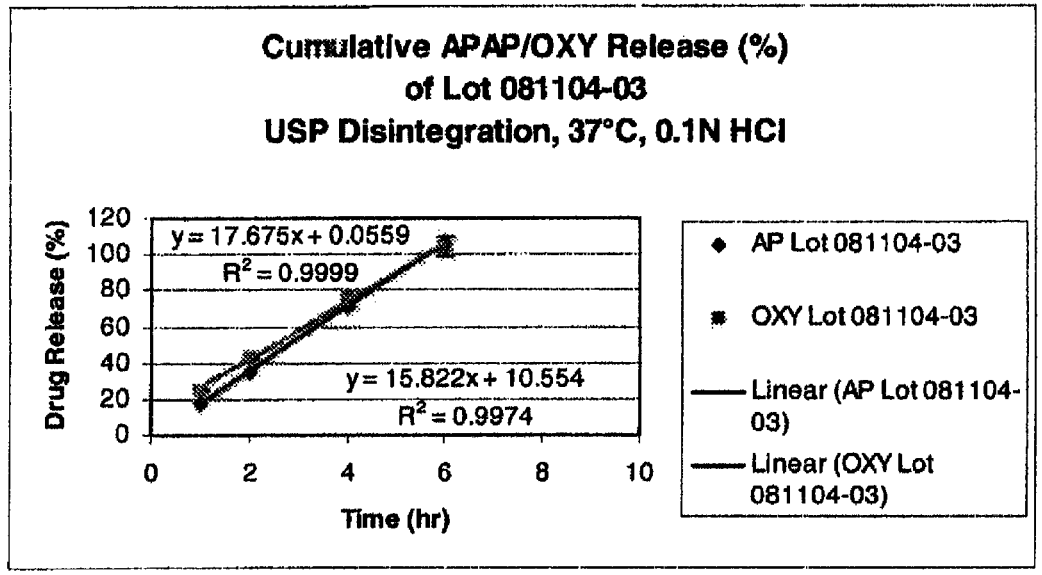
FIG. 14 is a graphical representation of linear regression analysis of oxycodone and acetaminophen release for a dosage form described herein (lot number: 081104-03).
Figure 15:
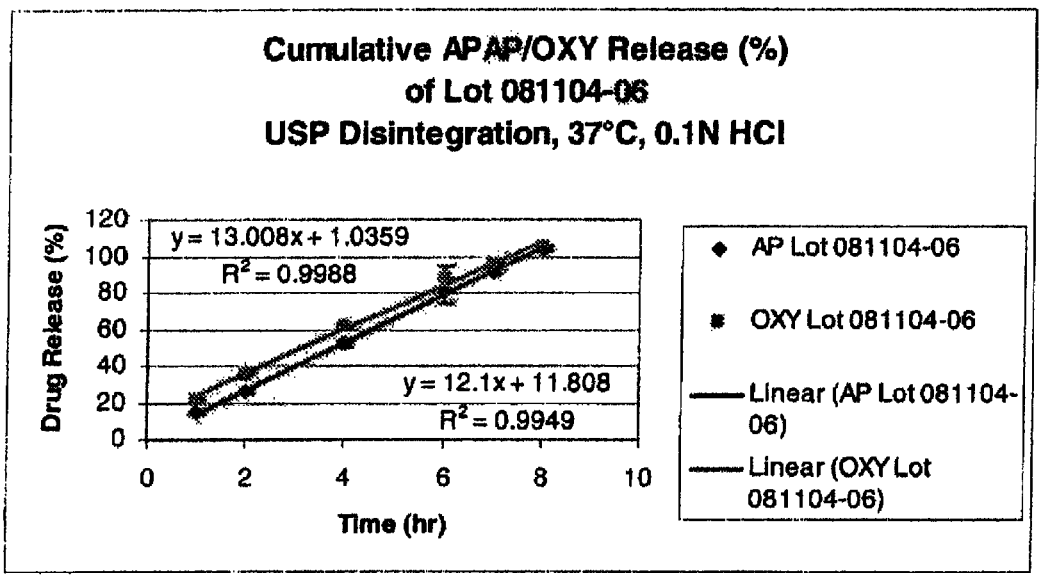
FIG. 15 is a graphical representation of linear regression analysis of oxycodone and acetaminophen release data for a dosage form as described herein (lot number: 081104-06).

Linear regression of data presented in FIG. 12-13 was performed for lots 08110403 (50% POLYOX® 1105) and 08110406 (45% POLYOX® N60K) as shown in FIG. 14 and FIG. 15, respectively. It was determined that oxycodone hydrochloride was released from the tablets having 50% POLYOX® 1105 at a linear rate of approximately 2.8 mg/h while the acetaminophen was released at a rate of approximately 48 mg/h.

Linear regression of cumulative release data for lot 08110406 (45% POLYOX® N60K) show that oxycodone hydrochloride was released from the tablets at a linear rate of approximately 2.1 mg/h while the acetaminophen was released at a rate of 36.8 mg/h.

Content uniformity analysis of lots 08110403 and 08110406 was done by analyzing five tablets from each batch. Each tablet was weighed then transferred to a 250 mL volumetric flask to which 200 mL 0.1N HCl was added. The flask was then set on a magnetic stirrer, a magnetic stir bar was put into the flash and the solution was stirred at approximately 1000 rpm overnight at room temperature, until all fragments had visibly dissolved. Additional 0.1N HCl was then added to the flask to a final volume of 250 mL and stirred for an additional 30 minutes. One mL of each solution for each tablet was placed into a separate flask and diluted with mobile phase solution (97% water/3% IPA/0.1% TFA, apparent pH=3.0±0.1) for analysis on a Agilent 1100/1200 HPLC system.

The resultant data are shown in Tables 14 and 15, respectively. For tablets containing 50% POLYOX® 1105, content uniformity with respect to oxycodone hydrochloride ranged from 91.0% to 92.4% of the label claim, with a mean of 91.6% and a standard deviation of 0.7. Content uniformity with respect to the acetaminophen ranged from 98.5% to 100.5% of the label claim with a mean of 99.4% and a standard deviation of 0.9.

For tablets containing 45% POLYOX® N60K, content uniformity with respect to oxycodone hydrochloride ranged from 91.0% to 95.2% of the label claim, with a mean of 91.6% and a standard deviation of 0.7. Content uniformity with respect to the acetaminophen ranged from 99.2% to 103.1% of the label claim with a mean of 99.4% and a standard deviation of 0.9.

TABLE 14

(Content Uniformity for Oxycodone Hydrochloride)

| Lot Number | APAP % LC (304 mg) | OXY % LC (16 mg) |
|---|---|---|
| 08110403-1 | 100.5 | 92.4 |
| 08110403-2 | 98.8 | 91.2 |
| 08110403-3 | 98.5 | 91.0 |
| 08110403-4 | 100.2 | 92.3 |
| 08110405-5 | 99.1 | 91.2 |
| Mean | 99.4 | 91.6 |
| Stnd Dev | 0.9 | 0.7 |
| % RSD | 0.9 | 0.7 |

TABLE 15

(Content Uniformity for Acetaminophen)

| Lot Number | APAP % LC (304 mg) | OXY % LC (16 mg) |
|---|---|---|
| 08110406-1 | 99.2 | 91.0 |
| 08110406-2 | 101.9 | 93.6 |
| 08110406-3 | 103.1 | 95.2 |
| 08110406-4 | 101.5 | 93.4 |
| 08110406-5 | 99.9 | 91.9 |
| Mean | 101.1 | 93.0 |
| Stnd Dev | 1.6 | 1.6 |
| % RSD | 1.5 | 1.8 |

Tablets were tested for hardness using a Venkel Tablet Tester according to standard USP protocol. Tablet hardness ranged from 9-12 kp.

Example 3

An immediate release composition having acetaminophen and oxycodone hydrochloride was produced using the methods described herein. The formulation is presented in Table 16 below.

TABLE 16

| Ingredient | % wt/wt | Mg/Tablet |
|---|---|---|
| Acetaminophen | 71.3 | 233.2 mg |
| Oxycodone hydrochloride | 4.9 | 16.0 mg |
| Povidone, NF (Plasdone, K29/32) | 9.2 | 30.1 |
| Croscarmellose Sodium, | 1.7 | 5.6 |

TABLE 16-continued

| Ingredient | % wt/wt | Mg/Tablet |
|---|---|---|
| NF (Ac-Di-Sol) | | |
| Lactose Monohydrate, NF (316 Fast Flow) | 6.0 | 19.6 |
| Microcrystalline Cellulose, NF (Avicel PH-101) | 6.0 | 19.6 |
| Magnesium Stearate NF (Non-bovine) | 0.9 | 2.9 |
| Total weight | | 327.0 |

A mixture containing the acetaminophen, croscarmellose sodium, lactose monohydrate, and microcrystalline cellulose was sprayed with a solution containing the oxycodone hydrochloride and povidone (approximately 9%) in water in a fluid bed granulator (Vector® top spray FLM1). The granules were then screened through a USP #20 mesh screen. The resultant granules were blended with magnesium stearate in a V-blender (PK blender, Patterson-Kelly Harsco) for 4 minutes, and were then ready for bilayer compression.

Example 4

Bilayer tablets containing the extended release polymer matrix and the immediate release component (Example 3) were prepared using a Manesty® BB4 press, tooled with a modified oval 0.4337" width×0.7450" length die. The formulation for the extended release material used in the compression is presented in Table 17 below.

TABLE 17

| Ingredient | % wt/wt | Mg/Tablet |
|---|---|---|
| Acetaminophen | 41.9 | 300.0 mg |
| Oxycodone hydrochloride | 2.6 | 18.8 mg |
| Polyethylene oxide, NF (SENTRY ™ POLYOXY ™ WSR N 60K, LEO) | 45.0 | 321.8 |
| Povidone, NF (Plasdone, K29/32) | 3.5 | 25.0 |
| Microcrystalline Cellulose, NF (Avicel PH-101) | 6.0 | 43.0 |
| Magnesium Stearate NF (Non-bovine) | 1.0 | 7.2 |
| Total weight | | 715.0 |

Figure 16:
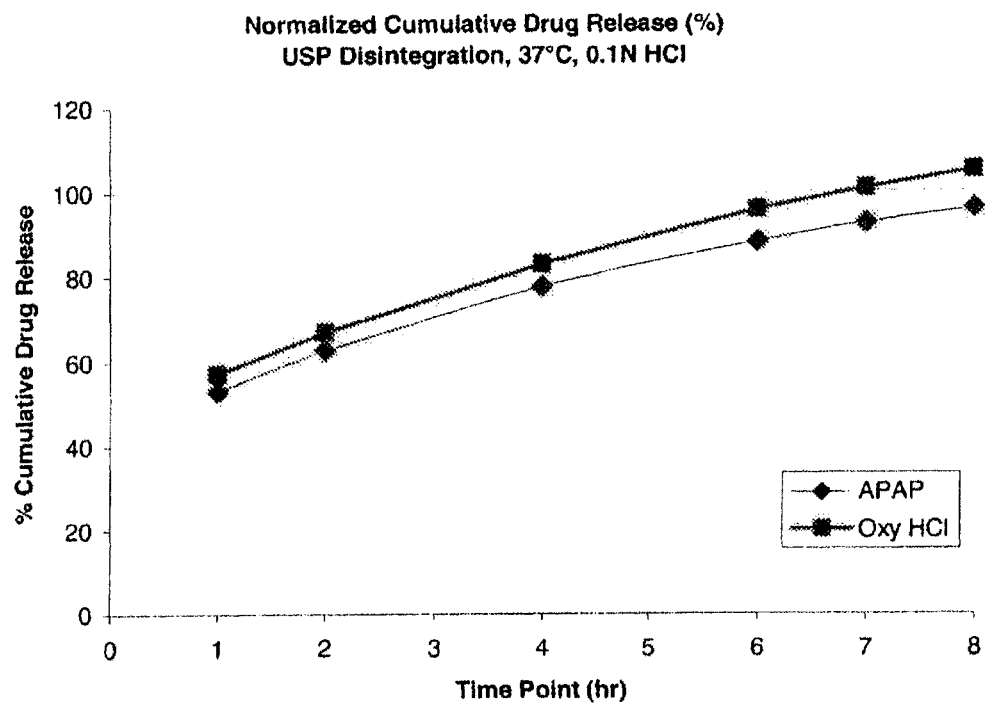
FIG. 16 is a graphical representation of the cumulative acetaminophen and oxycodone HCl disintegration release of a bilayer tablet.

The bilayer tablets were then characterized with respect to cumulative drug release using the USP Disintegration test at 37±2° C. in 0.1N HCl. Results, presented in Table 18 and illustrated in FIG. 16, show that approximately 50-55% of the acetaminophen had been released at the first time point of 1 hour, while approximately 55-57% of the oxycodone hydrochloride had been released by this time. This is indicative of drug release by the immediate release layer. Proportional release of acetaminophen and oxycodone hydrochloride was observed over a period of 8 hours.

TABLE 18

| Time Point (hours) | Cumulative Acetaminophen Released (%) | Cumulative Oxycodone Hydrochloride Released (%) |
|---|---|---|
| 1 | 53.2 | 57.2 |
| 2 | 62.6 | 67.0 |
| 4 | 77.6 | 83.0 |
| 6 | 88.2 | 95.8 |

TABLE 18-continued

| Time Point (hours) | Cumulative Acetaminophen Released (%) | Cumulative Oxycodone Hydrochloride Released (%) |
|---|---|---|
| 7 | 92.7 | 100.9 |
| 8 | 96.1 | 105.1 |

The bilayer tablets were further characterized with respect to content uniformity. Five tablets were analyzed and the results, presented in Table 19, show that content uniformity ranged from 121.8 to 125.2% of the label claim for acetaminophen and ranged from 110.5 to 113.5% for oxycodone HCl. The standard deviation of the acetaminophen and oxycodone HCl were each 1.3, demonstrating that there is very little variation among the tablets with respect to the milligrams of acetaminophen and oxycodone HCl present in the tablets.

TABLE 19

| C.U. Results | APAP % LC | Oxy % LC |
|---|---|---|
| 1 | 124.5 | 113.0 |
| 2 | 121.8 | 110.5 |
| 3 | 125.2 | 113.5 |
| 4 | 123.7 | 111.5 |
| 5 | 123.0 | 111.1 |
| Ave. | 123.6 | 111.9 |
| Std. Dev. | 1.3 | 1.3 |
| % RSD | 1.1 | 1.1 |

Example 5

Bilayer tablets were also prepared using a high shear granulation method. A 5 kg batch was prepared for the gastric retentive extended release mixture and for the immediate release component mixture. The extended release layer contained 42.9% acetaminophen, 2.4 wt % oxycodone hydrochloride, 2.7 wt % povidone, 45.0 wt % POLYOX® N60K, 6.0 wt % microcrystalline cellulose, and 1.0 wt % magnesium stearate. The immediate release layer contained 77.5 wt % acetaminophen, 5.2 wt % oxycodone hydrochloride, 4.0 wt % povidone, 3.0 wt % croscarmellose sodium, 9.2 wt % microcrystalline cellulose, and 0.9 wt % magnesium stearate.

Granules for the extended release layer were prepared by high shear granulation using water as the granulating liquid. The acetaminophen, oxycodone hydrochloride and povidone were charged into a bench scale high shear granulator (Glatt®). The dry powders were blended by running the blade for 1 minute, after which time the water was sprayed onto the mixing blend at a spray rate of approximately 5-30 gm/min. After initiating the spray, the chopper was started and run throughout the spray. Once the granulation was complete, the granulation was discharged from the high shear granulator, and dried using a fluid bed processor (Glatt® top spray GPCG1). Dry granules were screened through an 20-mesh USP screen. Screened granules were blended with the remaining excipients except magnesium stearate in a V-blender (PK blender, Patterson-Kelly Harsco) for 15 minutes. The magnesium stearate was then added to the mixture and blended for another 4 minutes, and ready for bi-layer compression.

Granules for the immediate release layer were prepared using the high shear method as described above for the extended release layer. The acetaminophen, oxycodone hydrochloride, povidone, croscarmellose sodium, and microcrystalline cellulose were granulated using the high shear method prior to blending with magnesium stearate. Granules were screened through USP #20-mesh screen before blending with magnesium stearate. After blending, they were ready for bi-layer compression.

The extended release and immediate release blends were compressed into bilayer tablets using a hand roll method with a Manesty® Beta BB4 press, tooled with a modified oval 0.4337" width×0.7450" length die.

Figure 17:
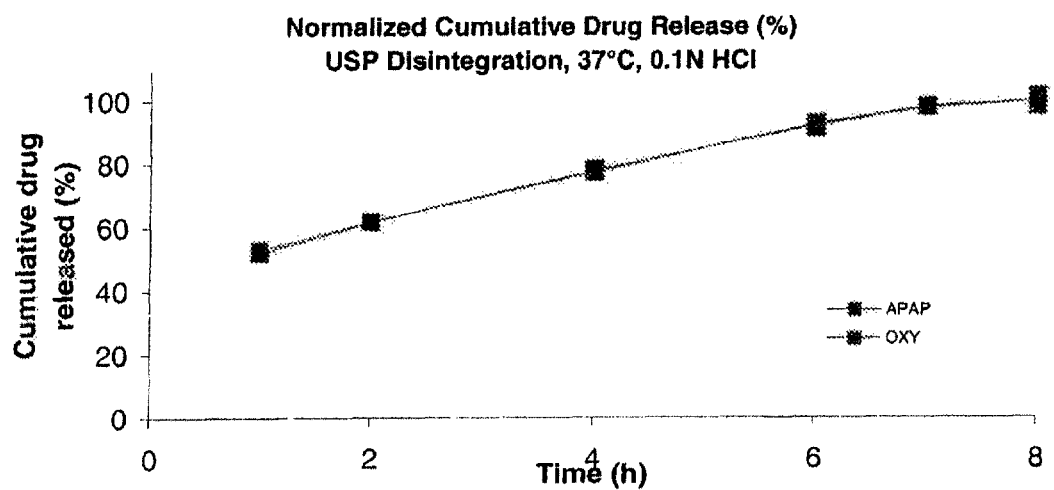
FIG. 17 is a graphical representation of the cumulative acetaminophen and oxycodone HCl disintegration release of a bilayer tablet.

The bilayer tablets prepared by high shear granulation were characterized with respect to cumulative drug release using the USP Disintegration test at 37±2° C. in 0.1N HCl. Results are presented in FIG. 17 and show that approximately 50% of the acetaminophen had been released at the first time point of 1 hour, while approximately 50% of the oxycodone HCl had been released by this time. This is indicative of drug release by the immediate release layer. Proportional release of acetaminophen and oxycodone HCl was observed over a period of approximately 8 hours.

The bilayer tablets were further characterized with respect to content uniformity. Five tablets were analyzed and the results, presented in Table 20, show that content uniformity ranged from 99.1% to 101.9% of the label claim for acetaminophen and ranged from 98.6% to 101.4% for oxycodone HCl. The standard deviation for acetaminophen and oxycodone HCl was 1.2 and 1.3, respectively. Both values demonstrate very low levels of variability among individual tablets with respect to the milligrams of acetaminophen and oxycodone HCl present in the tablets.

Machine production of the bilayer tablets using the Manesty® Beta BB4 press tooled with a modified oval 0.4337" width×0.7450" length die resulted in tablets in which the IR layer was subject to capping.

TABLE 20

| C.U. Results | APAP % LC | Oxy % LC |
|---|---|---|
| 1 | 99.1 | 99.2 |
| 2 | 99.2 | 98.6 |
| 3 | 101.1 | 101.4 |
| 4 | 101.9 | 101.4 |
| 5 | 99.1 | 98.6 |
| Ave. | 100.1 | 99.8 |
| Std. Dev. | 1.2 | 1.3 |
| % RSD | 1.2 | 1.3 |

Example 6

An extended release matrix comprising acetaminophen, tramadol hydrochloride and 45% POLYOX® N60K was manufactured using a fluid bed granulation process followed by screening, blending and compression as described in Example 2. The formulation is shown in Table 21 below:

TABLE 21

| Ingredients | % w/w | mg/tablet |
|---|---|---|
| APAP, USP Powder | 41.9 | 299.9 |
| Tramadol HCl | 2.6 | 18.8 |
| Povidone, USP (K-29/32) | 3.4 | 24.5 |
| POLYOX, NF (N60K) | 45.0 | 321.8 |
| Avicel, NF (PH 101) | 6.0 | 43.0 |
| Mg Stearate, NF | 1.0 | 7.2 |
| Total tablet weight | | 715 mg |

Fluidized bed granulation was performed on Vector FL-M-1 Fluid Bed Granulator. The acetaminophen was sprayed with a binder solution containing the PVP and the tramadol hydrochloride. After granulation, the resultant preparation was characterized with respect to final loss on drying (LOD), bulk density, and tap density.

The granulation parameters and post-granulation characterization are presented below in Table 22.

TABLE 22

| | | 09011201 | 09012001 | 09012101 | 09012201 | 09012202 |
|---|---|---|---|---|---|---|
| Granulation | Batch size (g) | 1000 | 1000 | 1000 | 1000 | 1000 |
| | Inlet air temp (° C.) | 56 | 53-56 | 52-56 | 50-58 | 51-58 |
| | Product temp at spray start (° C.) | 30 | 32 | 31 | 30 | 31 |
| | Product temp during spray (° C.) | 30-38 | 31-34 | 30-34 | 30-36 | 30-34 |
| | Spray rate (rpm) | 15-20 | 12-20 | 12-20 | 12-20 | 12-20 |
| | Spraying time (min) | 29 | 23 | 22 | 23 | 24 |
| | Product temp during drying (° C.) | 36-42 | 34 | 34-35 | 37-38 | 37-38 |
| | Drying time (min) | 3 | 1 | 1 | 1 | 1 |
| Post-gran | Final LOD (%) | 1.47 | 1.66 | 1.69 | 1.38 | 1.75 |
| | Bulk Density (g/ml) | 0.35 | 0.30 | 0.30 | 0.33 | 0.31 |
| | Tap Density (g/ml) | 0.41 | 0.37 | 0.37 | 0.40 | 0.39 |

The granulation mixture was then screened and blended with the remaining excipients in a V blender and compressed into tablets.

Figure 18:
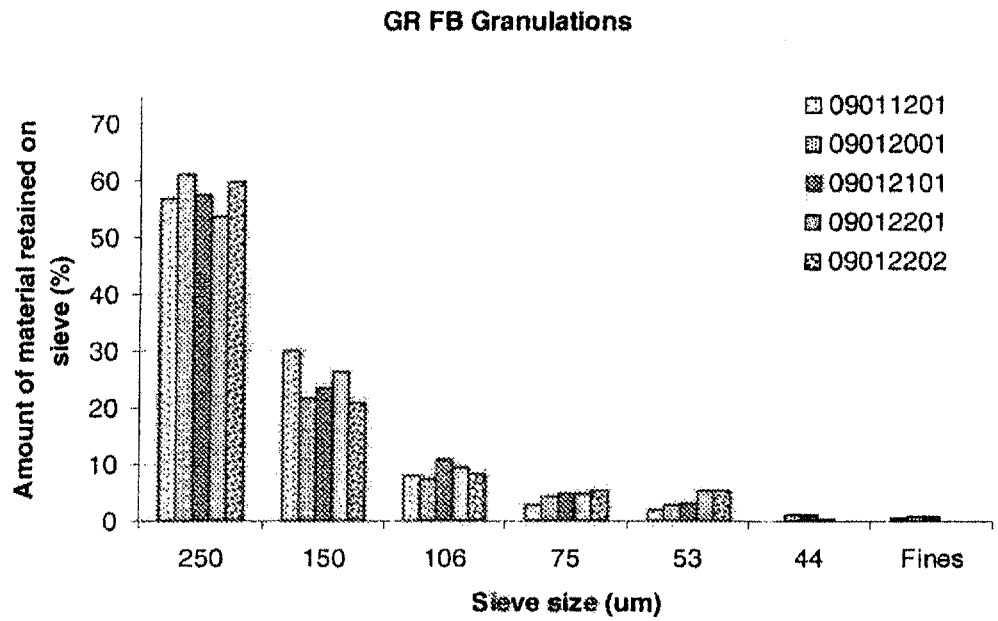
FIG. 18 is a graphical representation of the particle size distribution as determined for an extended release polymer matrix.
Figure 19:
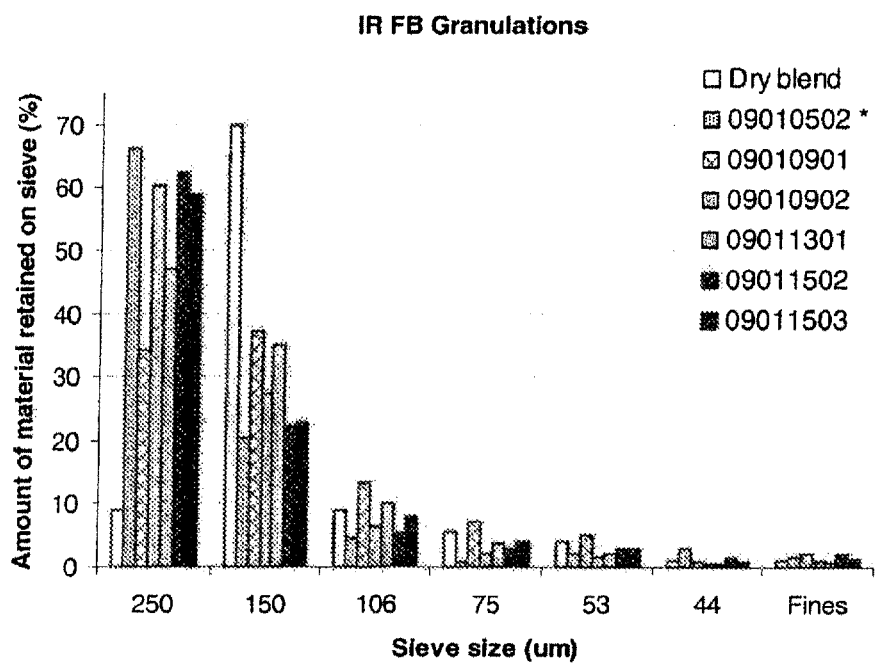
FIG. 19 is a graphical representation of the particle size distribution as determined for an IR portion of a dosage form.

The particle size distribution of the blend was determined using a particle size shaker with a timer (W.S. Tyler Inc., ROTAP, RX-29) and U.S. standard sieve series: No. 60 (250 um), 100 (150 um), 140 (106 um), 200 (75 um), 270 (53 um) and 325 (45 um). Fifty grams of sample was accurately weighed and transferred to the top sieve, then the shaker was allowed to shake for 5 minutes. The material remaining on the top of each sieve was then weighed to the nearest 0.1 gram. The results are provided in Table 23 below and shown in FIG. 18.

TABLE 23

| Sieve size (µm) | Lot 09011201 | Lot 09012001 | Lot 09012101 | Lot 09012201 | Lot 09012202 |
|---|---|---|---|---|---|
| 250 | 57.0 | 61.4 | 57.4 | 53.9 | 60.0 |
| 150 | 30.0 | 21.7 | 23.6 | 26.4 | 21.0 |
| 106 | 8.0 | 7.6 | 11.0 | 9.3 | 8.0 |
| 75 | 3.0 | 4.2 | 4.8 | 4.8 | 5.0 |
| 53 | 2.0 | 3.0 | 3.2 | 5.4 | 5.0 |
| 44 | 0 | 1.2 | 1.2 | 0.2 | 0 |
| Fines | 0.6 | 0.8 | 0.8 | 0.0 | 0 |

An immediate release matrix comprising acetaminophen and tramadol was then produced having the formulation presented in Table 24.

TABLE 24

| Ingredients | % wt/wt |
|---|---|
| Acetaminophen USP Powder | 0.30 |
| Tramadol HCl | 4.80 |
| Povidone USP (K-29/32) | 9.00 |
| AcDiSol | 3.00 |
| Lactose | 6.45 |
| Avicel PH101 | 6.45 |

Fluidized bed granulation was performed on Vector FL-M-1 Fluid Bed as described for the gastric retentive matrix. A binder solution of povidone and the tramadol was sprayed onto the acetaminophen. The granules were then blended with the remaining excipients. The granulation properties and the post-granulation characterization of the IR matrix are presented below in Table 25.

TABLE 25

| | 09010502 | 09010901 | 09010902 | 09011301 | 09011502 | 09011503 |
|---|---|---|---|---|---|---|
| Batch size (g) | 600 | 1000 | 1000 | 1000 | 1000 | 1000 |
| Inlet air (° C.) | 50-51 | 49-51 | 51-58 | 51-58 | 49-53 | 47-49 |
| Product temp at spray start (° C.) | 35 | 31 | 36 | 35 | 31 | 30 |
| Product temp during spray (° C.) | 32-38 | 28-31 | 33-38 | 33-36 | 29-35 | 29-32 |
| Spray rate (rpm) | 7-15 | 8-19 | 8-20 | 8-19 | 8-19 | 8-19 |
| Spraying time (min) | 22 | 25 | 37 | 36 | 37 | 37 |
| Product temp during drying (° C.) | 32-40 | 41 | 36-39 | 35-37 | 34-35 | 32-34 |
| Drying time (min) | 3 | 5 | 2 | 2 | 2 | 2 |
| Final LOD (%) | 1.8 | 1.03 | 1.43 | 1.6 | 1.95 | 2.19 |
| Bulk Density (g/ml) | N/M | 0.39 | 0.29 | 0.32 | 0.32 | 0.31 |
| Tap Density (g/ml) | N/M | 0.45 | 0.34 | 0.38 | 0.40 | 0.38 |
| Carr Index | N/M | 15 | 16 | 16 | 20 | 18 |

Compression of the gastric retentive extended release matrix with the immediate release matrix produced above was done using a Manesty® BB4 press, at a compression speed of 220 tablets per minute, tooled with a modified oval 0.4337" width×0.7450" length die.

A comparison of segments of data from a 12 minute run of the tablet press showed that the resultant tablets had a friability ranging from 0.01 to 0.12 and did not split during hardness testing. The comparison data are summarized in Table 26 below.

TABLE 26

| | Section | Beginning | Middle | End |
|---|---|---|---|---|
| Compression | Compression speed (rpm) | 32 | 32 | 32 |
| | Avg tablet weight (g) | 1.019 ± 0.018 | 1.012 ± 0.016 | 0.992 ± 0.033 |
| | Avg tablet hardness (kp) | 19.6 ± 1.1 | 18.9 ± 1.4 | 17.2 ± 2.5 |
| | $2^{nd}$ compression force (N) | 9.8 | 11.7 | 9.1 |
| | Avg tablet thickness (mm) | 7.8 + 0.03 | 7.8 ± 0.03 | 7.8 + 0.04 |
| | Tablets split during hardness testing (%) | 0 | 0 | 0 |
| | Friability (%) | 0.12 | 0.03 | 0.01 |
| | | Samples from bag 1/6 | Samples from bag 4/6 | Samples from bag 6/6 |

Example 7

A bilayer tablet with first and second doses of acetaminophen and tramadol, comprising a gastric retained extended release layer and an immediate release layer, and having a total weight of 1042 mg, was made according to the formulations presented in Table 27 (extended release) and Table 28 (immediate release). To prepare the extended release layer, methods described in Example 2 were used. The acetaminophen, the tramadol and the binder were first wet granulated using the fluid bed granulation described in Example 2. The resultant granulation mixture was then screened and blended with the polymer, filler, color agent, and lubricant in a V-blender.

To prepare the immediate release layer, methods described in Example 3 were used. All ingredients except magnesium stearate were wet granulated using the fluid bed granulation method, the granules were then screened and blended with lubricant in a V-blender then ready for compression.

The extended release component and the immediate release component was then compressed into a bilayer tablet using a Manesty BB4 press, tooled with a modified oval 0.4337" width×0.7450" length die. A compression force of 7-13 kN (kilo Newton) was used, with a speed of 1000-2200 tablets/min.

TABLE 27

| Ingredient | Function | wt % | Mg/tablet |
|---|---|---|---|
| Acetaminophen | active agent | 41.9 | 299.9 |
| Oxycodone Hydrochloride | active agent | 2.6 | 18.8 |
| Povidone, NF (Plasdone, K29/32) | binder | 3.4 | 17 |
| Polyethylene oxide, NF (Sentry™ POLYOX™ WSR | swellable and release-controlling polymer | 45.0 | 321.8 |

TABLE 27-continued

| Ingredient | Function | wt % | Mg/tablet |
|---|---|---|---|
| N60K, LEO | | | |
| Microcrystalline cellulose, NF (Avicel PH-101) | Filler | 5.8 | 41.5 |
| Opadry ® blue | color agent | 0.2 | 1.5 |
| Magnesium stearate, NF (non-bovine) | lubricant | 1.0 | 7.2 |
| Total | | 100.0 | 715.0 |

TABLE 28

| Ingredient | Function | wt % | Mg/tablet |
|---|---|---|---|
| Acetaminophen | active agent | 70.1 | 229.3 |
| Oxycodone Hydrochloride | active agent | 4.8 | 15.7 |
| Povidone, NF (Plasdone, K29/32) | binder | 9.0 | 29.4 |
| Croscarmellose sodium, NF (Ac-Di-Sol) | disintegrant | 3.0 | 9.8 |
| Microcrystalline cellulose, NF (Avicel PH-101) | Filler | 6.4 | 21.0 |
| Lactose monohydrate, NF (316 Fast Flow) | Compression-aid | 6.4 | 21.0 |
| Magnesium stearate, NF (non-bovine) | lubricant | 0.3 | 0.8 |
| Total | | 100.0 | 327.0 |

Figure 20:
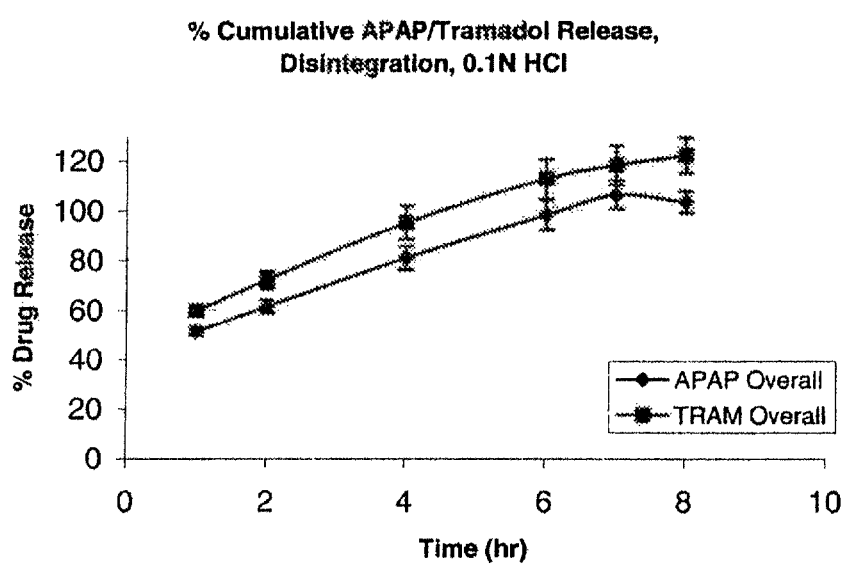
FIG. 20 is a graphical representation of the cumulative acetaminophen and tramadol disintegration release of a bilayer tablet.

Disintegration profiles for the tablets produced from the six batches described above were determined in USP Disintegration Tester in pH 1.2 0.1N HCl at 37±2° C. Samples were taken without media replacement at 1, 2, 4, 6, 7 and 8 hours. Cumulative release values for acetaminophen and tramadol at the time points are presented in Table 29 below, and illustrated in the graph in FIG. 20. The data show proportional release rates for the acetaminophen and tramadol over a period of 7 hours.

TABLE 29

| Active Ingredient | 1 h | 2 h | 4 h | 6 h | 7 h | 8 h |
|---|---|---|---|---|---|---|
| Acetaminophen | 51.4 | 61.6 | 81.0 | 98.3 | 106.5 | 103.5 |
| Tramadol | 59.8 | 72.3 | 95.3 | 112.8 | 118.3 | 122.1 |

Content uniformity of the bilayer tablets was tested using the methods described in Example 2. As shown in Table 30 below, the average content uniformity based on weight for acetaminophen was 95.5% of the label claim, while the average content uniformity based on weight for tramadol was 101.0% of the label claim. Standard deviations for acetaminophen and tramadol were 3.1 and 4.1, respectively.

TABLE 30

| Tablet | APAP, % LC (522.9 mg) | TRAM, % LC (37.7 mg) | APAP, % LC (base on wt) | TRAM, % LC (base on wt) |
|---|---|---|---|---|
| 1 | 91.5 | 95.6 | 93.8 | 98.5 |
| 2 | 92.8 | 97.2 | 95.9 | 101.0 |
| 3 | 93.4 | 98.2 | 96.1 | 101.6 |
| 4 | 88.9 | 93.3 | 92.1 | 97.1 |
| 5 | 90.8 | 94.0 | 91.3 | 94.9 |
| 6 | 92.7 | 96.8 | 94.9 | 99.7 |
| 7 | 93.2 | 97.7 | 94.5 | 99.7 |
| 8 | 92.6 | 98.0 | 96.0 | 102.1 |
| 9 | 95.2 | 102.0 | 101.5 | 109.2 |
| 10 | 90.3 | 93.2 | 90.7 | 94.1 |
| 11 | 92.8 | 98.5 | 97.0 | 103.5 |
| 12 | 94.3 | 99.7 | 97.8 | 103.9 |
| 13 | 87.3 | 91.5 | 89.9 | 94.7 |
| 14 | 92.0 | 99.0 | 99.0 | 107.1 |
| 15 | 90.0 | 93.1 | 91.3 | 95.0 |
| 16 | 91.4 | 96.5 | 94.1 | 99.9 |
| 17 | 88.8 | 91.8 | 89.6 | 93.2 |
| 18 | 92.5 | 97.8 | 97.4 | 103.5 |
| 19 | 92.3 | 98.5 | 98.7 | 105.9 |
| 20 | 94.6 | 100.7 | 99.2 | 106.1 |
| 21 | 94.1 | 99.7 | 98.5 | 105.0 |
| 22 | 94.5 | 100.2 | 98.3 | 104.8 |
| 23 | 93.3 | 98.4 | 96.0 | 101.8 |
| 24 | 97.2 | 101.9 | 100.3 | 105.8 |
| 25 | 90.6 | 95.6 | 95.5 | 101.4 |
| 26 | 91.1 | 95.2 | 93.7 | 98.5 |
| 27 | 91.0 | 95.3 | 94.8 | 99.9 |
| 28 | 91.7 | 96.8 | 96.2 | 102.0 |
| 29 | 92.5 | 97.0 | 95.7 | 100.9 |
| 30 | 92.3 | 96.5 | 94.9 | 99.7 |
| Ave. | 92.2 | 97.0 | 95.5 | 101.0 |
| Std. Dev. | 2.1 | 2.8 | 3.1 | 4.1 |
| % RSD | 2.2 | 2.9 | 3.2 | 4.1 |

Example 8

Figure 21:
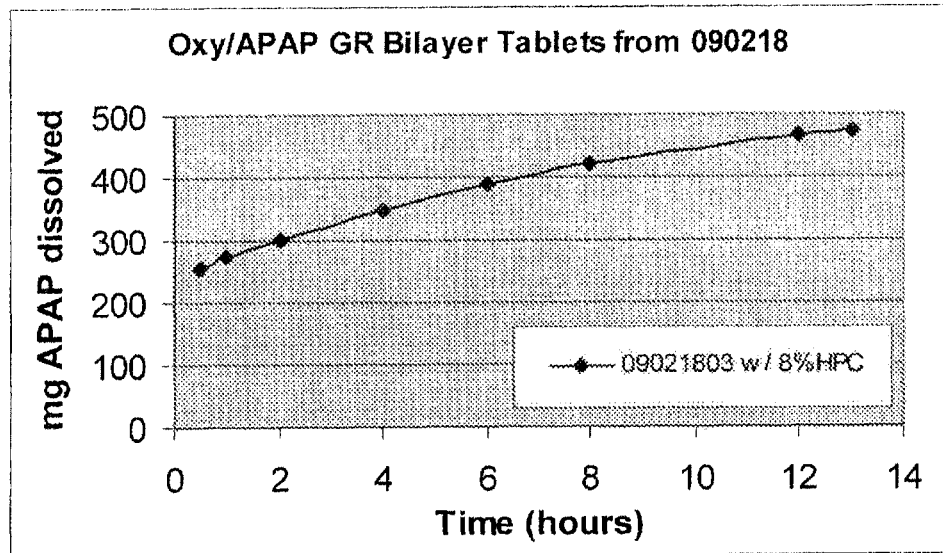
FIG. 21 is a graphical representation of the acetaminophen dissolution release profile for a bilayer tablet in which the IR layer contains hydroxypropylcellulose as a binder.
Figure 22:
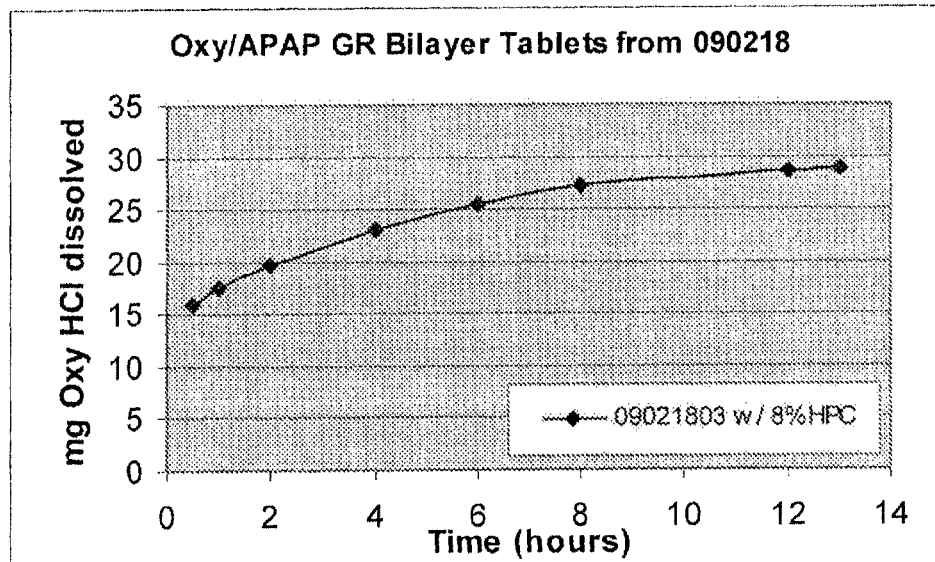
FIG. 22 is a graphical representation of the oxycodone hydrochloride dissolution release profile for a bilayer tablet in which the IR layer contains hydroxypropylcellulose as a binder.

A bilayer tablet comprising a gastric retained extended release layer and an immediate release layer is made containing the formulation presented in Table 31, in which the immediate release layer contained hydroxypropylcellulose (HPC) as the binder instead of PVP. The extended release layer contains PVP as the binder and was prepared as described in Example 2. The acetaminophen, the opioid and povidone (PVP) were first wet granulated using the fluid bed. The resultant granulation mixture was then blended with the polymer, filler, and lubricant in a V-blender. To prepare the immediate release layer, the acetaminophen, the opioid, and hydroxypropylcellulose (HPC) were first wet granulated using the fluid bed granulation. The resultant granulation mixture was then blended with the lubricant. The bilayer tablets were compressed on a Manesty BB4 machine using 0.4330" wide×0.7450 long modified oval tooling. The amounts of each component in the bilayer tablets is presented in Table 31. The dissolution release profile of acetaminophen and oxycodone HCl is shown in Table 32 and in FIG. 21 and FIG. 22.

TABLE 31

| Ingredient | Function | wt % | Mg/tablet |
|---|---|---|---|
| Acetaminophen | active agent | 50.88 | 500 |
| Oxycodone Hydrochloride | active agent | 3.05 | 30 |
| Hydroxypropyl cellulose, NF (Klucel EF) | binder | 2.88 | 28 |
| Polyethylene Oxide, NF (Sentry ™ | Swellable and release-controlling | 28.73 | 282 |

TABLE 31-continued

| Ingredient | Function | wt % | Mg/tablet |
|---|---|---|---|
| POLYOX ™ WSR N60K, LEO | polymer | | |
| Povidone, NF (Plasdone, K29/32) | binder | 1.53 | 15 |
| Croscarmellose sodium, NF (Ac-Di-Sol) | disintegrant | 1.08 | 11 |
| Microcrystalline cellulose, NF (Avicel PH-101) | Filler | 7.75 | 76 |
| Lactose monohydrate, NF (316 Fast Flow) | Compression-aid | 3.60 | 35 |
| Magnesium stearate, NF (non-bovine) | lubricant | 0.50 | 5 |
| Total | | 100.0 | 982.0 |

TABLE 32

| | N = 6 | |
|---|---|---|
| TIME (HOURS) | APAP | Oxycodone |
| 0.5 | 51.34154 | 53.25 |
| 1 | 54.83926 | 58.64767 |
| 2 | 60.27355 | 66.0131 |
| 4 | 69.5474 | 76.92073 |
| 6 | 77.73934 | 85.02003 |
| 8 | 84.23556 | 90.55967 |
| 12 | 93.07368 | 95.14833 |
| 13 | 94.74338 | 95.73057 |

Example 9

A bilayer tablet comprising a gastric retained extended release layer and an immediate release layer, having a total weight of 1042 mg, is made according to the formulations presented in Table 33 (extended release) and Table 34 (immediate release). To prepare the extended release layer, methods described in Example 2 are used. The acetaminophen, the opioid and the binder are first wet granulated using the fluid bed granulation described in Example 2. The resultant granulation mixture is then screened and blended with the polymer, filler, color agent, and lubricant in a V-blender.

To prepare the immediate release layer, methods described in Example 3 are used. All ingredients except magnesium stearate are wet granulated using the fluid bed granulation method, the granules are then screened and blended with lubricant in a V-blender then ready for compression.

The extended release component and the immediate release component are then compressed into a bilayer tablet using a Carver press, tooled with a modified oval 0.4850" width×0.7450" length modified Oval die. A compression force of 7-13 kN (kilo Newton) was used, with a speed of 1000-2200 tablets/min.

TABLE 33

| Ingredient | Function | wt % | Mg/tablet |
|---|---|---|---|
| Acetaminophen | active agent | 41.9 | 299.9 |
| Oxycodone Hydrochloride | active agent | 2.6 | 18.8 |
| Povidone, NF (Plasdone, K29/32) | binder | 3.4 | 17 |

TABLE 33-continued

| Ingredient | Function | wt % | Mg/tablet |
|---|---|---|---|
| Polyethylene oxide, NF (Sentry ™ POLYOX ™ WSR N60K, LEO | swellable and release-controlling polymer | 45.0 | 321.8 |
| Microcrystalline cellulose, NF (Avicel PH-101) | Filler | 5.8 | 41.5 |
| Opadry ® blue | color agent | 0.2 | 1.5 |
| Magnesium stearate, NF (non-bovine) | lubricant | 1.0 | 7.2 |
| Total | | 100.0 | 715.0 |

TABLE 34

| Ingredient | Function | wt % | Mg/tablet |
|---|---|---|---|
| Acetaminophen | active agent | 70.1 | 229.3 |
| Oxycodone Hydrochloride | active agent | 4.8 | 15.7 |
| Povidone, NF (Plasdone, K29/32) | binder | 9.0 | 29.4 |
| Croscarmellose sodium, NF (Ac-Di-Sol) | disintegrant | 3.0 | 9.8 |
| Microcrystalline cellulose, NF (Avicel PH-101) | Filler | 6.4 | 21.0 |
| Lactose monohydrate, NF (316 Fast Flow) | Compression-aid | 6.4 | 21.0 |
| Magnesium stearate, NF (non-bovine) | lubricant | 0.3 | 0.8 |
| Total | | 100.0 | 327.0 |

Example 10

A bilayer tablet containing a total of 500 mg acetaminophen and 15 mg oxycodone HCl designed for release of these active agents over 8 hours was manufactured using the wet granulation methods as described above using the formulations presented in Tables 35 and 36 for the ER and IR layers, respectively.

The extended release component and the immediate release component are then compressed into a bilayer tablet using a Manesty BB4 press, tooled with a modified oval 0.4337" width×0.7450" length die. A compression force of 1500 pounds was used, with a speed of 100% with a dwell time of 0.

TABLE 35

| | wt % | mg/tablet |
|---|---|---|
| Acetaminophen | 42.5 | 304.0 |
| Oxycodone HCl | 1.1 | 8.0 |
| Povidone, NF (Plasdone, K29/32) | 3.4 | 24.5 |
| Polyethylene oxide, 301 NF LEO | 45.0 | 321.8 |
| Microcrystalline Cellulose, NF (Avicel PH-101) | 3.9 | 28.1 |
| Opadry ® blue | 3.0 | 21.5 |
| Magnesium Stearate, NF (Non-Bovine) | 1.0 | 7.2 |
| Total | 100.0 | 715.0 |

TABLE 36

|  | wt % | mg/tablet |
|---|---|---|
| Acetaminophen | 68.8 | 196.0 |
| Oxycodone HCl | 2.5 | 7.0 |
| Povidone, USP (K29/32) | 10.3 | 29.4 |
| Ac-Di-Sol | 3.4 | 9.8 |
| Lactose | 7.4 | 21.0 |
| Avicel PH-101 | 7.4 | 21.0 |
| Magnesium Stearate, NF | 0.3 | 0.7 |
| Total | 100.0 | 284.9 |

Figure 23:
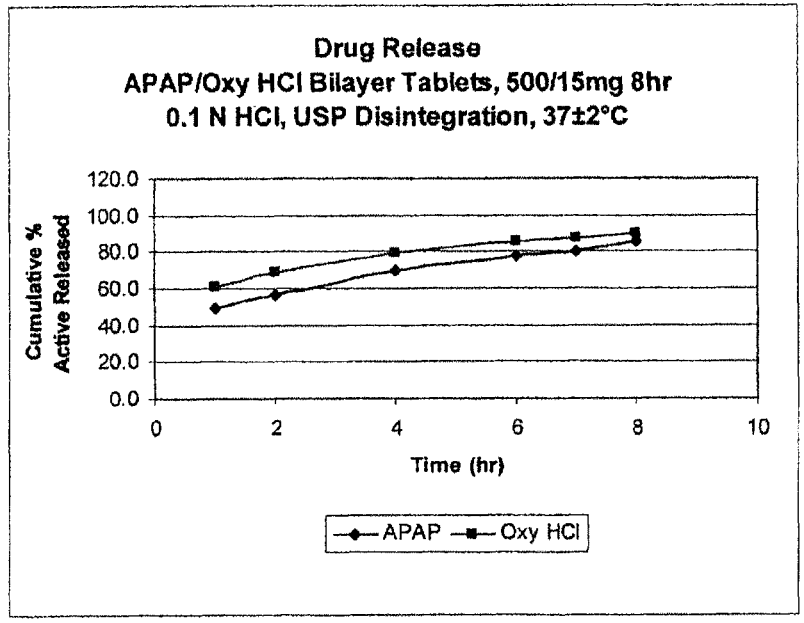
FIG. 23 is a graphical representation of the cumulative acetaminophen and oxycodone HCl disintegration release of a bilayer tablet formulated for 8-hour release.

The disintegration release profile of acetaminophen and oxycodone HCl formulated for acetaminophen and oxycodone release over 8 hours is provided in Table 37 and illustrated in FIG. 23.

TABLE 37

|  | Time Point (h) | | | | | |
|---|---|---|---|---|---|---|
|  | 1 | 2 | 4 | 6 | 7 | 8 |
| Cumulative % APAP released | 49.4 | 56.3 | 70.1 | 77.5 | 80.1 | 85.2 |
| Std. Dev. | 0.7 | 1.3 | 6.1 | 2.3 | 2.3 | 3.5 |
| Cumulative % Oxy released | 61.1 | 69.1 | 79.8 | 86.0 | 87.2 | 89.8 |
| Std. Dev. | 1.2 | 1.4 | 1.8 | 1.9 | 2.1 | 2.3 |

Example 11

A bilayer tablet containing a total of 500 mg acetaminophen and 15 mg oxycodone HCl formulated for release of the active pharmaceutical ingredients over 6 hours was manufactured as described above using the formuations presented in Tables 38 and 39 for the ER and IR layers, respectively.

TABLE 38

|  | wt % | mg/tablet |
|---|---|---|
| Acetaminophen | 37.8 | 270.0 |
| Oxycodone HCl | 1.1 | 8.0 |
| Povidone, NF (Plasdone, K29/32) | 3.4 | 24.5 |
| Polyethylene oxide, 301 NF LEO | 45.0 | 321.8 |
| Microcrystalline Cellulose, NF (Avicel PH-101) | 8.7 | 62.1 |
| Opadry ® blue | 3.0 | 21.5 |
| Magnesium Stearate, NF (Non-Bovine) | 1.0 | 7.2 |
| Total | 100.0 | 715.0 |

TABLE 39

|  | wt % | mg/tablet |
|---|---|---|
| Acetaminophen | 72.1 | 230.0 |
| Oxycodone HCl | 2.2 | 7.0 |
| Povidone, USP (K29/32) | 9.2 | 29.4 |
| Ac-Di-Sol | 3.1 | 9.8 |
| Lactose | 6.6 | 21.0 |
| Avicel PH-101 | 6.6 | 21.0 |
| Magnesium Stearate, NF | 0.3 | 0.8 |
| Total | 100.0 | 319.0 |

Figure 24:
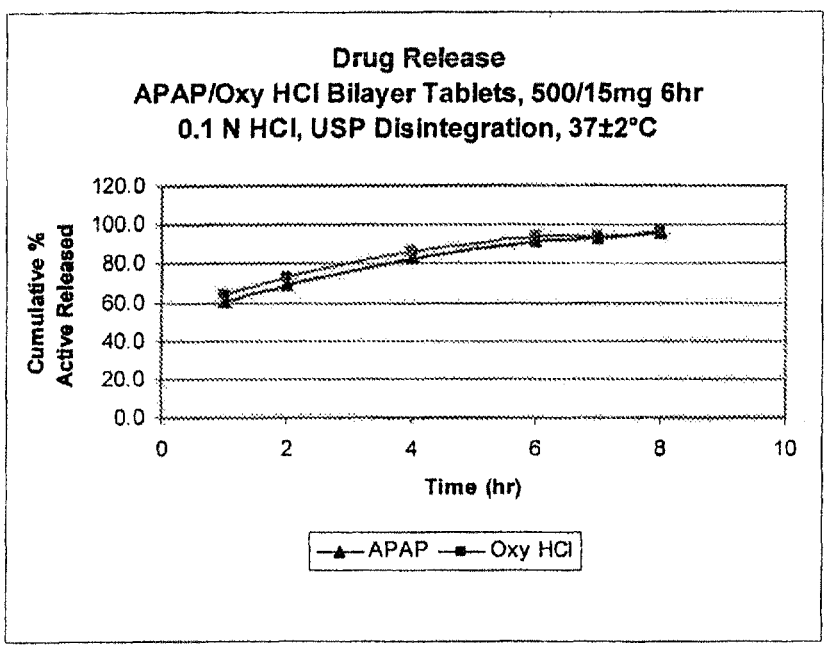
FIG. 24 is a graphical representation of the cumulative acetaminophen and oxycodone HCl disintegration release of a bilayer tablet formulated for 6-hour release.

The disintegration release profile of acetaminophen and oxycodone HCl from the tablet formulation for release over 6 hours is provided in Table 40 and illustrated in FIG. 24.

TABLE 40

|  | Time Point (h) | | | | | |
|---|---|---|---|---|---|---|
|  | 1 | 2 | 4 | 6 | 7 | 8 |
| Cumulative % APAP released | 60.2 | 69.3 | 83.1 | 91.7 | 93.5 | 95.8 |
| Std. Dev. | 1.3 | 2.1 | 2.2 | 1.6 | 1.5 | 1.3 |
| Cumulative % Oxy released | 63.8 | 73.8 | 86.8 | 93.7 | 94.5 | 96.6 |
| Std. Dev. | 1.4 | 3.3 | 2.3 | 1.8 | 2.8 | 2.5 |

Example 12

A bilayer tablet containing a total of 500 mg acetaminophen and 30 mg oxycodone HCl designed for release over 8 hours was manufactured using the wet granulation methods as described above using the formulations presented in Tables 41 and 42 for the ER and IR layers, respectively.

The extended release component and the immediate release component are then compressed into a bilayer tablet using a Manesty BB4 press, tooled with a modified oval 0.4337" width×0.7450" length die. A compression force of 7-13 kN (kilo Newton) was used, with a speed of 1000-2200 tablets/min.

TABLE 41

|  | wt % | mg/tablet |
|---|---|---|
| Acetaminophen | 42.5 | 304.0 |
| Oxycodone HCl | 2.2 | 16.0 |
| Povidone, NF (Plasdone, K29/32) | 3.4 | 24.6 |
| Polyethylene oxide, 301 NF LEO | 45.0 | 321.8 |
| Microcrystalline Cellulose, NF (Avicel PH-101) | 2.8 | 20.0 |
| Opadry ® blue | 3.0 | 21.5 |
| Magnesium Stearate, NF (Non-Bovine) | 1.0 | 7.2 |
| Total | 100.0 | 715.0 |

TABLE 42

|  | wt % | mg/tablet |
|---|---|---|
| Acetaminophen | 67.1 | 196.0 |
| Oxycodone HCl | 4.8 | 7.0 |
| Povidone, USP (K29/32) | 10.1 | 29.4 |
| Ac-Di-Sol | 3.4 | 9.8 |
| Lactose | 7.2 | 21.0 |
| Avicel PH-101 | 7.2 | 21.0 |
| Magnesium Stearate, NF | 0.25 | 0.7 |
| Total | 100.0 | 291.9 |

Figure 25:
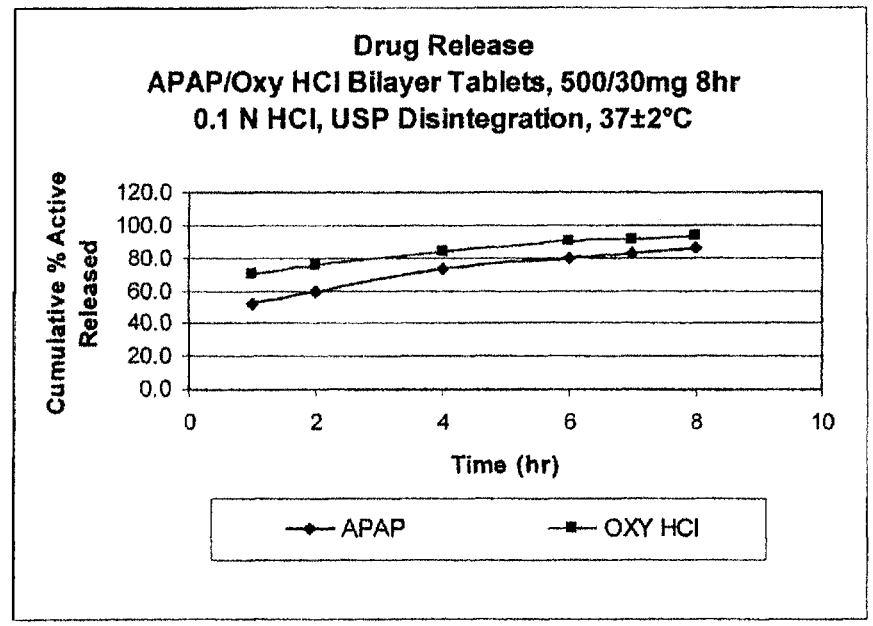
FIG. 25 is a graphical representation of the cumulative acetaminophen and oxycodone HCl disintegration release of a bilayer tablet formulated for 8-hour release.

The disintegration release profile of acetaminophen and oxycodone HCl formulated for acetaminophen and oxycodone release over 8 hours is provided in Table 43 and illustrated in FIG. 25.

TABLE 43

| | Time Point (h) | | | | | |
|---|---|---|---|---|---|---|
| | 1 | 2 | 4 | 6 | 7 | 8 |
| Cumulative % APAP released | 52.4 | 59.3 | 73.7 | 79.6 | 82.8 | 85.5 |
| Std. Dev. | 1.3 | 2.2 | 5.3 | 5.1 | 5.7 | 6.5 |
| Cumulative % Oxy released | 69.9 | 75.3 | 84.1 | 89.9 | 91.2 | 93.0 |
| Std. Dev. | 10.5 | 5.5 | 6.7 | 7.6 | 8.1 | 8.7 |

Example 13

A bilayer tablet containing a total of 500 mg acetaminophen and 30 mg oxycodone HCl formulated for release of the active pharmaceutical ingredients over 6 hours was manufactured as described above using the formulations presented in Tables 44 and 45 for the ER and IR layers, respectively.

TABLE 44

| | wt % | mg/tablet |
|---|---|---|
| Acetaminophen | 37.8 | 270.0 |
| Oxycodone HCl | 2.2 | 16.0 |
| Povidone, NF (Plasdone, K29/32) | 3.1 | 22.0 |
| Polyethylene oxide, 301 NF LEO | 45.0 | 321.8 |
| Microcrystalline Cellulose, NF (Avicel PH-101) | 7.9 | 56.7 |
| Opadry ® blue | 3.0 | 21.5 |
| Magnesium Stearate, NF (Non-Bovine) | 1.0 | 7.2 |
| Total | 100.0 | 715.0 |

TABLE 45

| | wt % | mg/tablet |
|---|---|---|
| Acetaminophen | 70.6 | 230.0 |
| Oxycodone HCl | 4.3 | 14.0 |
| Povidone, USP (K29/32) | 9.0 | 29.4 |
| Ac-Di-Sol | 3.0 | 9.8 |
| Lactose | 6.4 | 21.0 |
| Avicel PH-101 | 6.4 | 21.0 |
| Magnesium Stearate, NF | 0.3 | 0.8 |
| Total | 100.0 | 326.0 |

Figure 26:
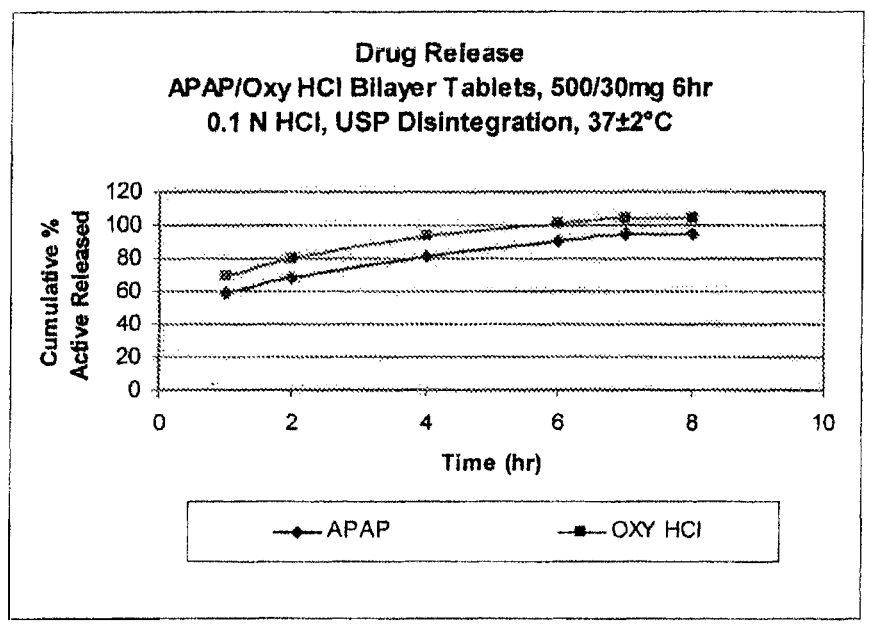
FIG. 26 is a graphical representation of the cumulative acetaminophen and oxycodone HCl disintegration release of a bilayer tablet formulated for 6-hour release.

The disintegration release profile of acetaminophen and oxycodone HCl from the tablet formulation for release over 6 hours is provided in Table 46 and illustrated in FIG. 26. The release profiles indicate that both acetaminophen and oxycodone exhibit approximately zero-order release kinetics over about a 6 to 8 hour period. In vivo erosion studies of the dosage forms to demonstrate gastric retention of the tables are described in Examples 17-18.

TABLE 46

| | Time Point (h) | | | | | |
|---|---|---|---|---|---|---|
| | 1 | 2 | 4 | 6 | 7 | 8 |
| Cumulative % APAP released | 59.2 | 67.9 | 80.9 | 90.2 | 94.4 | 95.0 |
| Std. Dev. | 1.0 | 1.7 | 1.8 | 1.8 | 1.9 | 1.9 |
| Cumulative % Oxy released | 69.7 | 79.8 | 93.3 | 101.0 | 104.7 | 104.4 |
| Std. Dev. | 1.4 | 2.1 | 2.1 | 2.6 | 4.1 | 2.1 |

Example 13

Studies were done to evaluate the effect of the binder on the degradation rate of oxycodone in the presence of polyethylene oxide in the ER portion of the dosage form. Specifically, the use of HPC or PVP. Oxycodone HCl as well as a physical blend of acetaminophen and oxycodone HCl were tested ("Physical Blend"). Single layer ER tablets containing acetaminophen (APAP) and oxycodone HCl (Oxy) were formulated using the fluid bed granulation method described above. Specifically, the acetaminophen and oxycodone were granulated in the presence of either HPC or PVP as the binder. Granulated mixtures were then dried and pressed into tablets. Physical blends and tablets were then stored at 40° C., 75% relative humidity (RH) in an open dish for 8 days. Physical blends and tablets were analyzed for the presence of an unknown impurity and the ratio of the unknown purity to oxycodone (Oxy) was calculated. Physical blend and granules data are listed as an average of three individual sample preparations. Tablet data were obtained by analyzing one composite sample from five tablets.

The results are summarized in Table 47 and show that oxycodone HCl was more stable in tablets formulated with HPC as compared to PVP as the binder and suggest that it may be beneficial to formulate both the IR and ER layers of the dosage form using HPC rather than PVP as the binder.

TABLE 47

| | | DHOXY/OXY (%)[1] | | | | |
|---|---|---|---|---|---|---|
| | | Physical Blend[4] | | | Tablets[5] | |
| | Polyox | t = 0 | 40° C., 75% RH, open-dish 8 days | Granules[4] t = 0 | t = 0 | 40° C., 75% RH, open-dish 8 days |
| Physical Blend | | | | | | |
| Oxy only | NA | 0.07 | 0.07 | NA | NA | NA |
| APAP (500 mg)/Oxy (30 mg) | NA | 0.02 | 0.10 | NA | NA | NA |
| APAP/Oxy as a ER Single Layer | | | | | | |
| APAP (304 mg) Oxy (16 mg) PVP (24.6 mg) | N60K | | | 1.35 | 1.41 | 1.49 |
| | | NA | NA | | | |
| | 301 | NA | NA | | 1.23 | 1.47 |
| APAP (304 mg) Oxy (16 mg) HPC (16.8 mg) | N60K | | | | | |
| | | NA | NA | 0.05 | 0** | 0.07 |
| | 301 | NA | NA | | 0.04** | 0.37 |
| MCC (160 mg) Oxy (16 mg) PVP (9.3 mg) | N60K | | | | | |
| | | NA | NA | 0.06 | 0.03 | 0.25 |
| | 301 | NA | NA | | 0.11 | 0.26 |
| APAP/Oxy IR/GR Bilayer | 301 | NA | NA | NA | 0.78 | 1.30 |

TABLE 47-continued

| | | DHOXY/OXY (%)[1] | | | |
|---|---|---|---|---|---|
| | | Physical Blend[4] | | | Tablets[5] |
| Polyox | t = 0 | 40° C., 75% RH, open-dish 8 days | Gran-ules[4] t = 0 | t = 0 | 40° C., 75% RH, open-dish 8 days |

(both IR and GR have PVP as the binder)

Example 14

Studies were done to evaluate the effect of antioxidants on the degradation rate of oxycodone in ER single layer tablets containing 500 mg acetaminophen and 30 mg oxycodone HCl which were high shear granulated with HPC as the binder. The antioxidant was added into the granulation process based on the maximum allowance level from the Inactive Ingredient Guide published by the FDA. The granules containing antioxidants were then blended with polyethylene oxide as described in previous examples. Samples were then stored at 40° C., 75% relative humidity (RH) in an open dish for 8 days, then analyzed. The results are presented below in Table 48 and show that the antioxidants citric acid, sodium metabisulfite, cysteine HCl reduce the degradation of oxycodone, thus suggesting that introducing antioxidant into the granulation process may be beneficial in minimizing degradation of the oxycodone or any opioid present in the dosage form.

TABLE 48

| | | DHOXY/OXY (%) | | | | |
|---|---|---|---|---|---|---|
| | | t = 0 | | 40° C., 75% RH, 8 days | | |
| Antioxidant | Polyox | RRT | % | RRT | % | Appearance |
| none | N60K | 0.70 | 0.00 | 0.70 | 0.16 | white to off-white |
| | 301 | 0.70 | NA | 0.70 | 0.20 | white to off-white |
| BHT | N60K | 0.68 | 0.06 | 0.69 | 0.20 | white to off-white |
| | | 0.72 | 0.05 | | | |
| | 301 | 0.70 | NA | 0.70 | 0.20 | white to off-white |
| Ascorbic Acid | N60K | 0.71 | 0.07 | 0.71 | 0.94 | brown |
| | 301 | 0.71 | 0.06 | 0.71 | 0.97 | brown |
| Citric Acid | N60K | 0.72 | 0.05 | 0.72 | 0.04 | slightly yellow |
| | 301 | 0.72 | NA | 0.72 | 0.03 | slightly yellow |
| Sodium Metabisulfite | N60K | 0.72 | 0.02 | 0.72 | 0.05 | white to off-white |
| | 301 | 0.72 | 0.06 | 0.72 | 0.04 | white to off-white* |
| Sodium Sulfite | N60K | 0.70 | NA | 0.70 | 0.13 | white to off-white |
| | | 0.72 | 0.03 | 0.72 | 0.04 | |
| | 301 | 0.70 | NA | 0.70 | 0.20 | white to off-white |
| | | 0.72 | 0.04 | 0.72 | NA | |
| Cystein HCl | N60K | 0.68 | NA | 0.68 | 0.10 | white to off-white |
| | | 0.72 | 0.08 | 0.72 | 0.05 | |
| | 301 | 0.68 | 0.05 | 0.68 | 0.10 | white to off-white |
| | | 0.72 | NA | 0.72 | 0.05 | |

*single yellow spat was observed randomly on some of the tablets.

Example 15

To produce oral dosage forms in which the oxycodone exhibits enhanced stability against oxidative degradation, a high-shear fluid bed granulation process was used in which the oxycodone HCl was granulated in the presence of pregelatinized starch, citric acid, microcrystalline cellulose, and EDTA disodium salt, dehydrate.

Powdered oxycodone HCl, microcrystalline cellulose (MCC), and citric acid powder (an antioxidant) were mixed together and charged into a high-shear granulator. An aqueous solution containing pregelatinized starch (PGS) and Na$_2$EDTA was sprayed into the high-speed granulator, resulting in the formation of wet granules. The wet granules were then dried until less than about 2% water remained in the granules. The dried granules had particle sizes ranging from about 100-300 μm. The composition of the protected oxycodone granules is summarized in Table 49.

TABLE 49

| Compound | Dry Weight (% tot. wt.) |
|---|---|
| Oxycodone HCl | 30.0% |
| MCC | 63.6% |
| PGS | 4.0% |
| Na$_2$EDTA | 0.4% |
| Citric acid | 2.0% |

The protected oxycodone granules were divided into two groups to be incorporated into batches of instant release (IR) granules and into batches of extended release (ER) granules used to form the IR and ER layers of a bilayer tablet, respectively. Both the IR granules and the ER granules were formed using separate fluid bed granulation processes. In each process, the previously-formed protected oxycodone granules, powdered acetaminophen (APAP), and various excipients including disintegrants, binders, and fillers were charged into the fluid bed granulation device and sprayed with a granulation fluid, resulting in the formation of IR granules in one batch and ER granules in a second batch. The composition of the resulting IR and ER granules are summarized in Table 50.

TABLE 50

| | Dry Wt. (% total wt.) | |
|---|---|---|
| Compound | IR Layer | ER Layer |
| Protected oxycodone granules | 16.1% | 14.2% |
| APAP | 67.8% | 81.2% |
| MCC | 5.0% | |
| Hydroxypropyl cellulose | 8.1% | 4.5% |
| Cross carmellose sodium | 3.0% | |

The IR granules were blended with lubricant excipients in preparation for the tablet pressing process. Similarly, the ER particles were blended with various excipients including lubricants, and polyethylene oxide polymer, and a filler in preparation for the tablet pressing process. The compositions of the IR blend and the ER blend are summarized in Table 51 below.

TABLE 51

| Compound | Dry Wt. (% total wt.) | |
| --- | --- | --- |
|  | IR Blend | ER Blend |
| IR granules | 99.25% |  |
| GR granules |  | 52.30% |
| Silicon dioxide | 0.50% | 0.50% |
| Magnesium stearate | 0.25% | 0.10% |
| MCC |  | 1.20% |
| Polyethylene oxide polymer |  | 45.00% |

The IR blend and the ER blend were loaded into a bilayer tablet press and formed into bilayer tablets having about 29% of the IR blend and about 71% the ER blend by weight.

A bilayer tablet was manufactured according to the method described in Example 15 according to the formulations in Table 52 (IR portion) and Table 53 (ER portion). The total tablet weight was 1006.5 mg.

TABLE 52

| Ingredient | mg/tablet | wt % |
| --- | --- | --- |
| Acetaminophen | 196.00 | 67.24 |
| Oxycodone HCl | 14.00 | 4.80 |
| Avicel (within protected granule) | 29.67 | 10.18 |
| Spress B825 | 1.87 | 0.64 |
| Citric Acid Anhydrous | 0.93 | 0.32% |
| EDTA disodium salt, dihydrate | 0.17 | 0.06 |
| Hydroxypropyl cellulose | 23.32 | 8.00 |
| AcDiSol | 8.74 | 3.00 |
| Avicel (as part of IR granule) | 14.57 | 5.00 |
| Silicon Dioxide | 1.46 | 0.50 |
| Mg Stearate | 0.73 | 0.25 |
| Total | 291.5 | 100.0 |

TABLE 53

| Ingredient | mg/tablet | wt % |
| --- | --- | --- |
| Acetaminophen | 304.00 | 42.52 |
| Oxycodone HCl | 16.00 | 2.24 |
| Avicel (within protected granule) | 33.89 | 4.74 |
| Spress B825 | 2.15 | 0.03 |
| Citric Acid Anhydrous | 1.07 | 0.15 |
| EDTA disodium salt, dihydrate | 0.21 | 0.03 |
| Hydroxypropyl cellulose | 16.87 | 2.36 |
| Polyox | 321.75 | 45.00 |
| Avicel (added to GR blend) | 8.37 | 1.17 |
| Silicon Dioxide | 3.58 | 0.05 |
| Mg Stearate | 7.15 | 1.00 |
| Total | 715.0 | 100.0 |

In vitro release profiles may be determined for the formulated tablet described above using standard USP Dissolution and Disintegration apparatuses as described in Examples above. In vivo studies to determine Example 16

Opioid agonists such as oxycodone have been reported to cause a reduction in motility in the antrum, which results in slowing of gastric emptying (Wood and Galligan, Physicians' Desk Reference, 59th edition (2005) p. 2818). This could affect the erosion time of an extended release gastric retained acetaminophen/opioid combination drug formulation. Preliminary studies were done to determine the effect of oxycodone on erosion time of acetaminophen extended-release tablets comprising a polymer matrix that swells to a size sufficient for retention in the stomach in the fed mode.

This was a randomized 2-way crossover study in 5 healthy female beagle dogs weighing between 12-16 kg to determine the erosion time of acetaminophen gastric retentive extended-release tablets with and without oxycodone administration. Following an overnight fast of at least 14 hours, the dogs were fed 100 g of canned dog food (Pedigree® Traditional ground Dinner with Chunky Chicken).

Fifteen minutes after the animals had consumed the food, the dosage forms were administered. In the oxycodone arm, oxycodone (14 mg in a gelatin capsule (0.28 mL of a 50 mg/mL solution in water)) was administered with the tablet to simulate the immediate-release portion of the proposed formulations. This was followed by a simulated extended-release over the next 4.5 hr (1.8 mg oxycodone in a gelatin capsule (0.036 mL of a 50 mg/mL solution in water) every 30 min for 4.5 hr) for nine doses and a total of 16 mg oxycodone. In addition to the initial feeding the animals were fed another 100 gm of food 4 hours after the first meal. The above procedure was repeated 2 day later with the opposite treatment.

Erosion of the gastric retentive extended-release acetaminophen tablets was assessed using fluoroscopy. Each tablet contained two radio-opaque strings in the shape of an "X". Separation of the strings was considered to signify complete erosion of the tablets. Images were obtained every 30 min until the strings separated. Individual and mean tablet erosion times are presented in Table 35. There was not a significant difference ($p>0.05$) in erosion time between control and oxycodone.

TABLE 54

| Tablet | Dog 1 | Dog 2 | Dog 3 | Dog 4 | Dog 5 | Mean ± SD |
| --- | --- | --- | --- | --- | --- | --- |
| Control | 4.25 h | 4.75 h | 4.75 h | 4.75 h | 4.75 h | 4.65 ± 0.22 h |
| Oxycodone | 6.00 h | 5.25 h | 5.75 h | 5.25 h | 4.75 h | 5.40 ± 0.49 h |

It was unexpectedly found that the co-administered oxycodone had no significant effect on the erosion time.

Example 17

A study to determine the erosion time of different extended release gastric retentive dosage forms as described herein is done using dogs as a means to predict the drug delivery time in humans. The bilayer tablets containing both the extended release and immediate release components are used in these studies. Each tablet has a total weight of about 1000 mg and contains 500 mg acetaminophen and 15 or 30 mg oxycodone HCl as indicated in Table 36. The gastric retentive (GR) portions of the tablets are formulated according to Example 2 above with the exception of the variations noted in Table 36. The immediate release (IR) layer is formulated according to Example 3 above, except that either hydroxypropyl cellulose or povidone is used as the binder as described in Table 36.

TABLE 55

| Formulation | Oxycodone HCl (mg/tablet) | Polymer (weight percent) | Binder (weight percent) |
|---|---|---|---|
| 1 (6 hr release) | 15 | POLYOX ® N60 K or 301 weight percent ranging from 10 to 55% | GR: PVP, 3 to 15 weight percent IR: PVP or HPC (hydroxypropyl cellulose) 3 to 15 weight percent |
| 2 (8 hr release) | 15 | POLYOX ® N60 K or 301 weight percent ranging from 15 to 55% | GR: PVP, 3 to 15 weight percent IR: PVP or HPC (hydroxypropyl cellulose) 3 to 15 weight percent |
| 3 (6 hr release) | 30 | POLYOX ® N60 K or 301 weight percent ranging from 10 to 55% | GR: PVP, 3 to 15 weight percent IR: PVP or HPC (hydroxypropyl cellulose) 3 to 15 weight percent |
| 4 (8 hr release) | 30 | POLYOX ® N60 K or 301 weight percent ranging from 15 to 55% | GR: PVP, 3 to 15 weight percent IR: PVP or HPC (hydroxypropyl cellulose) 3 to 15 weight percent |

A four-way crossover study is carried out in five healthy female beagle dogs. Following an overnight fast of 14 hours, the dogs are fed 100 g canned dog food. Fifteen minutes after the food has been consumed, the dogs are dosed with one of the four formulations to be tested. Four hours after the initial meal, the animals are fed another 100 g of canned dog food.

Erosion of the gastric retentive extended release oxycodone/acetaminophen tablets is assessed using fluoroscopy. Each tablet used in this protocol contains two radio-opaque strings in the shape of an "X." Separation of the strings is considered to signify complete erosion of the tablets. Images are obtained every 30 minutes until the strings separate. The above procedure is repeated at 3-4 day intervals until each dog has been administered four formulations.

Example 18

Erosion studies were carried out to test the erosion times of the tablets containing 500 mg acetaminophen and 15 mg oxycodone HCl as formulated in Tables 35-36 and 38-39 and tablets containing 500 mg acetaminophen and 30 mg oxycodone HCl as formulated in Tables 41-42 and 44-45.

Figure 27:
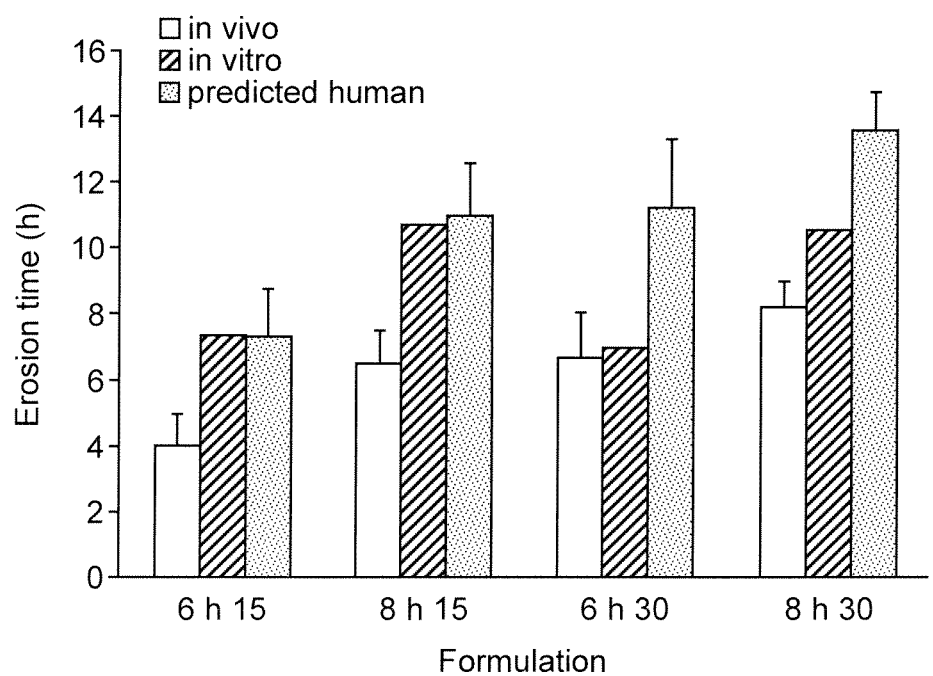
FIG. 27 is a graphical representation of erosion of bilayer tablets containing acetaminophen and oxycodone HCl in vitro, in vivo.

This study was conducted in 5 healthy female beagle dogs weighing between 12-16 kg to determine the erosion time of the bilayer tablets. Following an overnight fast of at least 14 hours, the dogs were fed 100 g of canned dog food (Pedigree® Traditional Ground Dinner with Chunky Chicken). Within 15 minutes of the dog consuming the meal they were administered one of the acetaminophen/oxycodone bilayer tablet formulations. Each dog received each formulation with at least 3 days between administrations. Erosion of the gastric retentive extended-release acetaminophen/oxycodone tablets was assessed using fluoroscopy. Each tablet contained two radio-opaque strings in the shape of an "X." Separation of the strings was considered to signify complete erosion of the tablets. Images were obtained every 30 minutes until the strings separated. The erosion results and predicted human erosion times (delivery times) are listed in Table 56 below and illustrated in FIG. 27.

TABLE 56

| | 15/500 6 h tablet | | 15/500 8 hr tablet | | 30/500 6 hr tablet | | 30/500 8 hr tablet | |
|---|---|---|---|---|---|---|---|---|
| Dog # | Dog erosion time (h) | Predicted human erosion time (h) | Dog erosion time (h) | Predicted human erosion time (h) | Dog erosion time (h) | Predicted human erosion time (h) | Dog erosion time (h) | Predicted human erosion time (h) |
| 1 | 3.25 | 6.18 | 7.25 | 12.18 | 7.25 | 12.18 | 7.75 | 12.93 |
| 2 | 3.00 | 5.80 | 7.25 | 12.18 | 4.25 | 7.68 | 9.25 | 15.18 |
| 3 | 5.25 | 9.18 | 6.75 | 11.43 | 7.25 | 12.18 | 8.25 | 13.68 |
| 4 | 4.75 | 8.43 | 6.25 | 10.68 | 7.75 | 12.93 | 8.75 | 14.42 |
| 5 | 3.75 | 6.93 | 4.75 | 8.43 | 6.75 | 11.43 | 7.25 | 12.18 |
| Mean ± SD | 4.00 ± 0.97 | 7.30 ± 1.45 | 6.45 ± 1.04 | 10.98 ± 1.56 | 6.65 ± 1.39 | 11.28 ± 2.08 | 8.25 ± 0.79 | 13.68 ± 1.18 |

No significant difference was observed between the in vitro erosion times for the 15 mg and 30 mg oxycodone formulation tablets. However, in vivo erosion indicated that oxycodone may have an effect on erosion as the 30 mg tablets had about a 2 hour increase in erosion time as compared to the tablets containing 15 mg oxycodone. Tablets containing 15 mg oxycodone did not appear to have a significant effect on erosion as erosion time for the tablet containing 15 mg oxycodone formulated for 6 hour release was not different from that for the tablet containing acetaminophen only formulated for 6 hour release.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for treating pain, comprising:
   administering at least twice daily, a dosage form comprising an extended release polymer matrix comprising a dose of acetaminophen and a dose of an opioid, wherein the extended release matrix is comprised of a swellable polymer and imbibes fluid after administration to swell to a size sufficient to promote gastric retention of the matrix, wherein the swellable polymer is selected from the group consisting of a polyalkylene oxide, a cellulosic polymer, a poly(acrylamide), a poly(N-vinyl lactam), and a polyvinylamine, and wherein within about 1 hour in an in vitro disintegration test the dosage form releases more than about 50% of the dose of acetaminophen, and wherein by about 6 hours in an in vitro disintegration test, the percent of opioid released from the dosage form is greater than the percent of acetaminophen released from the dosage form, and wherein the in vitro disintegration test is at 37° C. in 0.1N HCl.

2. The method of claim 1, wherein substantially all of the doses of acetaminophen and the opioid are released within about ten hours in an in vitro disintegration test.

3. The method of claim 1, wherein the dose of acetaminophen in the dosage form is between about 100-1300 mg.

4. The method of claim 1, wherein the dose of opioid in the dosage form is between about 5-40 mg.

5. The method of claim 4, wherein the dosage form comprises an opioid selected from the group consisting of oxycodone, hydrocodone, and pharmaceutically acceptable salts thereof.

6. The method of claim 3, wherein the dose of opioid in the dosage form is between about 5-40 mg.

7. The method of claim 6, wherein the dosage form comprises an opioid selected from the group consisting of oxycodone, hydrocodone, and pharmaceutically acceptable salts thereof.

8. The method of claim 1, wherein the dosage form comprises an immediate release portion.

9. The method of claim 7, wherein the dosage form comprises an immediate release portion.

10. The method of claim 9, wherein the dosage form comprises between about 20-50 weight percent of poly(ethylene oxide).

11. The method of claim 10, wherein the poly(ethylene oxide) has a molecular weight of between about 900,000 Daltons to about 4,000,000 Daltons.

12. The method of claim 1, wherein the dosage form comprises between about 20-50 weight percent of poly(ethylene oxide).

13. The method of claim 12, wherein the poly(ethylene oxide) has a molecular weight of between about 900,000 Daltons to about 2,000,000 Daltons.

14. A method for treating pain, comprising:
administering at least twice daily, a dosage form comprising an extended release polymer matrix comprising a dose of acetaminophen and a dose of an opioid, wherein the extended release matrix (i) is comprised of a swellable polymer and (ii) imbibes fluid after administration to swell to a size sufficient to promote gastric retention of the matrix, wherein the swellable polymer is selected from the group consisting of a polyalkylene oxide, a cellulosic polymer, a poly(acrylamide), a poly(N-vinyl lactam), and a polyvinylamine, and wherein at about 1 hour in an in vitro disintegration test the percent of acetaminophen released by the dosage form is greater than the percent of opioid released, and wherein by about 4-6 hours in an in vitro disintegration test, the dosage form releases greater than 90% of the dose of acetaminophen and the cumulative percent of opioid released is within about 10% of the cumulative percent of acetaminophen released, and wherein the in vitro disintegration test is at 37° C. in 0.1N HCl.

15. The method of claim 14, wherein substantially all of the doses of acetaminophen and the opioid are released within about ten hours in an in vitro disintegration test.

16. The method of claim 14, wherein the dose of acetaminophen in the dosage form is between about 100-1300 mg.

17. The method of claim 14, wherein the dose of opioid in the dosage form is between about 5-40 mg.

18. The method of claim 17, wherein the dosage form comprises an opioid selected from the group consisting of oxycodone, hydrocodone, and pharmaceutically acceptable salts thereof.

19. The method of claim 16, wherein the dose of opioid in the dosage form is between about 5-40 mg.

20. The method of claim 19, wherein the dosage form comprises an opioid selected from the group consisting of oxycodone, hydrocodone, and pharmaceutically acceptable salts thereof.

21. The method of claim 14, wherein the dosage form comprises an immediate release portion.

22. The method of claim 20, wherein the dosage form comprises an immediate release portion.

23. The method of claim 22, wherein the dosage form comprises between about 20-50 weight percent of poly(ethylene oxide).

24. The method of claim 23, wherein the poly(ethylene oxide) has a molecular weight of between about 900,000 Daltons to about 4,000,000 Daltons.

25. The method of claim 14, wherein the dosage form comprises between about 20-50 weight percent of poly(ethylene oxide).

26. The method of claim 25, wherein the poly(ethylene oxide) has a molecular weight of between about 900,000 Daltons to about 2,000,000 Daltons.

27. A method for treating pain, comprising:
administering at least twice daily, a dosage form comprising an extended release polymer matrix comprising a dose of acetaminophen and a dose of an opioid, wherein the extended release matrix (i) is comprised of a swellable polymer and (ii) imbibes fluid after administration to swell to a size sufficient to promote gastric retention of the matrix, wherein the swellable polymer is selected from the group consisting of a polyalkylene oxide, a cellulosic polymer, a poly(acrylamide), a poly(N-vinyl lactam), and a polyvinylamine, and wherein in an in vitro disintegration test the percent of acetaminophen released is greater than the percent of opioid released at times of 3 hours or less, at times greater than about 6 hours, the percent of opioid released is greater than the percent of acetaminophen released, and wherein the in vitro disintegration test is at 37° C. in 0.1N HCl.

28. The method of claim 27, wherein substantially all of the doses of acetaminophen and the opioid are released within about ten hours in an in vitro disintegration test.

29. The method of claim 27, wherein the dose of acetaminophen in the dosage form is between about 100-1300 mg.

30. The method of claim 27, wherein the dose of opioid in the dosage form is between about 5-40 mg.

31. The method of claim 30, wherein the dosage form comprises an opioid selected from the group consisting of oxycodone, hydrocodone, and pharmaceutically acceptable salts thereof.

32. The method of claim 29, wherein the dose of opioid in the dosage form is between about 5-40 mg.

33. The method of claim 32, wherein the dosage form comprises an opioid selected from the group consisting of oxycodone, hydrocodone, and pharmaceutically acceptable salts thereof.

34. The method of claim 27, wherein the dosage form comprises an immediate release portion.

35. The method of claim 33, wherein the dosage form comprises an immediate release portion.

36. The method of claim 35, wherein the dosage form comprises between about 20-50 weight percent of poly(ethylene oxide).

37. The method of claim 36, wherein the poly(ethylene oxide) has a molecular weight of between about 900,000 Daltons to about 4,000,000 Daltons.

38. The method of claim 27, wherein the dosage form comprises between about 20-50 weight percent of poly(ethylene oxide).

39. The method of claim 38, wherein the poly(ethylene oxide) has a molecular weight of between about 900,000 Daltons to about 2,000,000 Daltons.

40. The method of claim 1, wherein the swellable polymer is an alkyl-substituted cellulosic polymer or a polyalkylene oxide.

41. The method of claim 14, wherein the swellable polymer is an alkyl-substituted cellulosic polymer or a polyalkylene oxide.

42. The method of claim 27, wherein the swellable polymer is an alkyl-substituted cellulosic polymer or a polyalkylene oxide.

* * * * *